(12) United States Patent
Rabinowitz et al.

(10) Patent No.: US 11,369,588 B2
(45) Date of Patent: Jun. 28, 2022

(54) NADPH PRODUCTION BY THE 10-FORMYL-THF PATHWAY, AND ITS USE IN THE DIAGNOSIS AND TREATMENT OF DISEASE

(71) Applicant: The Trustees of Princeton University, Princeton, NJ (US)

(72) Inventors: Joshua D. Rabinowitz, Princeton, NJ (US); Jing Fan, Madison, WI (US); Gregory S. Ducker, Rocky Hill, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 15/266,596

(22) Filed: Sep. 15, 2016

(65) Prior Publication Data
US 2017/0000769 A1    Jan. 5, 2017

Related U.S. Application Data

(63) Continuation-in-part of application No. PCT/US2015/021578, filed on Mar. 19, 2015.

(60) Provisional application No. 62/219,736, filed on Sep. 17, 2015, provisional application No. 61/968,036, filed on Mar. 20, 2014.

(51) Int. Cl.
| | |
|---|---|
| *A61K 31/4162* | (2006.01) |
| *A61K 31/513* | (2006.01) |
| *A61K 45/06* | (2006.01) |
| *A61K 31/198* | (2006.01) |
| *A61K 31/519* | (2006.01) |
| *A61K 31/517* | (2006.01) |

(52) U.S. Cl.
CPC ........ *A61K 31/4162* (2013.01); *A61K 31/198* (2013.01); *A61K 31/513* (2013.01); *A61K 31/517* (2013.01); *A61K 31/519* (2013.01); *A61K 45/06* (2013.01)

(58) Field of Classification Search
CPC .................. A61K 31/4162; A61K 31/513
See application file for complete search history.

(56) References Cited

U.S. PATENT DOCUMENTS

| | | | |
|---|---|---|---|
| 3,536,809 | A | 10/1970 | Applezweig |
| 3,598,123 | A | 10/1971 | Zaffaroni |

(Continued)

FOREIGN PATENT DOCUMENTS

| | | |
|---|---|---|
| WO | WO 2016145252 | 9/2016 |
| WO | WO 2017189883 | 11/2017 |

(Continued)

OTHER PUBLICATIONS

Issarachot et al., J Nanopart Res, Jan. 2014;16:2276 (Year: 2014).*

(Continued)

*Primary Examiner* — San Ming R Hui
(74) *Attorney, Agent, or Firm* — Jeffrey I. Auerbach; AuerbachSchrot LLC

(57) ABSTRACT

A 10-formyl-THF pathway for producing NADPH is useful in the diagnosis and treatment of cancer and metabolic disease, in the development of new antineoplastic agents and/or regimens, in the development of new methods for measuring metabolic pathway activity, and in the development of new therapeutics for treating metabolic disease.

15 Claims, 53 Drawing Sheets

Specification includes a Sequence Listing.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,696,483 | B2* | 2/2004 | Singh .................. A61K 31/00 514/450 |
| 8,058,430 | B2* | 11/2011 | Wright ................. A61P 35/00 544/277 |
| 10,077,273 | B2 | 9/2018 | Rabinowitz et al. |
| 10,584,132 | B2 | 3/2020 | Rabinowitz et al. |
| 10,646,475 | B2 | 5/2020 | Rabinowitz et al. |
| 10,772,862 | B2 | 9/2020 | Rabinowitz et al. |
| 2002/0127229 | A1* | 9/2002 | Bagshawe ............. B82Y 5/00 424/178.1 |
| 2003/0053418 | A1* | 3/2003 | Kabamba ............. H04L 1/0002 370/252 |
| 2007/0249545 | A1 | 10/2007 | Rodriguez-Lopez et al. |
| 2010/0047314 | A1* | 2/2010 | Ellies ................. A61K 9/0019 424/423 |
| 2013/0273533 | A1 | 10/2013 | Hellerstein |

FOREIGN PATENT DOCUMENTS

| | | |
|---|---|---|
| WO | WO 2019006003 | 1/2019 |
| WO | WO 2020041662 | 2/2020 |

OTHER PUBLICATIONS

Walling, Investigational New Drugs, 2006;24:37-77 (Year: 2006).*
Locasale, Nat Rev Cancer, 2013;13(8):572-583 (Year: 2013).*
Gessi et al., Biochimica et Biophysica Acta, 2011;1808:1400-1412 (Year: 2011).*
Anguera, M.C. et al., (2006) "Regulation of Folate-mediated One-carbon Metabolism by 10-Formyltetrahydrofolate Dehydrogenase," J. Biol. Chem. 281(27):18335-18342.
Birrell, J.A. et al., (2013) "Investigation of NADH Binding, Hydride Transfer, and $NAD^+$ Dissociation during NADH Oxidation by Mitochondrial Complex I Using Modified Nicotinamide Nucleotides," Biochemistry 52(23):4048-4055.
Fan, J. et al., (2014) "Quantitative Flux Analysis Reveals Folate-Dependent NADPH Production," Nature 510(7504):298-302.
International Search Report PCT/US2015/021578 (WO 2015/160470) (dated 2015) (3 pages).
Written Opinion of the International Searching Authority PCT/US2015/021578 (WO 2015/160470) (dated 2015) (7pages).
Agledal, L. et al. (2010) "The Phosphate Makes A Difference: Cellular Functions Of NADP," Redox Rep. 15(1):2-10.
Al-Dwairi, A. et al. (2012) "Cytosolic Malic Enzyme 1 (ME1) Mediates High Fat Diet-Induced Adiposity, Endocrine Profile, And Gastrointestinal Tract Proliferation-Associated Biomarkers In Male Mice," PLoS One 7, e4671.
Alfarouk, K.O. et al. (2011) "Tumor Acidity As Evolutionary Spite," Cancers 3(4):408-414.
Anastasiou, D. et al. (2011) "Inhibition Of Pyruvate Kinase M2 By Reactive Oxygen Species Contributes To Cellular Antioxidant Responses," Science 334:1278-1283.
Aragon, J.J. et al. (1980) "Permeabilization Of Animal Cells For Kinetic Studies Of Intracellular Enzymes: In Situ Behavior Of The Glycolytic Enzymes Of Erythrocytes," Proc. Natl. Acad. Sci. (U.S.A.) 77(11):6324-6328.
Ayromlou, H. et al. (2011) "Oxidative Effect Of Methotrexate Administration In Spinal Cord Of Rabbits" J. Pakistan Med. Assoc. 61:1096-1099.
Bagchi, S. et al. (1987) "Structure and Expression of Murine Malic Enzyme mRNA," J. Biol. Chem. 262(4):1558-1565.
Bonner, M.Y. et al. (2012) "Targeting NADPH Oxidases For The Treatment Of Cancer And Inflammation;" Cell. Mol. Life Sci. 69(14):2435-2442.
Boucher, A. et al. (2004) "Biochemical Mechanism Of Lipid-Induced Impairment Of Glucose-Stimulated Insulin Secretion And Reversal With A Malate Analogue," J. Biol. Chem. 279:27263-27271.
Bradley, K.K. et al. (2001) "Purine Nucleoside-Dependent Inhibition Of Cellular Proliferation In 1321N1 Human Astrocytoma Cells," J. Pharmacol. Exper. Therap. 299:748-752 (Abstract Only).
Brekke, E.M. et al. (2012) "Quantitative Importance Of The Pentose Phosphate Pathway Determined By Incorporation Of $^{13}C$ From [2-$^{13}C$]- And [3-$^{13}C$]Glucose Into TCA Cycle Intermediates And Neurotransmitter Amino Acids In Functionally Intact Neurons," J. Cereb. Blood Flow Metab. 32:1788-1799.
Calvert, A.H. (2004) "Biochemical Pharmacology Of Pemetrexed;" Oncology (Williston Park) 18(13 Suppl 8):13-17.
Chaneton, B. et al. (2012) "Serine Is A Natural Ligand And Allosteric Activator Of Pyruvate Kinase M2," Nature 491:458-462.
Christensen, K.E. et al. (2008) "Mitochondrial Methylenetetrahydrofolate Dehydrogenase, Methenyltetrahydrofolate Cyclohydrolase, And Formyltetrahydrofolate Synthetases," Vitamins Hormones 79:393-410 (Abstract Only).
Circu, M.L. et al. (2011) "Disruption Of Pyridine Nucleotide Redox Status During Oxidative Challenge At Normal And Low-Glucose States: Implications For Cellular Adenosine Triphosphate, Mitochondrial Respiratory Activity, And Reducing Capacity In Colon Epithelial Cells," Antioxid. Redox Signal 14:2151-2162.
Cui, X. (2012) "Reactive Oxygen Species: The Achilles' Heel Of Cancer Cells?" Antioxid. Redox Signal. 16(11):1212-1214.
D' Alessandro, A. et al. (2013) "Proteomics And Metabolomics In Cancer Drug Development," Expert Rev. Proteomics 10(5):473-488 (Abstract Only).
Dang, C.V. (2011) "Therapeutic Targeting Of Cancer Cell Metabolism," J. Molec. Med. (Berl) 89(3):205-212.
Dang, C.V. (2012) "Links Between Metabolism And Cancer?" Genes Dev. 26(9):877-890.
Deberardinis, R.J. et al. (2007) "Beyond Aerobic Glycolysis: Transformed Cells Can Engage In Glutamine Metabolism That Exceeds The Requirement For Protein And Nucleotide Synthesis?" Proc. Natl. Acad. Sci. (U.S.A.) 104:19345-19350.
Degenhardt, K. et al. (2002) "BAX And BAK Mediate P53-Independent Suppression Of Tumorigenesis," Cancer Cell 2:193-203.
Duarte, N. C. et al. (2007) "Global Reconstruction Of The Human Metabolic Network Based On Genomic And Bibliomic Data," Proc. Natl. Acad. Sci. (U.S.A.) 104:1777-1782.
Ducker, G.S. et al. (Epub Sep. 15, 2016) "One-Carbon Metabolism in Health and Disease," Cell. Metab. 25(1):27-42.
Eruslanov, E. et al. (2010) "Identification Of ROS Using Oxidized DCFDA And Flow-Cytometry," Methods Molec. Biol. 594:57-72 (Abstract Only).
Ferreira, L.M. (2010) "Cancer Metabolism: The Warburg Effect Today" Exp. Molec. Pathol. 89(3):372-380 (Abstract Only).
Fogg, V.C. et al. (2011) "Mitochondria In Cancer: At The Crossroads Of Life And Death," Chin. J. Cancer 30(8):526-539.
Folger, O. et al. (2011) "Predicting Selective Drug Targets In Cancer Through Metabolic Networks," Mol. Syst. Biol. 7:501 (pp. 1-10).
Gatenby, R.A. et al. (2004) "Why Do Cancers Have High Aerobic Glycolysis?" Nature Reviews Cancer 4(11):891-899 (Abstract Only).
Gogvadze, V. et al. (2009) "The Warburg Effect And Mitochondrial Stability In Cancer Cells" Molec. Aspects Med. 31(1):60-74 (Abstract Only).
Green, H. et al. (1974) "An Established Pre-Adipose Cell Line and Its Differentiation In Culture," Cell 3:127-133 (Abstract Only).
Gregson, A. et al. (2005) "Mechanisms of Resistance of Malaria Parasites to Antifolates" Pharmacol. Rev. 57:117-145.
Hagner, N. et al. (2010) Cancer Chemotherapy: Targeting Folic Acid Synthesis, Cancer Manag. Res. 2:293-301.
Hosogai, N. et al. (2007) "Adipose Tissue Hypoxiain Obesity And Its Impact On Adipocytokine Dysregulation," Diabetes 56:901-911;

(56) References Cited

OTHER PUBLICATIONS

Trayhum, P. (2013) "Hypoxia And Adipose Tissue Function And Dysfunction In Obesity," Physiol. Rev. 93:1-21.
Irwin, M.E. et al. (2013) "Redox Control Of Leukemia: From Molecular Mechanisms To Therapeutic Opportunities," Antioxid. Redox Signal. 18(11):1349-1383.
Jain, M. et al. (2012) "Metabolite Profiling Identifies A Key Role For Glycine In Rapid Cancer Cell Proliferation" Science 336:1040-1044.
Jang, M. et al. (2013) "Cancer Cell Metabolism: Implications For Therapeutic Targets" Exp. Molec. Med. 45:e45. doi: 10.1038/emm.2013.85.
Jang, C. et al. (2018) "Metabolomics and Isotope Tracing," Cell 173(4):822-837.
Jiang, P. et al. (2013) "Reciprocal Regulation OfP53 And Malic Enzymes Modulates Metabolism And Senescence," Nature 493:689-693.
Jitrapakdee, S. et al. (2008) "Structure, Mechanism and Regulation of Pyruvate Carboxylase," Biochem J. 413:369-387.
Joerger, M. et al. (2010) "The Role Of Pemetrexed In Advanced Non Small-Cell Lung Cancer: Special Focus On Pharmacology And Mechanism Of Action," Curr. Drug Targets 11(1):37-47 (Abstract Only).
Kamphorst, J.J. et al. (2014) "Ouantitative Analysis Of Acetyl-CoA Production In Hypoxic Cancer Cells Reveals Substantial Contribution From Acetate," Cancer Metab. 2:1-8.
Kim, J.W. (2006) "Cancer's Molecular Sweet Tooth And The Warburg Effect," Cancer Res. 66(18):8927-8930.
Kim, J.W. et al. (2006) "HIF-1-Mediated Expression Of Pyruvate Dehydrogenase Kinase: A Metabolic Switch Required For Cellular Adaptation To Hypoxia" Cell. Metab. 3:177-185.
Lee, C.Y. et al. (1980) "Identification And Biochemical Analysis Of Mouse Mutants Deficient In Cytoplasmic Malic Enzyme," Biochemistry 19:5098-5103.
Lee, W. N. et al. (1998) Mass Isotopomer Study Of The Nonoxidative Pathways Of The Pentose Cycle With [1,2-$^{13}C_2$]Glucose, Am. J. Physiol. 274:E843-E851.
Lemons, J.M. et al. (2010) "Quiescent Fibroblasts Exhibit High Metabolic Activity" PLoS Biol. 8:e1000514 (pp. 1-10).
Lewis, C. et al. (2014) "Tracing Compartmentalized NADPH Metabolism in the Cytosol and Mitochondria of Mammalian Cells," Mol. Cell 55:253-263.
Locasale, J.W. et al. (2011) "Phosphoglycerate Dehydrogenase Diverts Glycolytic Flux And Contributes To Oncogenesis" Nature Genetics 43:869-874.
Lu, C.W. et al. (2008) "Induction Of Pyruvate Dehydrogenase Kinase-3 By Hypoxia-Inducible Factor-1 Promotes Metabolic Switch And Drug Resistance" J. Biol. Chem. 283:28106-28114.
Lu, W. et al. (2010) "Metabolomic Analysis Via Reversed-Phase Ion-Pairing Liquid Chromatography Coupled To A Stand-Alone Orbitrap Mass Spectrometer" Anal. Chem. 82:3212-3221.
Maddocks, O.D. et al. (2013) "Serine Starvation Induces Stress And P53-Dependent Metabolic Remodelling In Cancer Cells," Nature 493:542-546.
Mathew, R. (2008) "Immortalized Mouse Epithelial Cell Models To Study The Role Of Apoptosis In Cancer," Methods Enzymol. 446:77-106 (Abstract Only).
McGuire, J.J. (2003) "Anticancer Antifolates: Current Status And Future Directions," Curr. Pharm. Des. 9(31):2593-2613 (Abstract Only).
Melamud, E. et al. (2010) "Metabolomic Analysis And Visualization Engine For LC-MS Data" Anal. Chem. 82:9818-9826.
Metallo, C.M. et al. (2009) "Evaluation Of $^{13}C$ Isotopic Tracers For Metabolic Flux Analysis In Mammalian Cells," J. Biotechnol. 144:167-174.
Millard, P. et al. (2QVl)"IsoCor: Correcting MS Data In Isotope Labeling Experiments," Bioinformatics 28:1294-1296.
Mullen, A.R. et al. (2011) "Reductive Carboxylation Supports Growth In Tumour Cells With Defective Mitochondria," Nature 481:385-388.

Munger, J. et al. (2008) "Systems-Level Metabolic Flux Profiling Identifies Fatty Acid Synthesis As A Target For Antiviral Therapy," Nat. Biotechnol. 26:1179-1186.
Nam, S.O. et al. (2013) "Possible Therapeutic Targets Among The Molecules Involved In The Warburg Effect In Tumor Cells," Anticancer Res. 33(7):2855-2860.
Nguyen, P. et al. (2008) "Liver Lipid Metabolism," J. Anim. Physiol. Anim. Nutr. (Berl). 92:272-283.
Nilsson, R. et al. (2014) "Metabolic Enzyme Expression Highlights A Key Role For MTHFD2 And The Mitochondrial Folate Pathway In Cancer," Nature Commun. 5:3128.
Nzila, A. et al. (2014) "Impact Of Folate Supplementation On The Efficacy Of Sulfadoxine / Pyrimethamine In Preventing Malaria In Pregnancy: The Potential Of 5-Methyl-Tetrahydrofolate," J. Antimicrob. Chemother. 69:323-330.
Palsson-McDermott, E.M. et al. (2013) "The Warburg Effect Then And Now: From Cancer To Inflammatory Diseases," Bioessays 35(11):965-973 (Abstract Only).
Patra, K.C. et al. (2014) "The Pentose Phosphate Pathway And Cancer," Trends Biochem Sci. Aug. 2014; 39(8): 347-354.
Peri, K.G. et al. (1989) "Nucleotide Sequence Of The Human NAD-Dependent Methylene-Tetrahydrofolate Dehydrogenase-Cyclohydrolase," Nucleic Acids Res 17(21):8853.
Ponisovskiy, M.R. (2011) "Warburg Effect Mechanism As The Target For Theoretical Substantiation Of A New Potential (.ancer Treatment," Crit. Rev. Eukaryot. Gene. Expr. 21(1):13-28 (Abstract Only).
Possemato, R. et al. (2011) "Functional Genomics Reveal That The Serine Synthesis Pathway Is Essential In Breast Cancer," Nature 476:346-350.
Price, N.E. et al. (1996) "Kinetic And Chemical Mechanisms Of The Sheep Liver 6-Phosphogluconate Dehydrogenase," Arch. Biochem. Biophys. 336:215-223 (Abstract Only).
Razungles, J. et al. (2013) "[The Warburg Effect: From Theory To Therapeutic Applications In Cancer]," Med Sci (Paris). (11):1026-1033.
Rosen, E.D. et al. (2006) "Adipocyte Differentiation From The Inside Out," Nat. Rev. Mol. Cell Biol. 7:885-896 (Abstract Only).
Rutter, W.J. et al. (1958) "Purification and Properties of Pigeon Liver Malic Enzyme," J. Biol. Chem. 233:374-382.
Shreve, D.S. et al. (1980) "Kinetic Mechanism Of Glucose-6-Phosphate Dehydrogenase From The Lactating Rat Mammary Gland. Implications For Regulation," J. Biol. Chem. 255:2670-2677.
Son, J. et al. (2013) "Glutamine Supports Pancreatic Cancer Growth Through A KRAS-Regulated Metabolic Pathway," Nature 496:101-105.
Stanton, R.C. (2012) "Glucose-6-Phosphate Dehydrogenase, NADPH, And Cell Survival," IUBMB Life 64(5):362-369.
Stincone, A. et al. (Epub Sep. 22, 2014) "The Return Of Metabolism: Biochemistry And Physiology Of The Pentose Phosphate Pathway," Biol. Rev. Camb. Philos. Soc. 90(3):927-9630.
Stoecklin, F.B. et al. (1986) "Formation Of Hexose 6-Phosphates From Lactate + Pyruvate + Glutamate By A Cell-Free System From Rat Liver," Biochem J. 236(1):61-70.
Surmont, V.F. et al. (2011) "Raltitrexed in Mesothelioma," Expert Rev. Anticancer Ther. 11(10):1481-1490 (Abstract Only).
Sutterlin, H. et al. (2014) "Accumulation Of Phosphatidic Acid Increases Vancomycin Resistance In *Escherichia coli*," J. Bacteriol. 196(18):3214-3220.
Tedeschi, P.M. et al. (2013) "Contribution Of Serine, Folate And Glycine Metabolism To The ATP, NADPH And Purine Requirements Of Cancer Cells," Cell Death Dis. 4:e877 (pp. 1-12).
Tibbetts, A.S. et al. (2010) "Compartmentalization Of Mammalian Folate-Mediated One-Carbon Metabolism," Annu. Rev. Nutr. 30:57-81 (Abstract Only).
Tomao, F. et al. (2009) "Emerging Role Of PemetrexedIn Ovarian Cancer," Expert Rev. Anticancer Ther. 9(12):1727-1735 (Abstract Only).
Upadhyay, M. et al. (2012) "The Warburg Effect: Insights From The Past Decade," Pharmacol. Ther. 137(3):318-330 (Abstract Only).
Vander Heiden, M.G. et al. (2009) "Understanding The Warburg Effect: The Metabolic Requirements Of Cell Proliferation," Science 324:1029-1033.

(56) References Cited

OTHER PUBLICATIONS

Warburg, O. (1956) "On The Origin Of Cancer Cells," Science 123:309-314.

Wiechert, W. et al. (1999) "Bidirectional Reaction Steps In Metabolic Networks: III. Explicit Solution And Analysis Of Isotopomer Labeling Systems," Biotechnol. Bioeng. 66:69-85 (Abstract Only).

Weitzel, M. et al. (2013) "13CFLUX2—High-Performance Software Suite For $^{13}$C-Metabolic Flux Analysis," Bioinformatics 29:143-145.

Wellen, K.E. et al. (2009) "ATP-Citrate Lyase Links Cellular Metabolism To Histone Acetylation," Science 324:1076-1080.

Wen, S. et al. (2Q13)"Targeting Cancer Cell Mitochondria As A Therapeutic Approach," Future Med. Chem. 5(1):53-67.

Wise, E.M. (1964) "Malic Enzyme And Lipogenesis," Proc. Natl. Acad. Sci. (U.S.A.) 52:1255-1263.

Wise, D.R. et al. (2011) "Hypoxia Promotes Isocitrate Dehydrogenase-Dependent Carboxylation Of A-Ketoglutarate To Citrate To Support Cell Growth And Viability," Proc. Natl. Acad. Sci. (U.S.A.) 108:19611-19616.

Wright, A.E. et al. (2009) "Isolation, Synthesis And Biological Activity Of Aphrocallistin, An Adenine Substituted Bromotyramine Metabolite From The Hexactinellida Sponge Aphrocallistes Beatrix," J. Nat. Prod. 72(6):1178-1183 and Supplementary Materials.

Yang, X.M., et al. (1993) "NAD-Dependent Methylenetetrahydrofolate Dehydrogenase-Methenyltetrahydrofolate Cyclohydrolase Is The Mammalian Homolog Of The Mitochondrial Enzyme Encoded By The Yeast MIS1 Gene" Biochemistry 32(41):1118-1123 (Abstract Only).

Ye, J. et al. (2012) "Pyruvate Kinase M2 Promotes De Novo Serine Synthesis To Sustain mTORC1 Activity And Cell Proliferation," Proc. Natl. Acad. Sci. (U.S.A.) 109:6904-6909.

Yuan, Z. et al. (1984) "Elementary Steps In The Reaction Mechanism Of Chicken Liver Fatty Acid Synthase. pH Dependence Of NADPH Binding And Isotope Rate Effect For Beta-Ketoacyl Reductase," J. Biol. Chem. 259:6748-6751.

Yuan, J. et al. (2008) "Kinetic Flux Profiling For Quantitation Of Cellular Metabolic Fluxes," Nat. Protoc. 3:1328-1340.

Zhang, W.C. et al. (2012) "Glycine Decarboxylase Activity Drives Non-Small Cell Lung Cancer Tumor-Initiating Cells And Tumorigenesis," Cell 148:259-272.

Zone, W.X. et al. (2016) "Mitochondria and Cancer," Mol. Cell. 61(5):667-676.

\* cited by examiner

Pool Size of 6-Phosphogluconate [pmole/µl cells]

| HEK293T | MDA-MB-468 | iBMK-parental | iBMK-Akt |
|---|---|---|---|
| 23±6 | 16±7 | 12±3 | 15±4 |

(A)            (B)

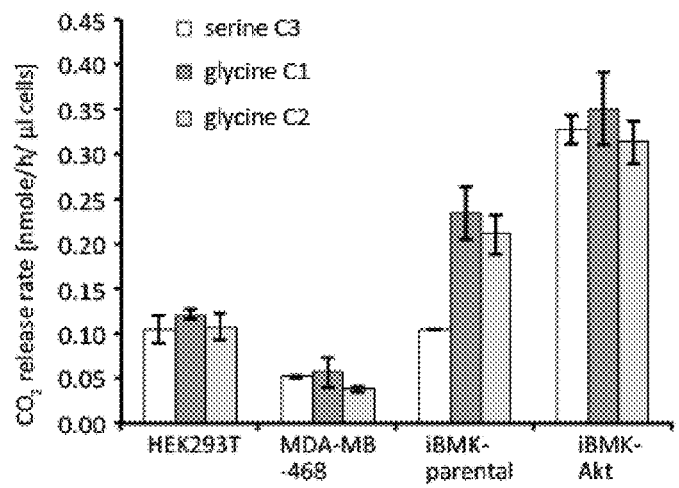
Figure 11D
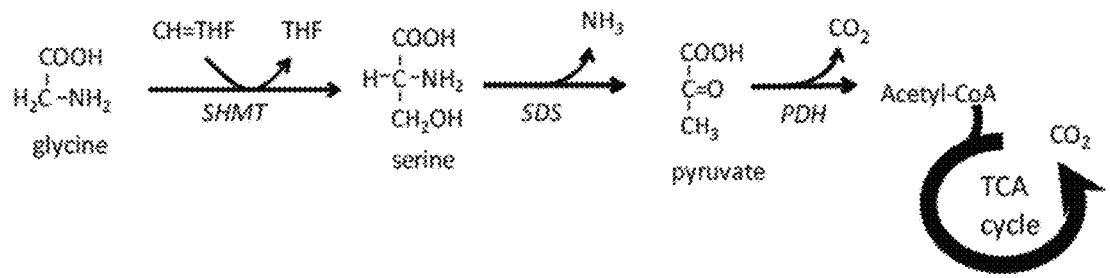
Figure 11E
| Tracer | Fraction of Pyruvate Labeled | | | |
|---|---|---|---|---|
| | HEK293T | MDA-MB-468 | iBMK-parental | iBMK-Akt |
| U-$^{13}$C-serine | <0.5% | <0.5% | <0.5% | <0.5% |
| U-$^{13}$C-glycine | <0.5% | <0.5% | <0.5% | <0.5% |
Figure 11F

Cell Doubling Times

| HEK293T | MDA-MB-468 | iBMK-parental | iBMK-Akt |
|---|---|---|---|
| 22 h | 25 h | 24 h | 21 h |

Cellular Protein Content [µg/µl cells]

| HEK293T | MDA-MB-468 | iBMK-parental | iBMK-Akt |
|---|---|---|---|
| 69±5 | 69±3 | 71±3 | 85±1 |

(A)

(B)

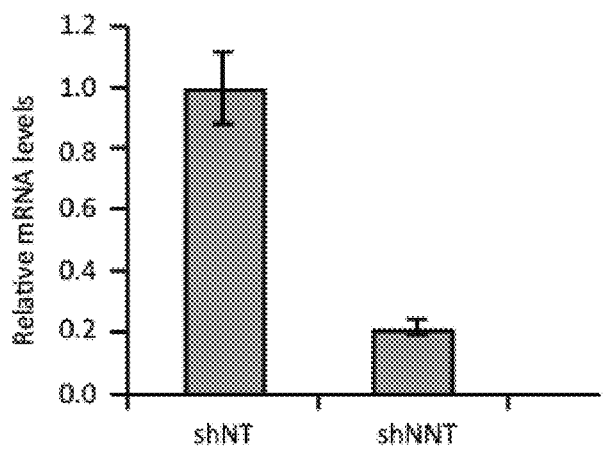
Figure 14D
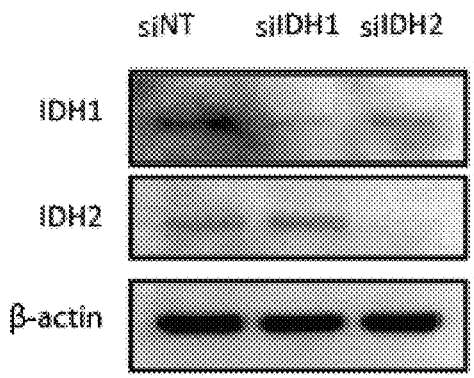
Figure 14E
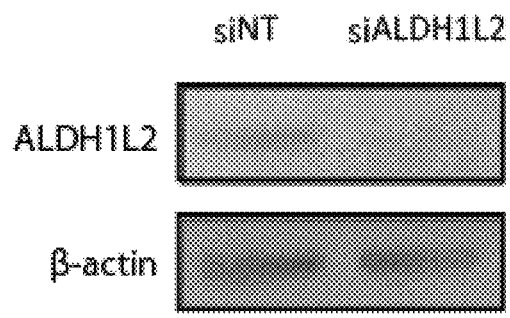
Figure 14F
Cell Doubling Times
| shNT | shG6PD | shMTHFD1 | shMTHFD2 | shME1 | shNNT |
|---|---|---|---|---|---|
| 22 h | 38 h | 35 h | 26 h | 24 h | 22 h |
Figure 14G

| Isotope | Fraction % |
|---|---|
| [M+1]Malate | 10.9 ± 0.2 |
| [M+2]Malate | 1.5 ± 0.1 |
| [M+1]Aspartate | 6.0 ± 0.1 |

Panel A
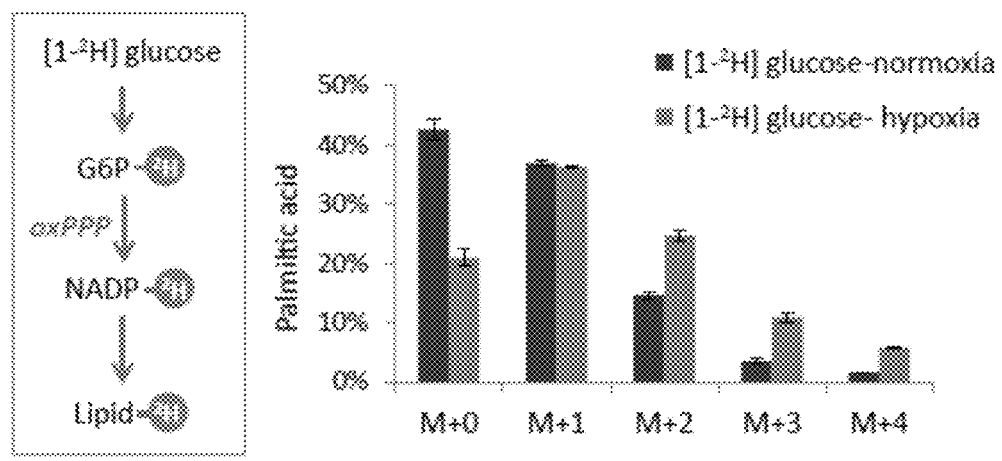
Panel B
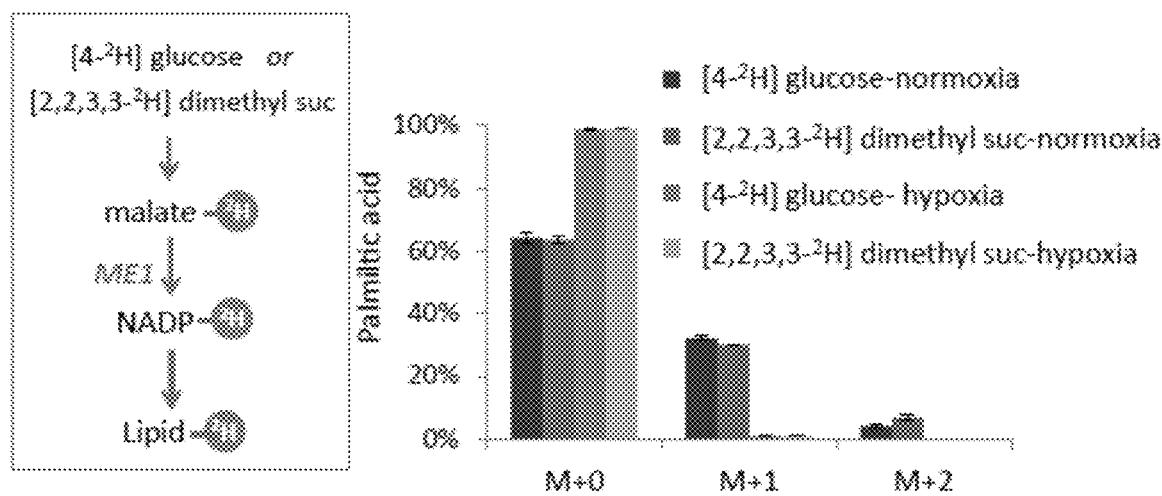
Figure 26, Panels A and B

Panel C
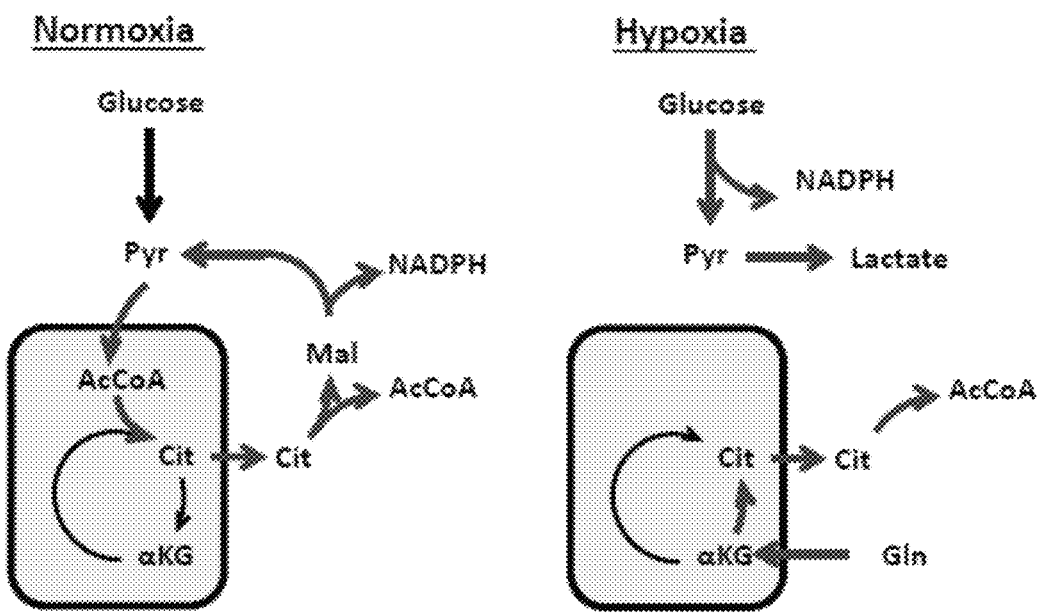
Panel D
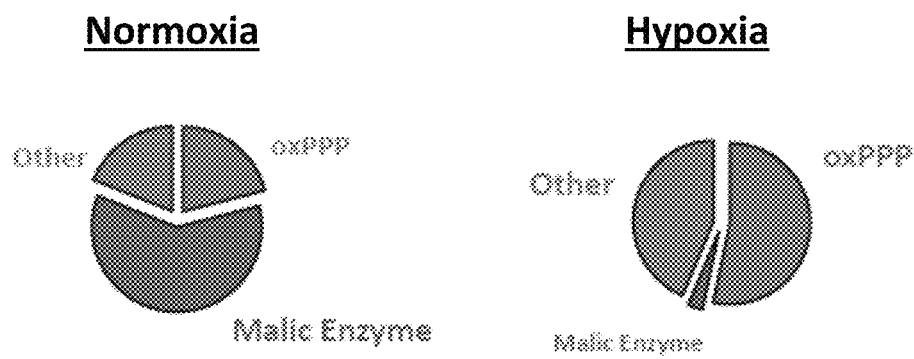
Figure 26, Panels C and D

NADPH PRODUCTION BY THE 10-FORMYL-THF PATHWAY, AND ITS USE IN THE DIAGNOSIS AND TREATMENT OF DISEASE

CROSS-REFERENCE TO RELATED APPLICATIONS

This application claims priority to U.S. Patent Applns. Ser. Nos. 62/219,736 (filed Sep. 17, 2015) and PCT/US2015/021578 (filed Mar. 19, 2015; pending), which application claims priority to U.S. Patent Appln. Ser. No. 61/968,036 (filed Mar. 20, 2014), each of which applications is herein incorporated by reference in its entirety.

STATEMENT REGARDING FEDERALLY SPONSORED RESEARCH OR DEVELOPMENT

This invention was made with government support under Grants No. AI097382, CA163591, and DK019525 awarded by the National Institutes of Health. The government has certain rights in the invention.

REFERENCE TO SEQUENCE LISTING

This application includes one or more Sequence Listings pursuant to 37 C.F.R. 1.821 et seq., which are disclosed in computer-readable media (file name: 1800_0002_CIP_ST25.txt, created on Sep. 15, 2016, and having a size of 2,591 bytes), which file is herein incorporated by reference in its entirety.

BACKGROUND OF THE INVENTION

Field of the Invention

The present invention relates to the recognition of a 10-formyl-THF pathway for producing NADPH, and to the use of that recognition in the diagnosis and treatment of cancer and metabolic disease, in the development of new antineoplastic agents and/or regimens, in the development of new methods for measuring metabolic pathway activity, and in the development of new therapeutics for treating metabolic disease.

Description of Related Art

Humans and other animals derive the energy needed to perform work by recovering chemical energy from ingested foods. Such energy, whether stored as sugar, starch or fat, is ultimately transferred to high-energy compounds for actual use. Adenosine triphosphate ("ATP") is the dominant high-energy compound for, e.g., muscle contraction and neuronal firing). However, an equally important role is played by nicotinamide adenine dinucleotide phosphate ("NADPH"), which powers redox defense and provides the energy needed for biosynthetic reactions (Voet, D. V. et al. (2004) BIOCHEMISTRY (3rd Ed.), John Wiley & Sons). NADPH differs from NADH in the possession of a phosphate group. However, this difference permits the two molecules to have independent regulation and independent functions. Most commonly, NADPH participates in reactions that consume energy in order build up or synthesize larger molecules ("anabolic reactions"); NADH participates in reactions that break down molecules to release energy ("catabolic reactions") (Agledal, L. et al. (2010) "*The Phosphate Makes A Difference: Cellular Functions Of NADP,*" Redox Rep. 15(1):2-10).

ATP is produced both in the cellular cytosol, via the anaerobic conversion of glucose and glycerol to pyruvate ("glycolysis") and in the mitochondria via the aerobic conversion of glucose to water and $CO_2$ ("respiration"). NADPH is most directly produced from glucose in the cytosol via the oxidative pentose phosphate pathway ("oxPPP"); however a portion of the body's NAPDH is produced in both the cytosol and the mitochondria by decarboxylating malate dehydrogenases.

Cells can obtain ATP both from cytosolic and mitochondrial processes, and the relative proportion of cytosolic vs. mitochondrial production of ATP has been found to be correlated with the presence of disease, including cancer, a recognition now referred to as the "Warburg Effect" (Warburg, O. (1956) "*On The Origin Of Cancer Cells,*" Science 123:309-314; Vander Heiden, M. G. et al. (2009) "*Understanding The Warburg Effect: The Metabolic Requirements Of Cell Proliferation,*" Science 324:1029-1033; Razungles, J. et al. (2013) "*[The Warburg Effect: From Theory To Therapeutic Applications In Cancer],*" Med Sci (Paris). (11): 1026-1033; Palsson-McDermott, E. M. et al. (2013) "*The Warburg Effect Then And Now: From Cancer To Inflammatory Diseases,*" Bioessays 35(11):965-973; Jang, M. et al. (2013) "*Cancer Cell Metabolism: Implications For Therapeutic Targets,*" Exp. Molec. Med. 45:e45. doi: 10.1038/emm.2013.85; Nam, S. O. et al. (2013) "*Possible Therapeutic Targets Among The Molecules Involved In The Warburg Effect In Tumor Cells,*" Anticancer Res. 33(7): 2855-2860; Upadhyay, M. et al. (2012) "*The Warburg Effect: Insights From The Past Decade,*" Pharmacol. Ther. 137(3):318-330; Dang, C. V. (2012) "*Links Between Metabolism And Cancer,*" Genes Dev. 26(9):877-890; Ponisovskiy, M. R. (2011) "*Warburg Effect Mechanism As The Target For Theoretical Substantiation Of A New Potential Cancer Treatment,*" Crit. Rev. Eukaryot. Gene. Expr. 21(1):13-28; Fogg, V. C. et al. (2011) "*Mitochondria In Cancer: At The Crossroads Of Life And Death,*" Chin. J. Cancer 30(8):526-539; Dang, C. V. (2011) "*Therapeutic Targeting Of Cancer Cell Metabolism,*" J. Molec. Med. (Berl) 89(3):205-212; Ferreira, L. M. (2010) "*Cancer Metabolism: The Warburg Effect Today,*" Exp. Molec. Pathol. 89(3):372-380; Gogvadze, V. et al. (2009) "*The Warburg Effect And Mitochondrial Stability In Cancer Cells,*" Molec. Aspects Med. 31(1):60-74).

Specifically, most cancer cells actively ferment glucose into lactic acid in the cytosol, thereby producing significantly more ATP via glycolysis than is the case in most normal cells (Alfarouk, K. O. et al. (2011) "*Tumor Acidity As Evolutionary Spite,*" Cancers 3(4):408-414; Gatenby, R. A. et al. (2004) "*Why Do Cancers Have High Aerobic Glycolysis?*" Nature Reviews Cancer 4(11):891-899; Kim, J. W. (2006) "*Cancer's Molecular Sweet Tooth And The Warburg Effect,*" Cancer Res. 66(18):8927-8930). Malignant, rapidly growing tumor cells typically have glycolytic rates up to 200 times higher than those of their normal tissues of origin, even in the presence of oxygen. Research has demonstrated that the Warburg Effect is caused by mutations in oncogenes and tumor suppressor genes.

The Warburg Effect has important medical applications as high aerobic glycolysis by malignant tumors may be used clinically to diagnose and monitor treatment responses of cancers (Lin, G. et al. (2014) "*Current Opportunities And Challenges Of Magnetic Resonance Spectroscopy, Positron Emission Tomography, And Mass Spectrometry Imaging For Mapping Cancer Metabolism in vivo," Biomed. Res. Int. 2014:625095 doi: 10.1155/2014/625095; Boland, M. L. et al. (2013) "Mitochondrial Dysfunction In Cancer," Front. Oncol. 3:292; Witkiewicz, A. K. et al. (2012) "Using The "Reverse Warburg Effect" To Identify High-Risk Breast Cancer Patients: Stromal MCT4 Predicts Poor Clinical Outcome In Triple-Negative Breast Cancers," Cell Cycle 11(6):1108-1117).

Like ATP, NADPH is a critical cofactor for both cellular maintenance and growth. NADPH can be produced in cells by a variety of enzymes including glucose-6-phosphate dehydrogenase (G6PDH) and 6-phosphogluconate dehydrogenase in the pentose phosphate pathway (oxPPP), methylenetetrahydrofolate dehydrogenase (MTHFD) and aldehyde dehydrogenases (ALDH) in folate metabolism, and isocitrate dehydrogenase (IDH) and malic enzyme (ME) associated with the TCA cycle. The oxPPP is localized to the cytosol and is NADPH-specific, while different isozymes of MTHFD, ALDH, ME, IDH are found in cytosol and mitochondria, and may generate NADPH or NADH (Tibbetts, A. S. et al. (2010) "Compartmentalization Of Mammalian Folate-Mediated One-Carbon Metabolism," Annu. Rev. Nutr. 30:57-81; Wise, D. R. et al. (2011) "Hypoxia Promotes Isocitrate Dehydrogenase-Dependent Carboxylation Of A-Ketoglutarate To Citrate To Support Cell Growth And Viability," Proc. Natl. Acad. Sci. (U.S.A.) 108:19611-19616). Among these different enzymes, the importance of the PPP in NADPH production is the best established.

The production of NADPH has also been found to differ in cancer cells relative to normal cells (D'Alessandro, A. et al. (2013) "Proteomics And Metabolomics In Cancer Drug Development," Expert Rev. Proteomics 10(5):473-488; Wen, S. et al. (2013) "Targeting Cancer Cell Mitochondria As A Therapeutic Approach," Future Med. Chem. 5(1):53-67; Dang, C. V. (2012) "Links Between Metabolism And Cancer," Genes Dev. 26(9):877-990; Cui, X. (2012) "Reactive Oxygen Species: The Achilles' Heel Of Cancer Cells?" Antioxid. Redox Signal. 16(11):1212-1214; Stanton, R. C. (2012) "Glucose-6-Phosphate Dehydrogenase, NADPH, And Cell Survival," IUBMB Life 64(5):362-369).

The production of NADPH in oxPPP has been found to be usually high in rapidly proliferating tumor cells (Patra, K. C. et al. (2014) "The Pentose Phosphate Pathway And Cancer," Trends Biochem. Sci. doi.org/10.1016/j.tibs.2014.06.005). Protection against oxidative stress is especially important for cancer cells. Thus, the enhanced production of NADPH in such cells may be a means for protecting cancer cells from oxidative stress. It can also contribute to drug resistance (Irwin, M. E. et al. (2013) "Redox Control Of Leukemia: From Molecular Mechanisms To Therapeutic Opportunities," Antioxid. Redox Signal. 18(11):1349-1383; Bonner, M. Y. et al. (2012) "Targeting NADPH Oxidases For The Treatment Of Cancer And Inflammation," Cell. Mol. Life Sci. 69(14):2435-2442).

An understanding of the routes of ATP production and consumption, first achieved more than a half century ago, has formed the foundation for much of subsequent metabolism research and has provided a means for discriminating between cancer cells and normal cells. (Warburg, O. (1956) "On The Origin Of Cancer Cells," Science 123:309-314). An analogous understanding of the routes of NADPH production and consumption is likewise central to a global understanding of metabolism. The ability to quantitatively analyze NADPH metabolism would thus provide a means for assessing the aggressiveness of a cancer, its amenability to treatment and its responsiveness to a treatment regimen. However, despite all prior work, a need remains for methods suitable for measuring, especially quantitatively, the respective contributions of NADPH production pathways to the total cellular NADPH production. The present invention is directed to these and other goals.

SUMMARY OF THE INVENTION

The present invention relates to the recognition of a 10-formyl-THF pathway for producing NADPH, and to the use of that recognition in the diagnosis and treatment of cancer and metabolic disease, in the development of new antineoplastic agents and/or regimens, in the development of new methods for measuring metabolic pathway activity, and in the development of new therapeutics for treating metabolic disease (Fan, K. et al. (2014) "Quantitative Flux Analysis Reveals Folate-Dependent NADPH Production," Nature 510(7504):298-302, herein incorporated by reference in its entirety).

As indicated above, although the relative contribution of glycolysis and oxidative phosphorylation to ATP production has been extensively analyzed, similar analysis of NADPH metabolism has been lacking. The present invention demonstrates the ability to directly track, by liquid chromatography-mass spectrometry, the passage of deuterium from labeled substrates into NADPH, and in combination with carbon labeling and/or mathematical modeling, permits the measurement of NADPH fluxes. In proliferating cells, the largest contributor to cytosolic NADPH is the oxPPP. Surprisingly, one finding of the present invention is that a nearly comparable contribution can come from serine-driven one-carbon metabolism, where oxidation of methylene-tetrahydrofolate to 10-formyl-tetrahydrofolate is coupled to the reduction of NADP+ to NADPH. Moreover, the tracing of mitochondrial one-carbon metabolism revealed complete oxidation of the one carbon unit to make NADPH.

Since folate metabolism has not previously been considered an NADPH producer, confirmation of its functional significance was undertaken through knockdown of methylene-tetrahydrofolate dehydrogenase (MTHFD) genes. Depletion of either the cytosolic or mitochondrial MTHFD isozyme resulted in decreased cellular ratios of NADPH to NADP+ and GSH to GSSG ratios and increased cell sensitivity to oxidative stress. Thus, while the importance of folate metabolism for proliferating cells has been long recognized and attributed to its function of producing one-carbon units for nucleic acid synthesis, another crucial function of this pathway is generating reducing power. This recognition points to novel therapies for cancer, including regimens that comprise an anti-folate drug and one or more of the classical end products of folate metabolism as rescue agent(s), since provision of such products will not obviate the need of the folate pathway to make NADPH and therefore the anti-folate may retain clinical efficacy despite provision of the classical pathways and products. Such therapies may have superior therapeutic indices, i.e., ratio of therapeutic benefits to side effects, or equivalently cancer specificity, than current treatments.

In detail, the invention provides a method of assessing the suitability of a cancer therapy for a particular cancer patient, wherein the cancer therapy comprises the administration of an anticancer agent, which method comprises:
(A) administering a deuterium-labeled substrate of a biomolecule and the anticancer agent to tumor cells of the patient; and
(B) determining the extent of deuterium labeling of the biomolecule by the tumor cells;

wherein a determination that the rate of the deuterium labeling is elevated relative to that of healthy cells, and is not substantially reduced over the course of the cancer therapy is indicative of the non-suitability of the therapy for the particular patient.

In related embodiments, the invention provides a method of diagnosing a cancer, wherein the method comprises administration of a deuterium-labeled substrate of a biomolecule and monitoring accumulation of the deuterium-labeled product in the tumor. In yet other embodiments, the invention provides a method of monitoring the response of the tumor to an anticancer agent, which method comprises:
(A) administering a deuterium-labeled substrate of a biomolecule to the patient; and
(B) determining the accumulation of the deuterium-labeled product in the tumor, wherein decreasing accumulation of the product in the tumor is indicative of a therapeutic response to the anticancer agent.

In a particular embodiment, the present invention relates to the use of one or more isotope labeled (stable isotope or radiolabeled) tracers of substrates of malic enzyme activity to diagnose and assess disease and therapeutic regimens. The invention particularly concerns the use of the deuterated compounds: 2,2,3,3-$^2$H-dimethyl-succinate or 4-$^2$H-glucose as tracers of malic enzyme in such a method. A finding that deuterium has been incorporated into NADPH or a downstream product thereof at higher or lower levels than in normal cells is indicative of cancer or a metabolic disorder (e.g., obesity, diabetes, etc.), and a finding that the level of deuterium incorporated into NADPH is not normalizing over time during a treatment regimen is indicative of the non-suitability of that treatment regimen for the patient being treated. Conversely, a finding that the level of deuterium incorporated into NADPH is normalizing over time subsequent to the initiation of a treatment regimen for cancer or such metabolic disorder is evidence of the suitability of that therapeutic regimen for that patient.

The invention further provides the embodiment of the above-described method wherein the deuterium-labeled substrate and the anticancer agent are administered to the patient, and wherein the rate of the deuterium labeling is determined in vivo.

The invention further provides the embodiment of the above-described method wherein the deuterium-labeled substrate and the anticancer agent are administered to tumor cells removed from the patient, and wherein the rate of the deuterium labeling is determined in vitro.

The invention further provides the embodiment of the above-described method wherein the anticancer agent is administered to the patient and the deuterium-labeled substrate is administered to tumor cells removed from the patient, and wherein the rate of the deuterium labeling is determined in vitro.

The invention further provides the embodiment of any of the above-described methods wherein the deuterium-labeled substrate is a substrate of a redox-active hydride of NADH and the deuterium-labeled biomolecules comprise the redox-active hydride of NADH.

The invention further provides the embodiment of any of the above-described methods wherein the deuterium-labeled substrate is a substrate of a redox-active hydride of NADPH and the deuterium-labeled biomolecules comprise the redox-active hydride of NADPH.

The invention further provides the embodiment of any of the above-described methods wherein the deuterium-labeled substrate is a substrate of a molecule having a fatty acid moiety and the deuterium-labeled biomolecules comprise the molecule having the fatty acid moiety.

The invention further provides the embodiment of any of the above-described methods wherein the deuterium-labeled substrate is a substrate of a redox-active hydride of NADPH and the deuterium-labeled biomolecules comprise the molecule having the fatty acid moiety.

The invention further provides the embodiment of any of the above-described methods wherein the deuterium-labeled substrate is a substrate of a thymine moiety-containing biomolecule and the deuterium-labeled biomolecules comprise the thymine moiety-containing biomolecule.

The invention further provides the embodiment of any of the above-described methods wherein the cancer therapy comprises inhibiting cytosolic folate metabolism, wherein the deuterium-labeled substrate is a serine molecule that comprises deuteration at serine carbon C-3, and wherein the extent of deuterium labeling of the one or more biomolecules by the tumor cells is determined by measuring the ratio of M+1 to M+2 of deuterated thymine or of a molecule that comprises a deuterated thymine moiety.

The invention further provides the embodiment of any of the above-described methods wherein the inhibition of cytosolic folate metabolism involves treating a patient in need thereof with an inhibitor of the enzyme SHMT1. Suitable inhibitors of the enzyme SHMT1 include compound HK-16, Enantiomer-2 and Enantiomer-1, as well as those provided in U.S. Patent Application Ser. No. 62/131,205, which application is herein incorporated by reference in its entirety, and which disclosure of SHMT1 inhibitors is specifically incorporated by reference herein.

The invention further provides the embodiment of any of the above-described methods wherein the cancer therapy comprises inhibiting mitochondrial folate metabolism, wherein the deuterium-labeled substrate is a serine molecule that comprises deuteration at serine carbon C-3, and wherein the extent of deuterium labeling of the one or more biomolecules by the tumor cells is determined by measuring the ratio of M+1 to M+2 of deuterated thymine or of a molecule that comprises a deuterated thymine moiety.

The invention further provides the embodiment of any of the above-described methods wherein the cancer therapy comprises inhibiting cytosolic folate metabolism, wherein the deuterium-labeled substrate is a serine molecule that comprises deuteration at serine carbon C-3, and wherein the extent of deuterium labeling of the one or more biomolecules by the tumor cells is determined by measuring the production of a $^2$H-labeled fatty acid moiety.

The invention further provides the embodiment of any of the above-described methods wherein the cancer therapy comprises inhibiting mitochondrial folate metabolism, wherein the deuterium-labeled substrate is a serine molecule that comprises deuteration at serine carbon C-3, and wherein the extent of deuterium labeling of the one or more biomolecules by the tumor cells is determined by measuring the production of a $^2$H-labeled fatty acid moiety.

The invention further provides the embodiment of any of the above-described methods wherein the deuterium-labeled substrate is 2,3,3-$^2$H-serine, 3,3-$^2$H-serine or 4-$^2$H-glucose.

The invention further provides the embodiment of any of the above-described methods wherein the extent of deuterium labeling is determined using magnetic resonance imaging (MM).

The invention further provides the embodiment of any of the above-described methods wherein the extent of deuterium labeling is determined using Liquid Chromatography- Mass Spectroscopy (LC-MS), Gas Chromatography-Mass Spectroscopy (GC-MS) or Raman spectroscopy.

The invention further provides the embodiment of any of the above-described methods wherein the anticancer agent is selected from the group consisting of a Non-Specific Chemotherapeutic Agent and a Target Specific Chemotherapeutic Agent.

The invention further provides the embodiment of any of the above-described methods wherein the anticancer agent is an Immunotherapeutic Agent, and is selected from the group consisting of an antibody, a molecule that comprises an epitope-binding fragment of an antibody, and a diabody.

The invention further provides a method of treating cancer in a cancer patient, wherein the method comprises administering to the cancer patient a pharmaceutical composition comprising:
(A) an anti-folate anticancer agent; and
(B) one or more metabolic compounds selected from the group consisting of thymine, a molecule that comprises a thymine moiety, formate, a molecule that comprises a formate moiety, glycine and a purine; and
(C) a pharmaceutically acceptable excipient, carrier or diluent;
wherein the composition contains the anti-folate anticancer agent in an amount sufficient to treat the cancer and contains the metabolic compound(s) in amount(s) sufficient to remediate attenuation of the concentration of the metabolic compound(s) by the anti-folate anticancer agent or to increase the efficiency of said anti-folate anticancer agent or attenuate an adverse side effect caused by the administered anti-folate anticancer agent.

The invention further provides the embodiment of such method wherein the one or more metabolic compounds is thymidine.

The invention further provides the embodiment of all such methods, wherein the tumor cells are tumor cells of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

BRIEF DESCRIPTION OF THE DRAWINGS

FIG. 1A provides an oxPPP pathway schematic diagram. FIG. 1B shows mass spectra of NADPH (FIG. 1B, Panel (A)) and NADP+ (FIG. 1B, Panel (B)) from cells labeled with 1-$^2$H-glucose (iBMK-parental cells, 20 min). FIG. 1C shows the kinetics of NADPH labeling from 1-$^2$H-glucose (iBMK-parental cells). FIG. 1D shows NADPH labeling from 1-$^2$H-glucose (20 min). FIG. 1E shows that 1-$^2$H-glucose and 3-$^2$H-glucose yield similar NADPH labeling (iBMK-parental cells, 20 min). Substrate labeling is reported for glucose-6-phosphate for 1-$^2$H-glucose and 6-phosphogluconate for 3-$^2$H-glucose. FIG. 1F provides a schematic illustrating that the total cytosolic NADP+ reduction flux is the absolute oxPPP flux (measured based on $^{14}CO2$ excretion) divided by the fractional oxPPP contribution (measured based on NADPH $^2$H-labeling). FIG. 1G shows OxPPP flux based on difference in 14C—CO2 release from 1-$^{14}$C- and 6-$^{14}$C-glucose. FIG. 1H shows total cytosolic NADP+ reduction flux. All results are mean±SD, N≥2 biological replicates from a single experiment and were confirmed in multiple experiments.

FIG. 2A shows canonical NADPH production pathways. FIG. 2B shows NADPH and NADP+ isotopic distribution (without correction for natural isotope abundances) after incubation with 2,3,3,4,4-$^2$H-glutamine tracer to probe NADPH production via glutamate dehydrogenase and malic enzyme (HEK293T cells, 20 min). See also FIGS. 8A-8H. FIG. 2C shows NADPH and NADP+ isotopic distribution as in FIG. 2B using 2,3,3-$^2$H-aspartate tracer to probe NADPH production via IDH. See also FIGS. 8A-8H. FIG. 2D shows NADPH production routes predicted by experimentally-constrained genome-scale flux balance analysis. FIG. 2E shows NADPH and NADP+ isotopic distribution as in FIG. 2B using 2,3,3-$^2$H-serine tracer to probe NADPH production via folate metabolism (no glycine in the media). See also FIGS. 9A-9D. FIG. 2F shows the relative NADPH to NADP+ ratio in HEK293T cells with knockdown of various potential NADPH-producing enzymes: glucose-6-phosphate dehydrogenase (G6PD), cytosolic malic enzyme (ME1), cytosolic and mitochondrial isocitrate dehydrogenase (IDH1 and IDH2), transhydrogenase (NNT), and cytosolic and mitochondrial methylenetetrahydrofolate dehydrogenase (MTHFD1 and MTHFD2). Plotted ratios are relative to vector control knockdown. Results are mean±SD, N≥2 biological replicates from a single experiment and were confirmed in multiple experiments.

FIG. 3A shows a pathway schematic depicting the role played by serine and glycine in NADPH production. FIG. 3B shows the glycine and ATP labeling pattern after incubation with U-$^{13}$C-glycine (HEK293T cells, 24 h). The lack of M+3 and M+4 ATP indicates that no glycine-derived one-carbon units contributed to purine synthesis. FIG. 3C shows the fraction of NADPH labeled at the redox-active hydrogen after 24 h incubation with 2,3,3-$^2$H-serine in HEK293T cells with stable MTHFD1 or MTHFD2 knockdown. The same cells were used also in FIGS. 3F-3I. FIG. 3D shows the absolute rate of cytosolic folate-dependent NADPH production. FIG. 3E shows the $CO_2$ release rate from glycine C1 and glycine C2. FIG. 3F shows the GSH/GSSG ratio. FIG. 3G shows the relative growth, normalized to untreated samples, during 48 h exposure to $H_2O_2$. FIG. 3H shows the fractional death observed after 24 h exposure to 250 μM $H_2O_2$. FIG. 3I shows the fractional death observed after 24 h exposure to 300 μM diamide. FIG.

3J shows the relative reactive oxygen species ("ROS") levels measured using DCFH assay. Mean±SD, N=3.

Figure 4A:
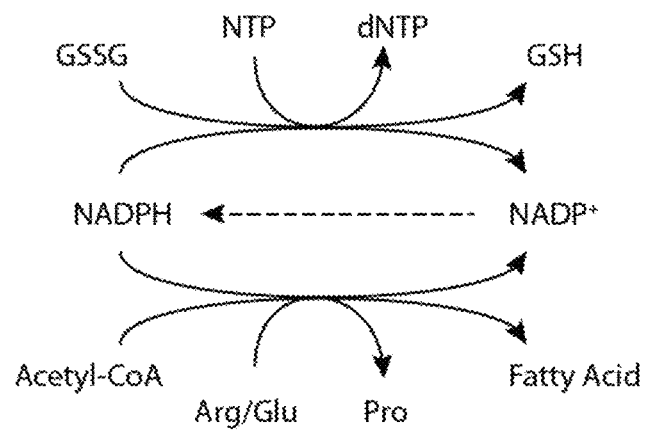
Figure 4B:
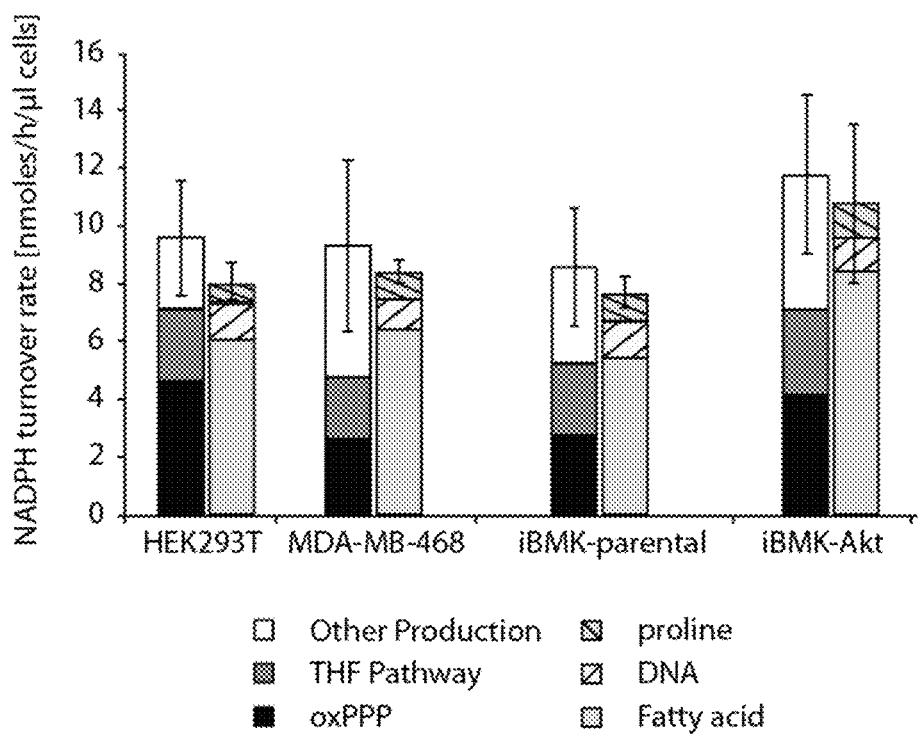

FIGS. 4A-4B show a comparison of NADPH production and consumption. FIG. 4A shows the major NADPH consumption pathways. FIG. 4B shows cytosolic NADPH production and consumption fluxes. Mean±SD, with error bar showing the variation of total production or consumption, N=3.

Figure 5A:
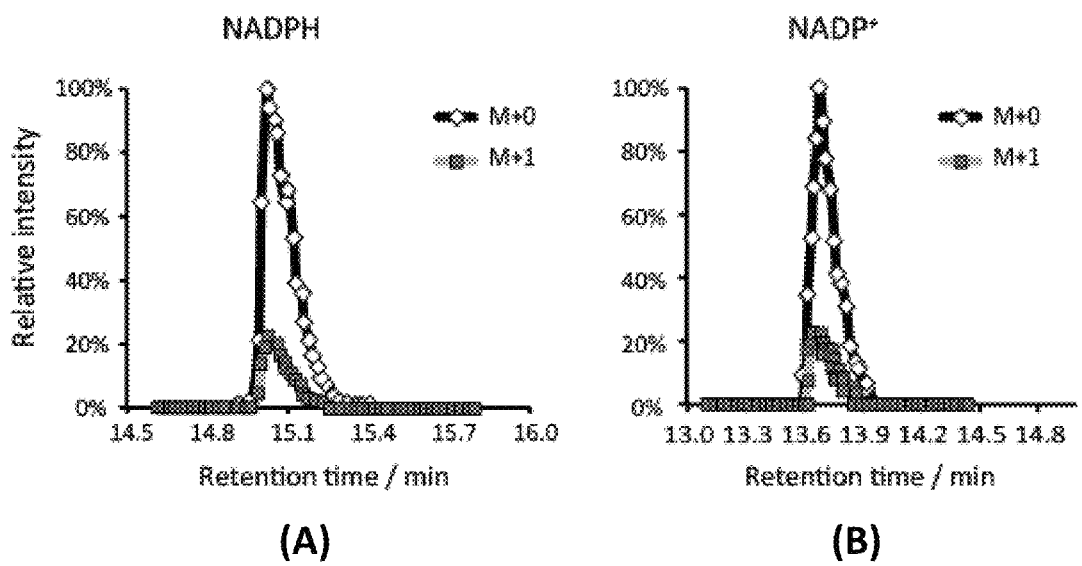
Figure 5B:
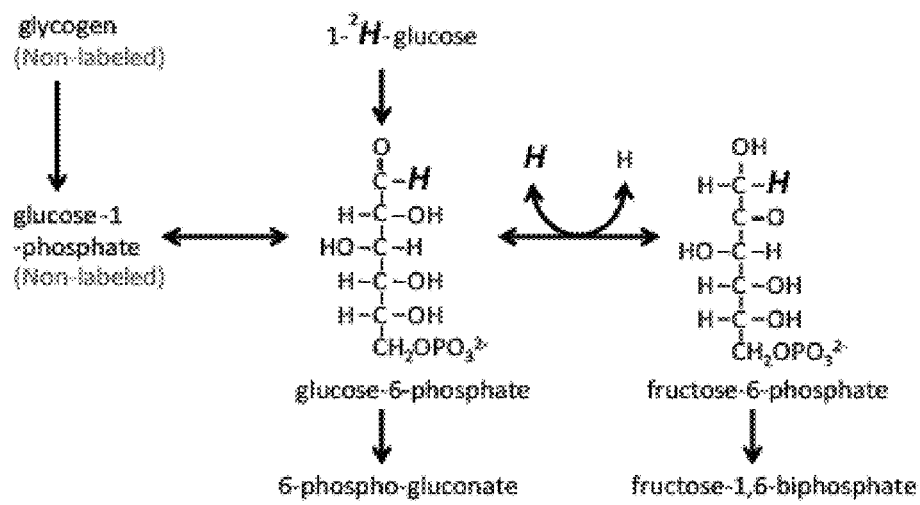
Figure 5C:
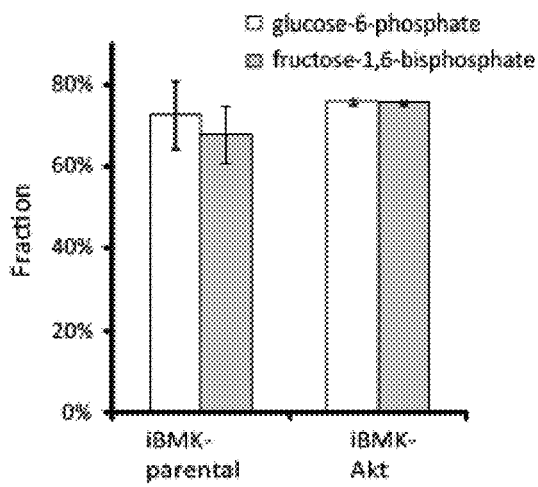
Figure 5D:
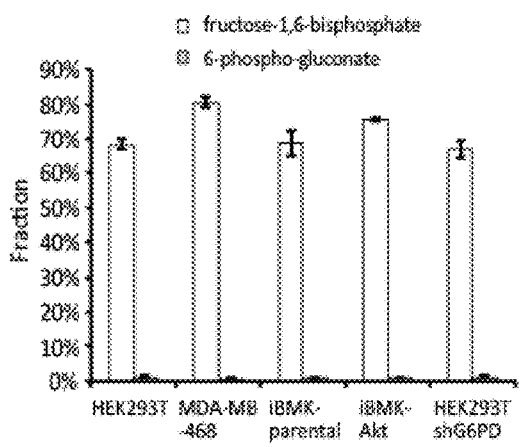
Figure 5E:
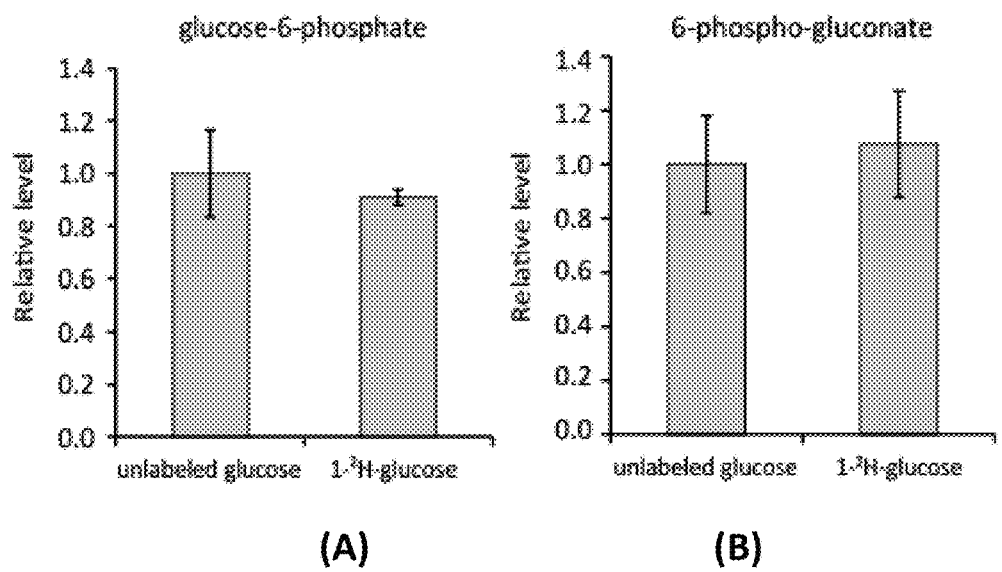
Figure 5F:
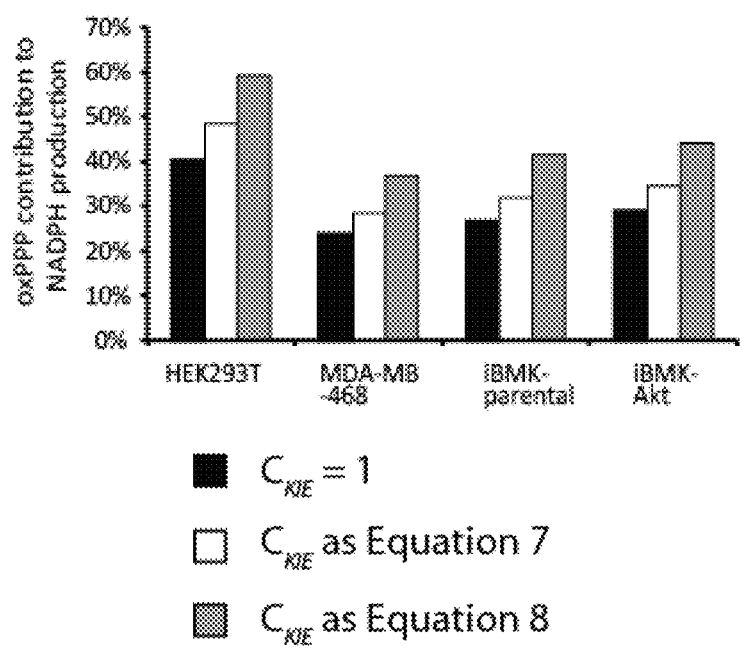
Figure 5G:
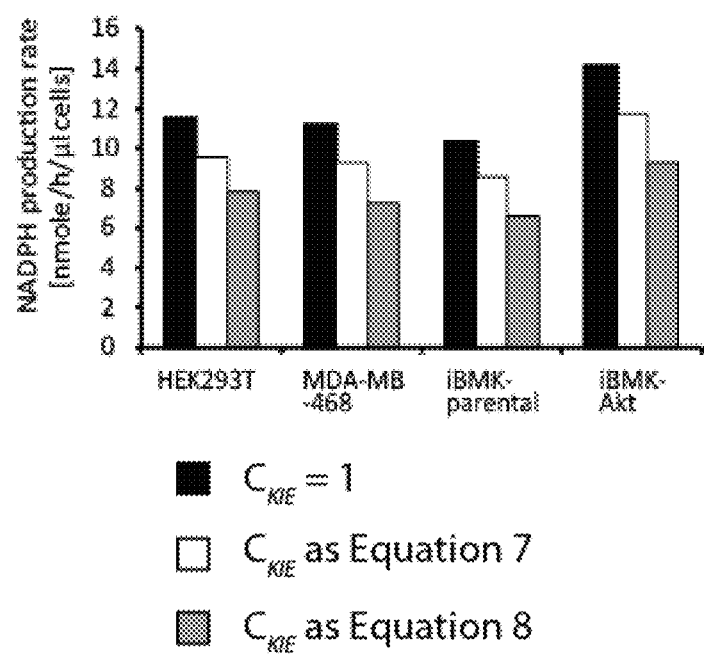

FIGS. 5A-5G probe the fractional contribution of the oxPPP to NADPH production with $^2$H-glucose. FIG. 5A shows an example of LC-MS chromatogram of M+0 and M+1 forms of NADPH (FIG. 5A, Panel (A)) and NADP+ (FIG. 5A, Panel (B)) Plotted values are 5 ppm mass window around each compound. FIG. 5B shows that the extent of NADPH labeling should be corrected for the extent of glucose-6-phosphate labeling. Incomplete labeling can occur due to influx from glycogen or $^1$H/$^2$H ("H/D") exchange. FIG. 5C shows the labeling fraction of glucose-6-phosphate and fructose-1,6-phosphate in iBMK cells with and without activated Akt (20 min after switching into 1-$^2$H-glucose). FIG. 5D shows the labeling fraction of fructose-1,6-phosphate and 6-phosphogluconate after feeding 1-$^2$H-glucose. The labeling fraction of fructose-1,6-phosphate reflects the labeling of glucose-6-phosphate, whose peak after addition of the $^2$H-glucose was not sufficiently resolved from other LC-MS peaks in HEK293T and MDA-MB-468 cells to allow precise quantitation of its labeling directly. The difference in the labeling fraction between glucose-6-phosphate and 6-phosphogluconate reflects the fraction of deuterium labeling specifically at position 1 of glucose-6-phosphate. FIG. 5E shows that due to the kinetic isotope effect, feeding of deuterium tracer can potentially alter pathway fluxes. To assess whether the feeding of 1-$^2$H-glucose creates a bottleneck in the oxPPP, the relative concentration of oxPPP intermediates glucose-6-phosphate (FIG. 5E, Panel (A)) and 6-phospho-gluconate (FIG. 5E, Panel (B)) with or without feeding of 1-$^2$H-glucose was measured. No significant changes were observed. FIG. 5F shows the impact of different mechanisms of correcting for the deuterium kinetic isotope effect on fractional contribution of oxPPP to NADPH production. FIG. 5G shows the impact of different mechanisms of correcting for the deuterium kinetic isotope effect on calculated total NADPH production rate. The correction mechanisms are: (i) no kinetic isotope effect ($C_{KIE}$=1), (ii) no impact on total pathway flux but preferential utilization of $^1$H over $^2$H-labeled substrate (Equation 7) (the smallest reasonable correction, and the one applied herein, where not otherwise indicated), or (iii) full kinetic isotope effect observed for the isolate enzyme with associated decrease in total pathway flux (Equation 8) (the largest reasonable correction). All results are mean±SD, N≥2 biological replicates from a single experiment and were confirmed in multiple experiments.

Figure 6A:
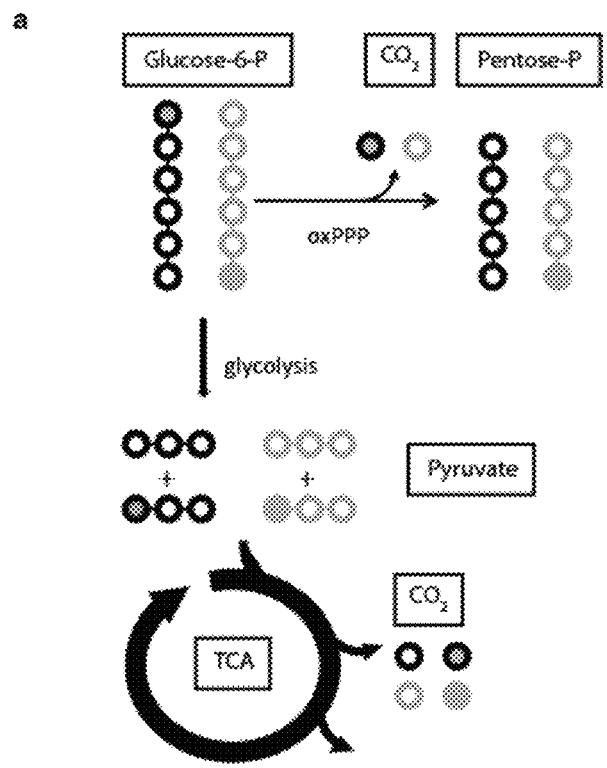
Figure 6B:
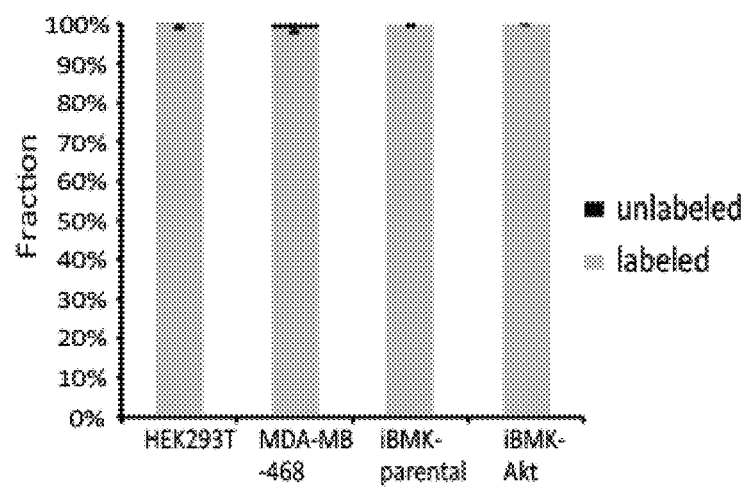
Figures 6C, 6D:
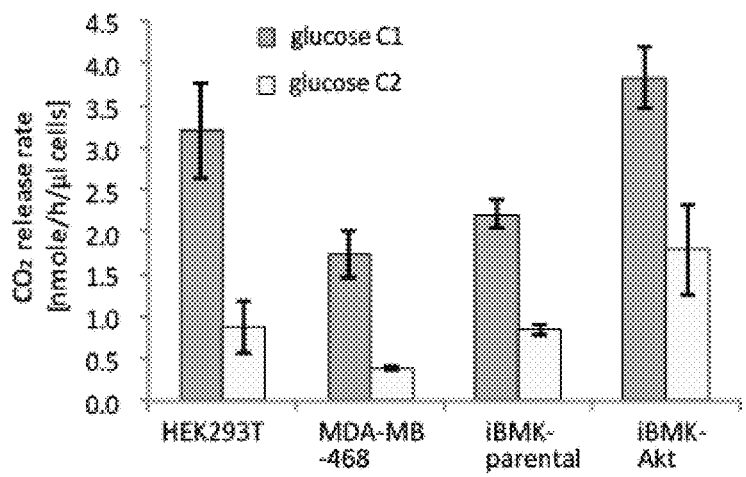
Figure 6E:
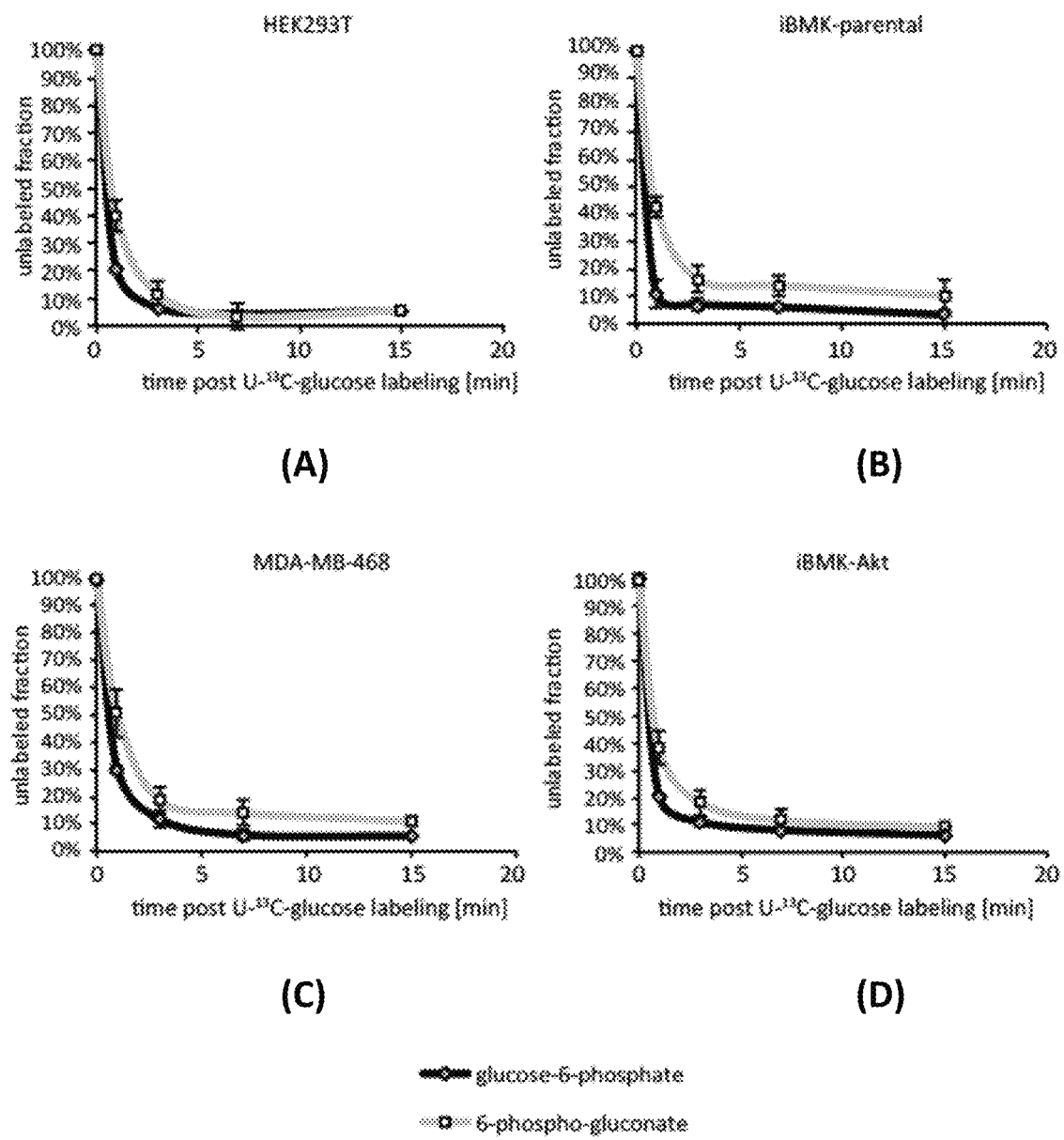
Figure 6F:
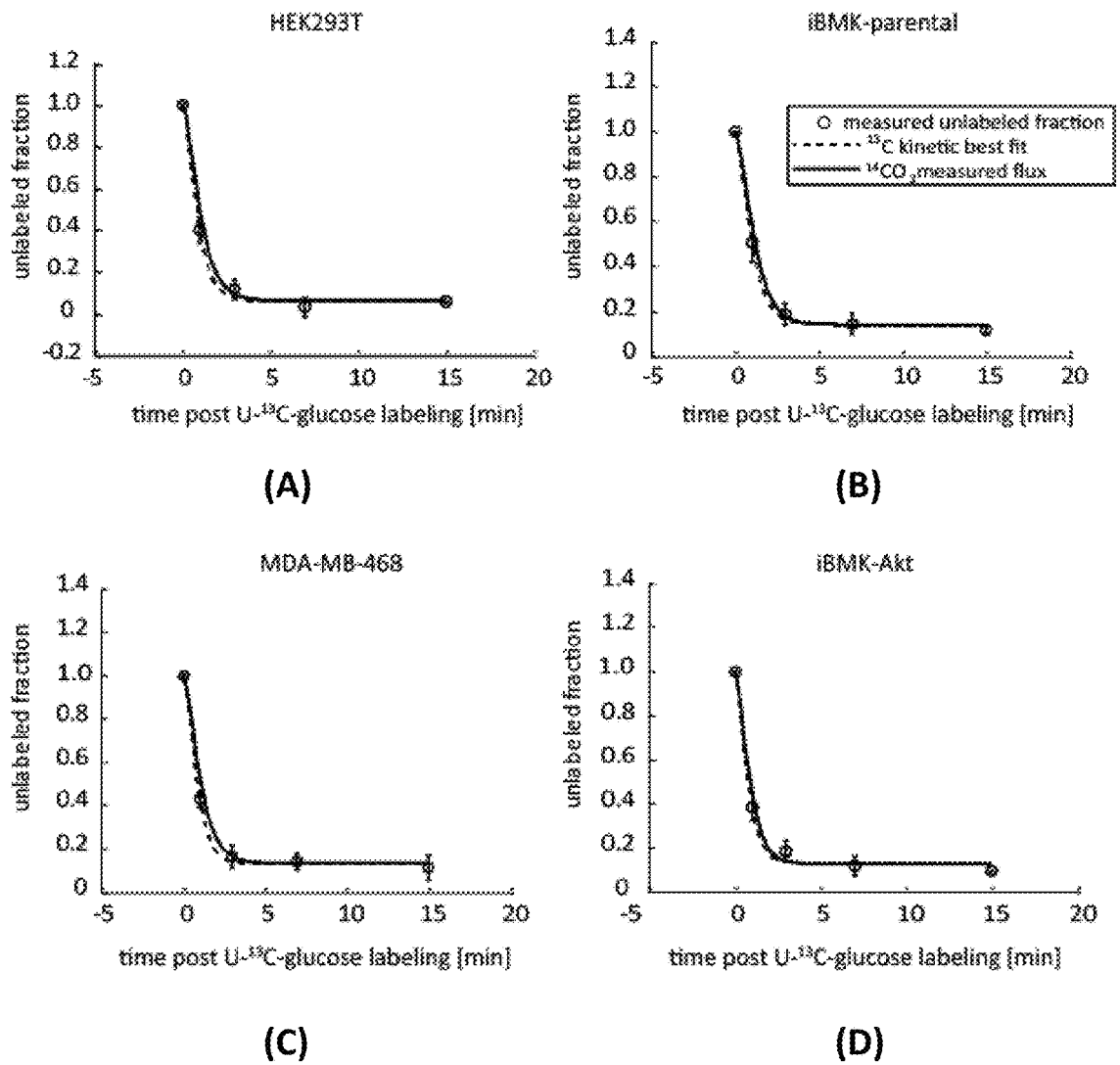
Figure 6G:
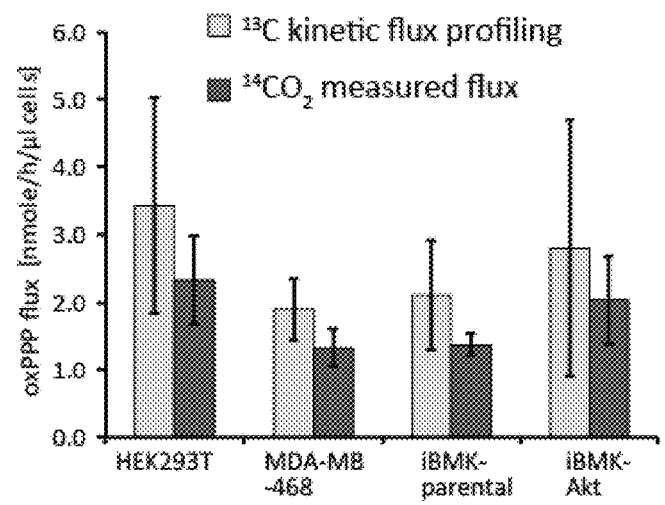

FIGS. 6A-6G show that two independent measurement methods give consistent oxPPP fluxes. FIG. 6A provides a diagram of 1-$^{14}$C-glucose and 6-$^{14}$C-glucose metabolism through glycolysis and the pentose phosphate pathway. The oxPPP specifically releases glucose C1 as $CO_2$, whereas all other $CO_2$-releasing reactions are downstream of triose phosphate isomerase (TPI). As TPI renders C1 and C6 of glucose indistinguishable (both positions become C3 of glyceraldehyde-3-phosphate), the difference in $CO_2$ release from C1 versus C6, multiplied by two, gives the absolute rate of NADPH production via oxPPP. A potential complication involves carbon scrambling via the reactions of the non-oxidative PPP, but this was insignificant (see FIGS. 7A-7F). FIG. 6B shows the complete carbon labeling of glucose-6-phosphate. Glucose-6-phosphate labeled completely (>99%) within 2 h of switching cells into U-$^{13}$C-glucose. FIG. 6C shows the $CO_2$ release rate from 1-$^{14}$C-glucose and 6-$^{14}$C-glucose. FIG. 6D shows the pool size of 6-phosphogluconate. FIG. 6E (Panels A-D) shows the kinetics of glucose-6-phosphate and 6-phosphogluconate labeling upon switching cells to U-$^{13}$C-glucose. FIG. 6F, Panels A-D shows an overlay upon the 6-phosphogluconate data from FIG. 6E of simulated labeling curves based on the flux that best fits the labeling kinetics (dashed) and the flux from $^{14}CO_2$ release measurements (solid). FIG. 6G shows the calculated fluxes and 95% confidence intervals based on the kinetics of 6-phosphogluconate labeling from U-$^{13}$C-glucose, compared to radioactive $CO_2$ release from 1-$^{14}$C-glucose and 6-$^{14}$C-glucose. The two approaches give consistent results, with the $^{14}CO_2$ release data being more precise. Mean+SD, N=3.

Figure 7A:
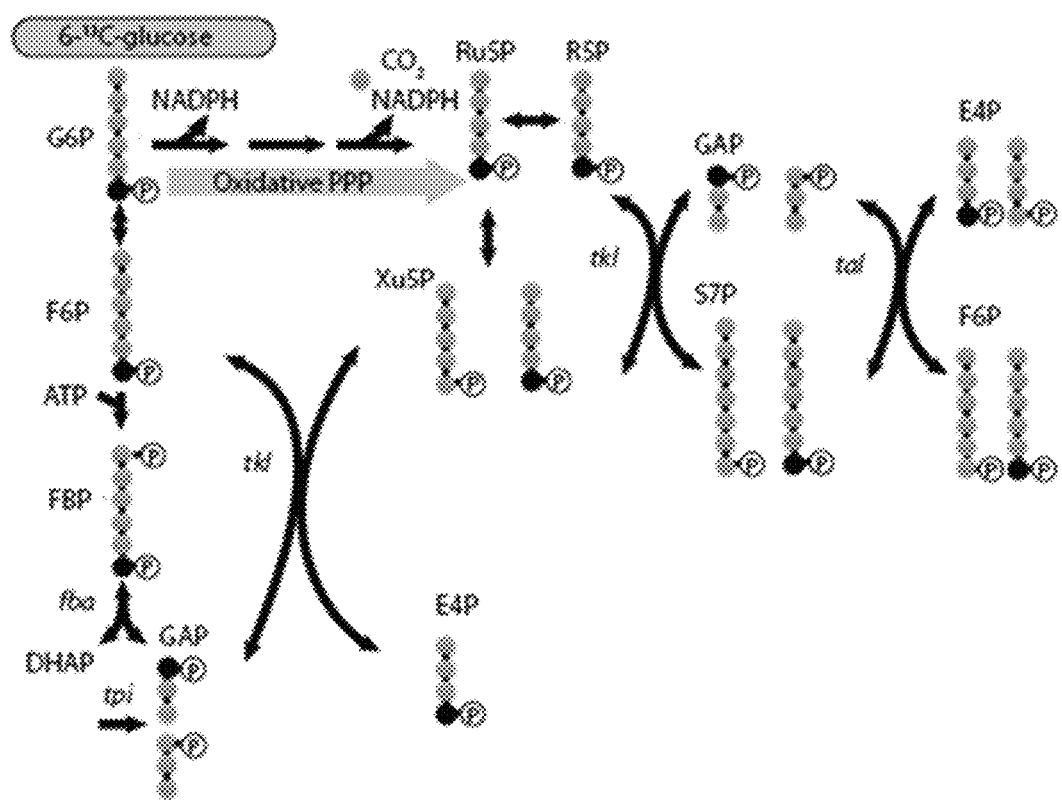
Figure 7B:
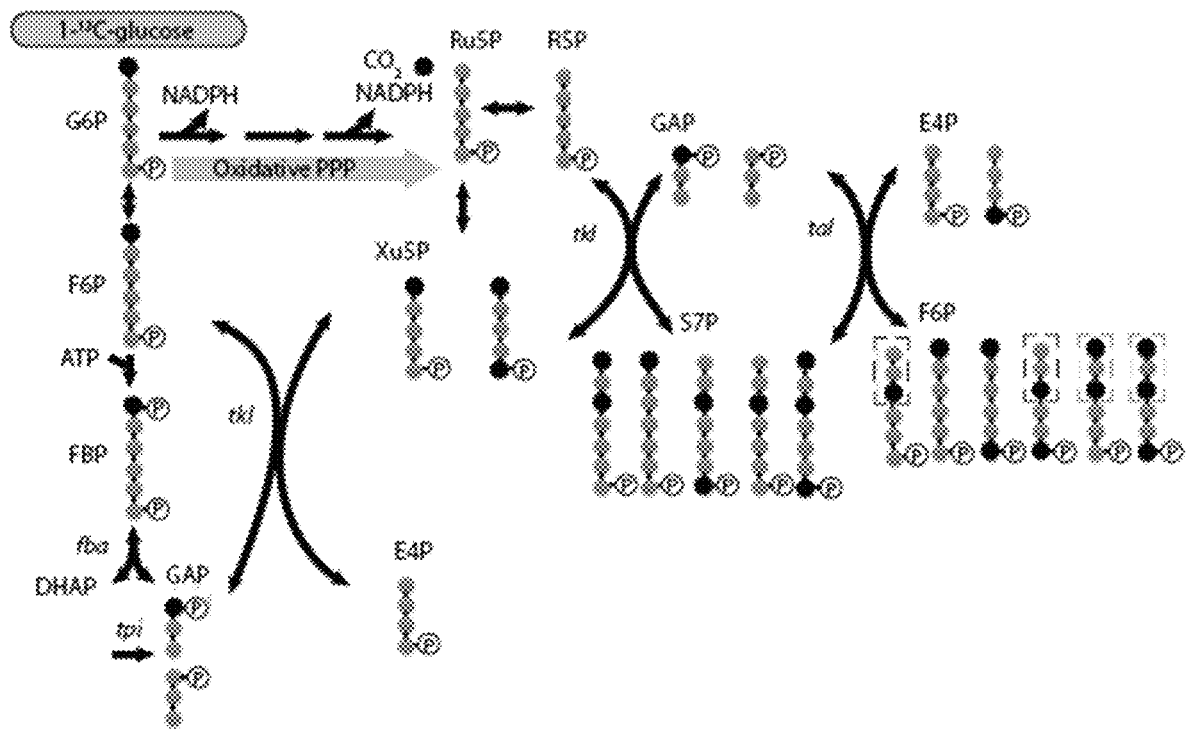
Figure 7C:
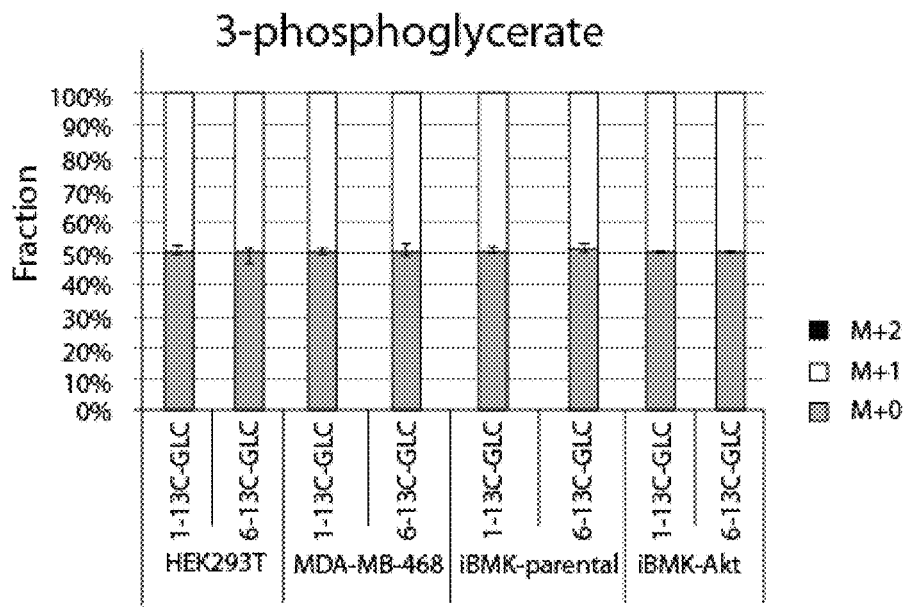
Figure 7D:
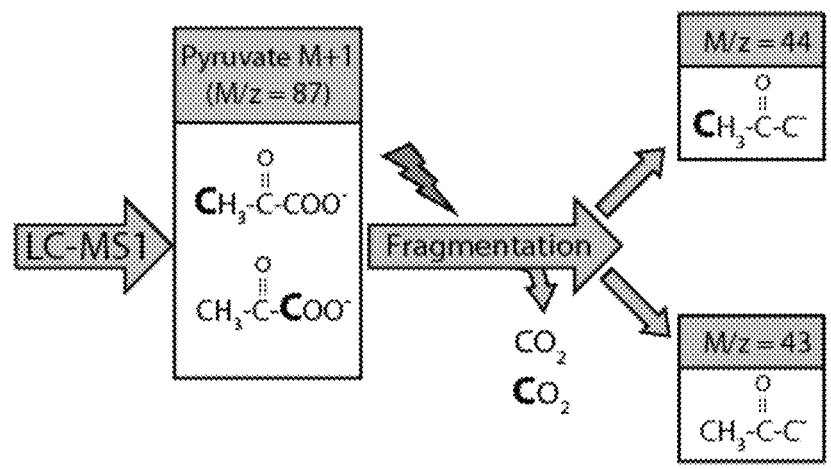
Figure 7E:
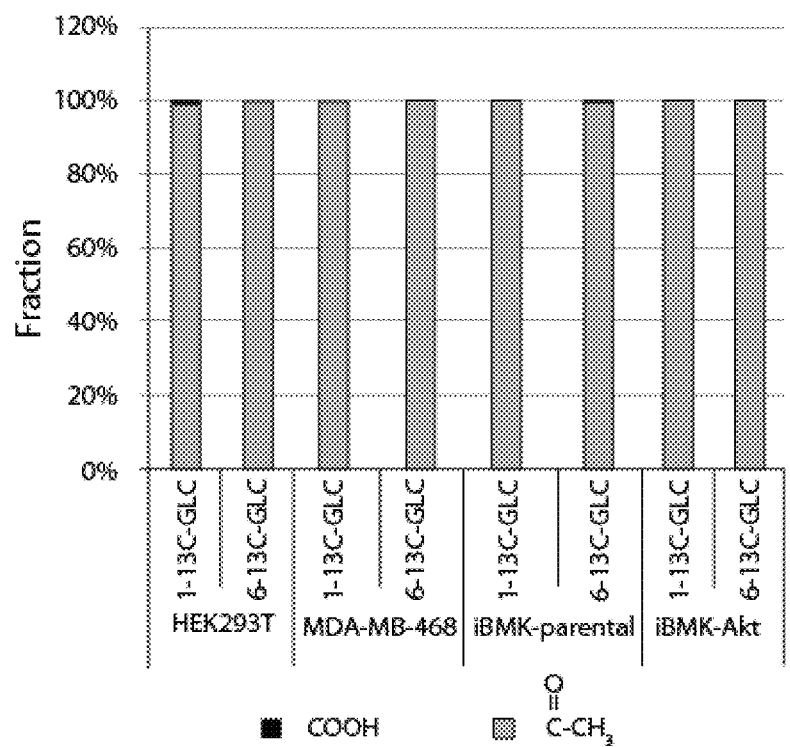
Figure 7F:
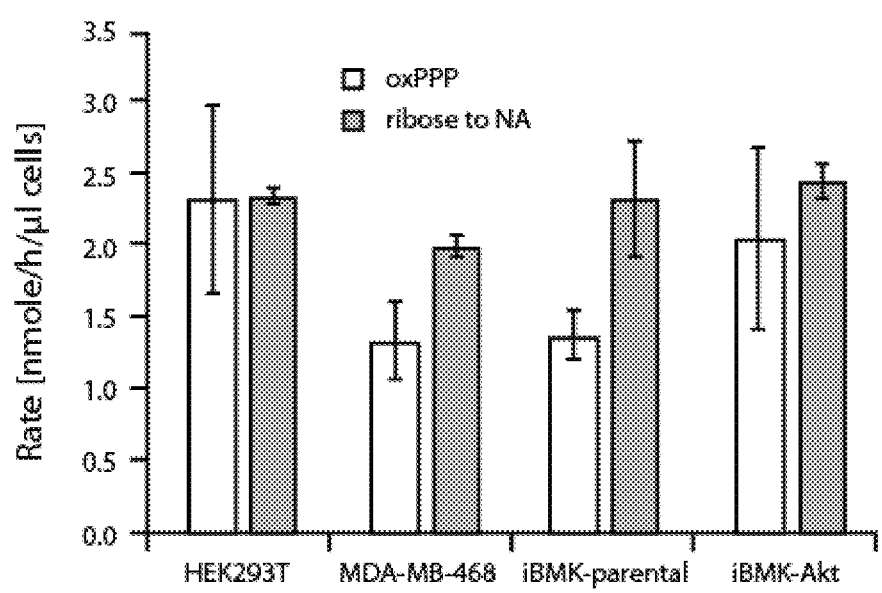

FIGS. 7A-7F show the extent of carbon scrambling via non-oxPPP is insufficient to impact substantially oxPPP flux determination using 1-$^{14}$C and 6-$^{14}$C-glucose, with most carbon entering oxPPP directed towards nucleotide synthesis. FIG. 7A provides a schematic of glycolysis and PPP showing fate of glucose C6. Note that glucose C6 occupies the phosphorylated position (i.e., the last carbon) in every intermediate. Thus, upon catabolism to pyruvate, glucose C6 always becomes pyruvate C3, irrespective of any potential scrambling reactions. FIG. 7B provides a schematic of glycolysis and PPP showing the fate of glucose C1. Glucose C1 can be scrambled via the non-oxPPP, moving to C3 (black dashed boxes) or C6, as shown in the Figure. The forms shown in the gray dashed boxes were not experimentally observed. As glucose C3 becomes pyruvate C1 (the carboxylic acid carbon of pyruvate), which is selectively released as $CO_2$ by pyruvate dehydrogenase, scrambling of C1 to C3 can potentially increase $CO_2$ release from glucose C1 relative to C6. This is ruled out in FIG. 7D and FIG. 7E. FIG. 7C shows that feeding 1-$^{13}$C-glucose or 6-$^{13}$C-glucose results in 50% labeling of 3-phosphoglycerate without any double labeling (i.e., M+2), as expected in the absence of scrambling. FIG. 7D shows the use of the MS/MS method to analyze positional labeling of 1-labeled pyruvate. Collision induced dissociation breaks pyruvate to release the carboxylic acid group as $CO_2$. If the daughter peak of 1-labeled pyruvate does not contain labeled carbon (M/z=43), the labeling is at the C1 position; otherwise, it is at C2 or C3. FIG. 7E shows that after feeding 1-$^{13}$C-glucose or 6-$^{13}$C-glucose, pyruvate is not labeled at the C1 position (<0.5%), ruling out extensive scrambling. FIG. 7F shows that the OxPPP flux is similar to or smaller than ribose demand for nucleotide synthesis. Mean+SD, N=3.

Figure 8A:
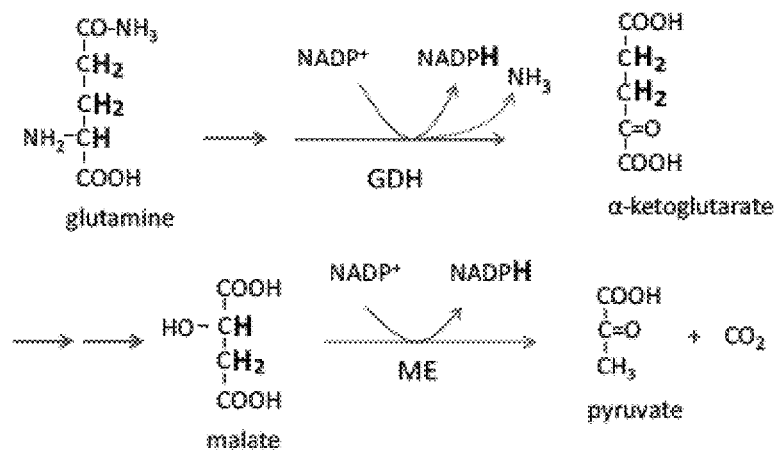
Figure 8B:
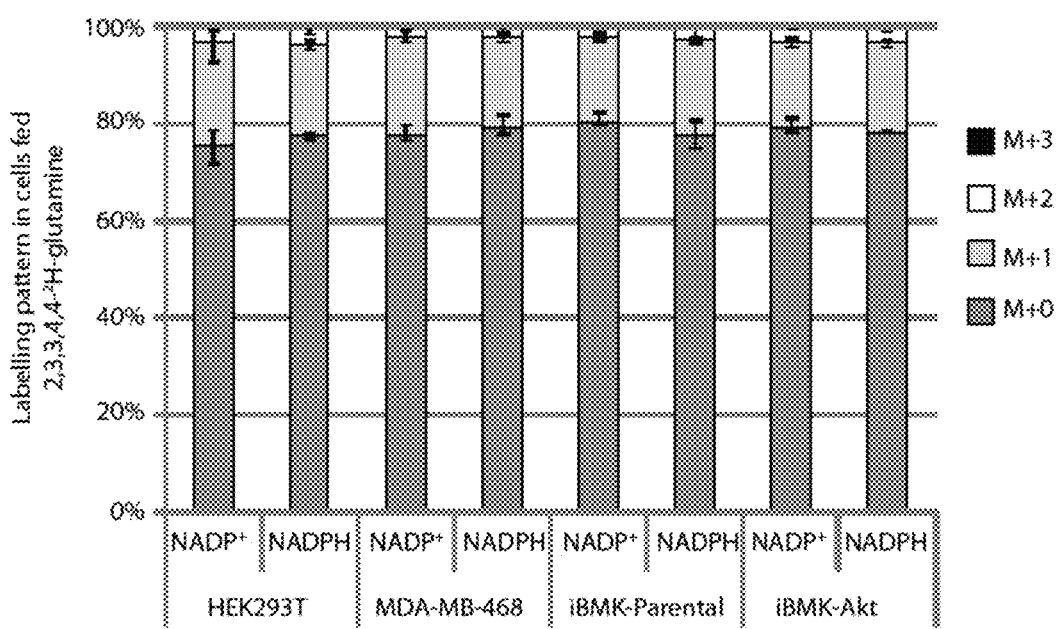
Figure 8C:
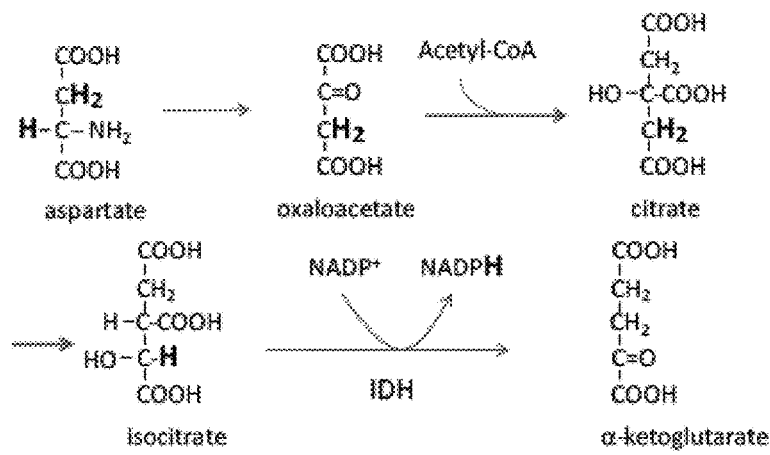
Figure 8D:
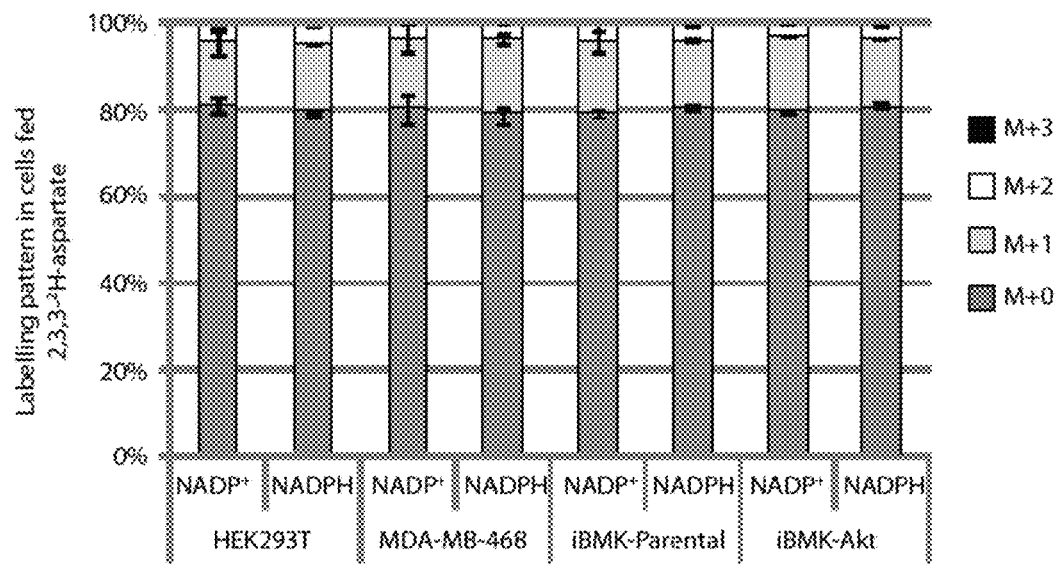

FIGS. 8A-8H probe the contribution of alternative NADPH-producing pathways. FIG. 8A provides a pathway diagram showing the potential for 2,3,3,4,4-$^2$H-glutamine to label NADPH via glutamate dehydrogenase and via malic enzyme. Labeled hydrogens are shown in bold. FIG. 8B shows NADP+ and NADPH labeling patterns (without correction for natural 13C-abundance) after 48 h incubation with 2,3,3,4,4-$^2$H-glutamine. The indistinguishable labeling of NADP+ and NADPH implies lack of NADPH redox-active hydrogen labeling. FIG. 8C provides a pathway diagram showing the potential for 2,3,3-$^2$H-aspartate to label NADPH via isocitrate dehydrogenase. FIG. 8D shows NADP+ and NADPH labeling patterns (without correction for natural $^{13}$C-abundance) after 48 h incubation with 2,3,3-$^2$H-aspartate. The indistinguishable labeling of NADP+ and NADPH implies lack of redox-active hydrogen labeling.

Figure 8E:
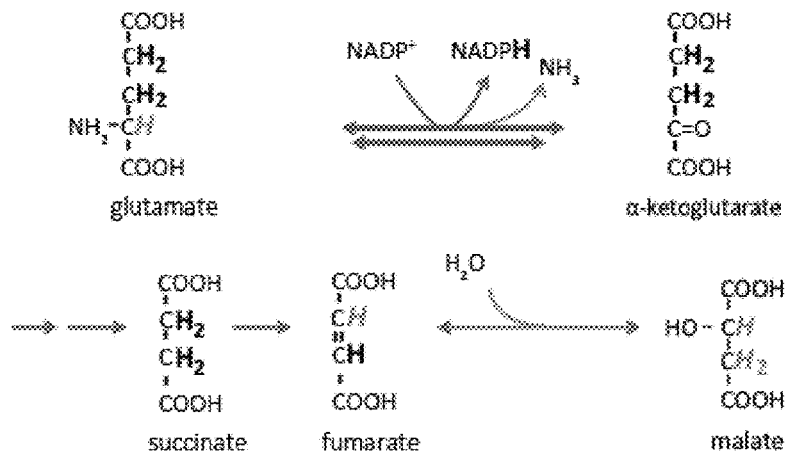
Figure 8F:
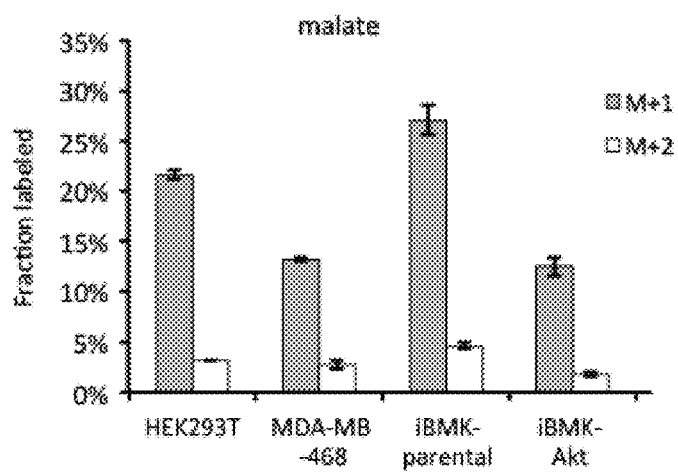
Figure 8G:
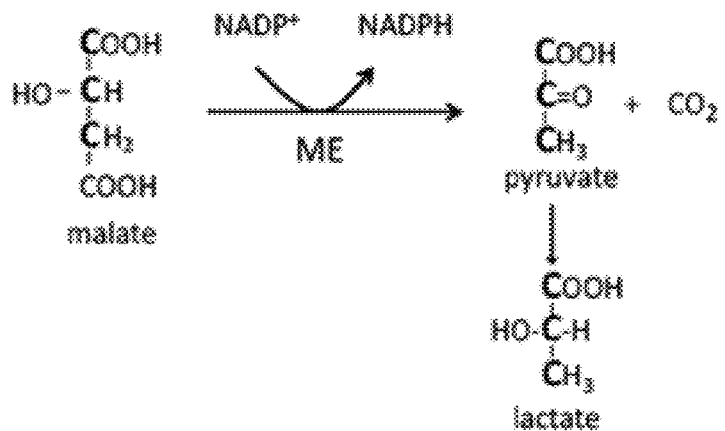
Figure 8H:
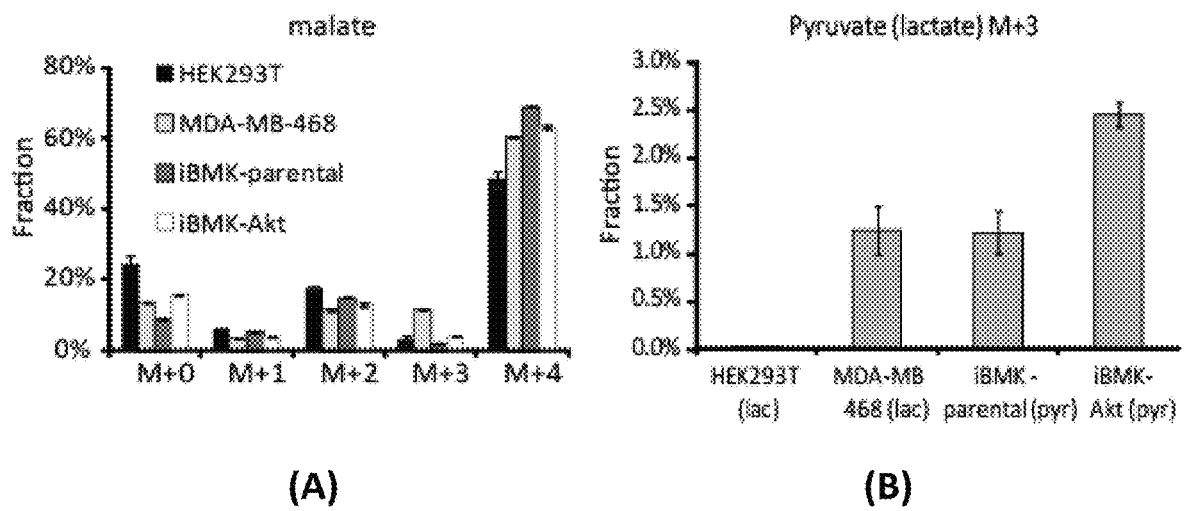

Lack of detectable labeling may be due to insufficient substrate labeling or H/D exchange. FIG. 8E provides a diagram of 2,3,3,4,4-$^2$H-glutamine metabolism through TCA cycle, tracing labeled hydrogen. Hydrogen atoms shown in lighter shade indicate potential H/D exchange with water. FIG. 8F shows the malate labeling fraction after cells were fed 2,3,3,4,4-$^2$H-glutamine for 48 h. FIG. 8G provides a pathway diagram showing the potential for 1,2,3-$^{13}$C-malate (made by feeding U-$^{13}$C-glutamine) to label pyruvate and lactate via malic enzyme. FIG. 8H shows the extent of malate (FIG. 8H (Panel (A)) and pyruvate/lactate (FIG. 8H (Panel (B)) $^{13}$C-labeling. Cells were incubated with U-$^{13}$C-glutamine for 48 h. M+3 pyruvate indicates malic enzyme flux, which may generate either NADH or NADPH. Similar results were also obtained for M+3 lactate (which was used as a surrogate for pyruvate, in cases where lactate was better detected). The corresponding maximal possible malic enzyme-driven NADPH production rate ranges, depending on the cell line, from <2 nmol µL-1 h-1 to 6 nmol µL-1 h-1. Mean±SD, N≥2.

Figure 3A:
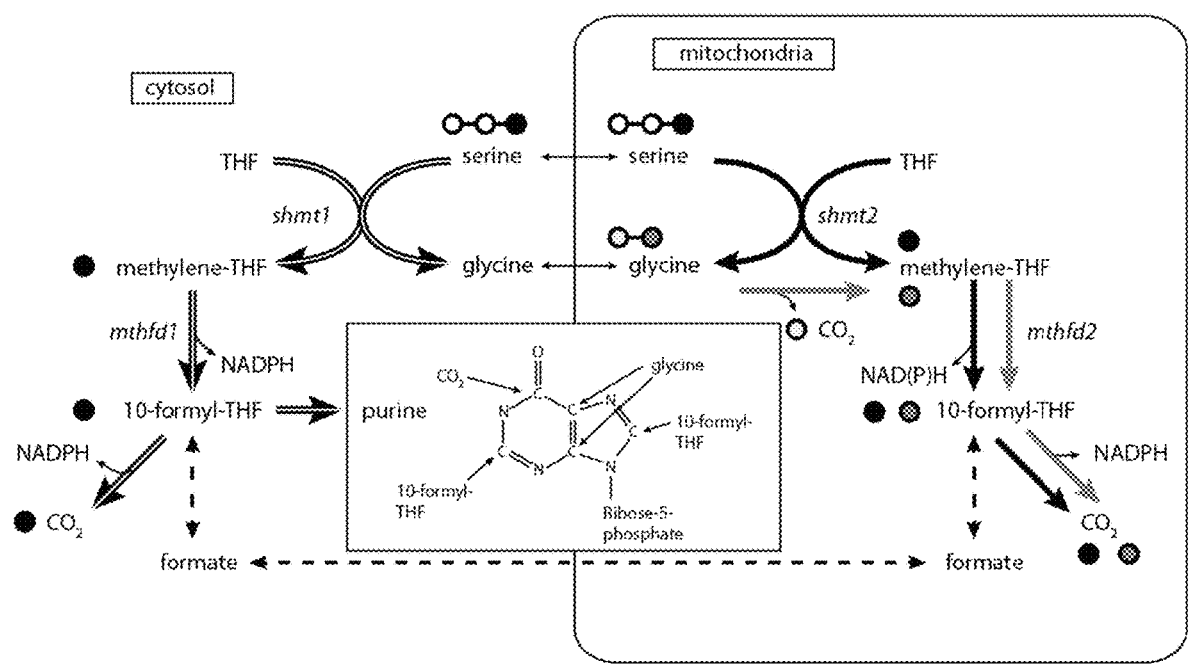
FIGS. 3A-3J show the quantitation of folate-dependent NADPH production.
Figure 3B:
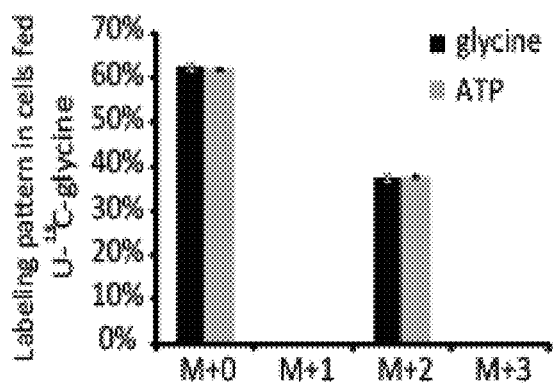
Figure 3C:
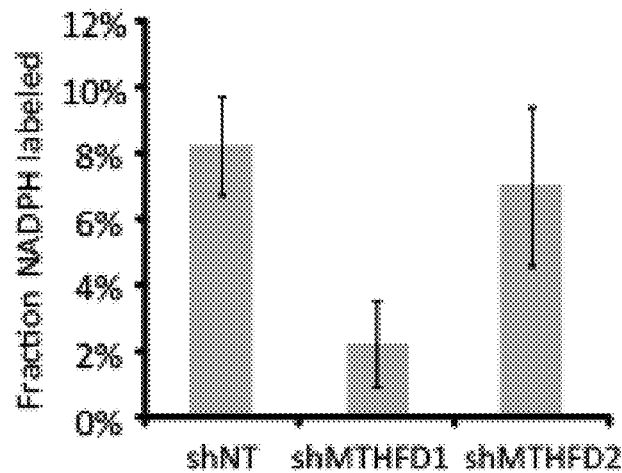
Figure 3D:
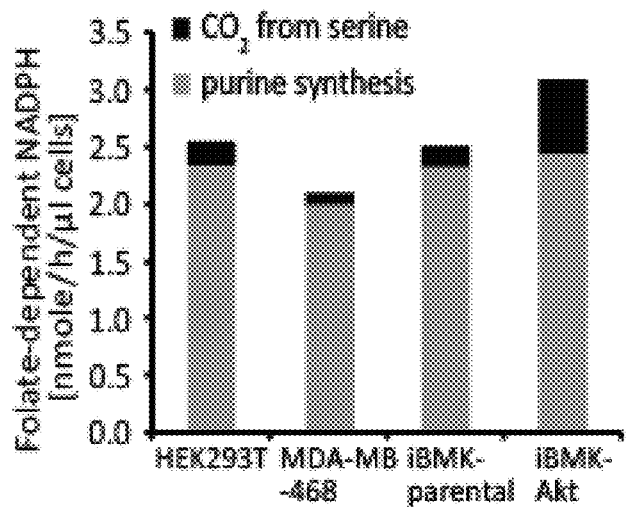
Figure 9A:
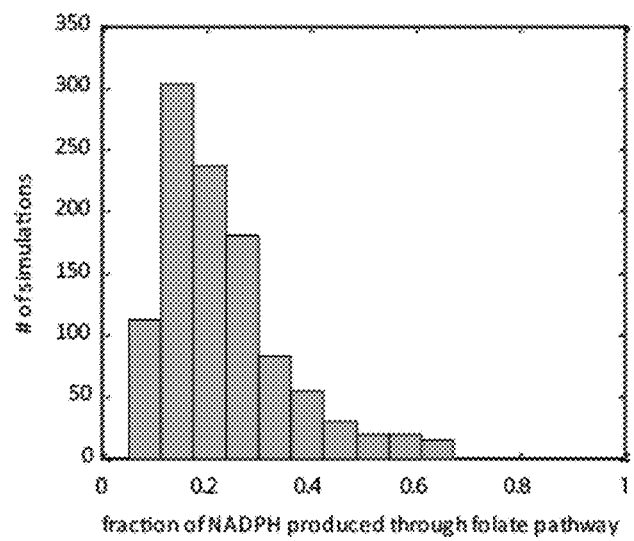
Figure 9B:
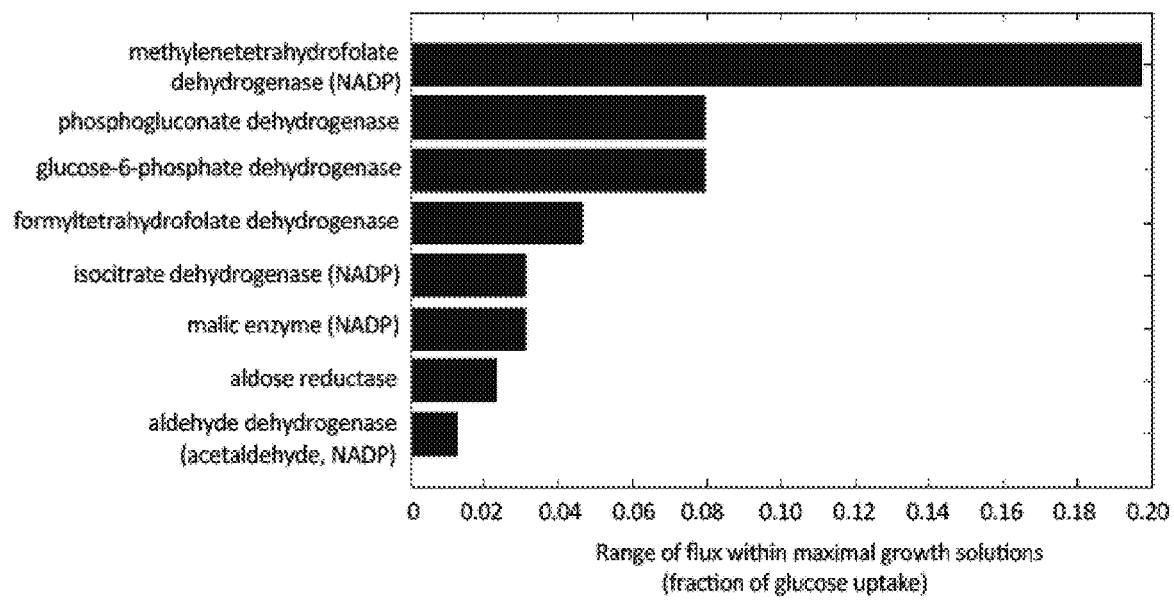
Figure 9C:
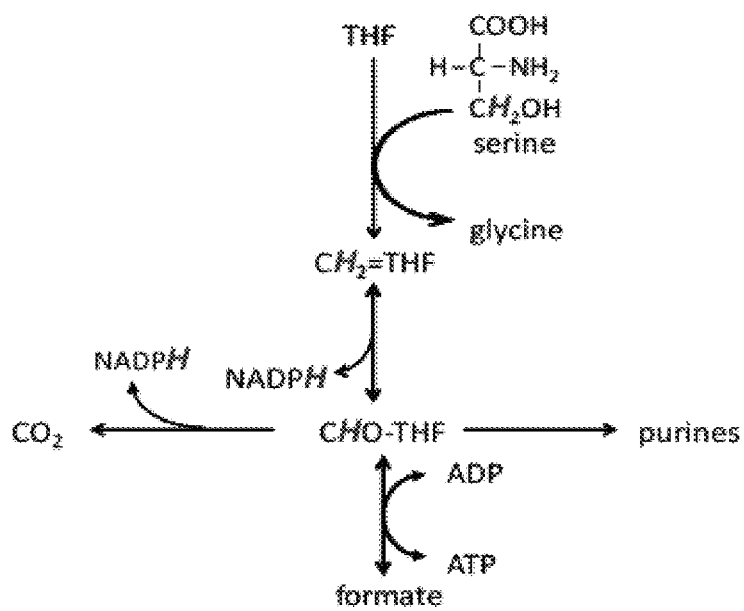
Figure 9D:
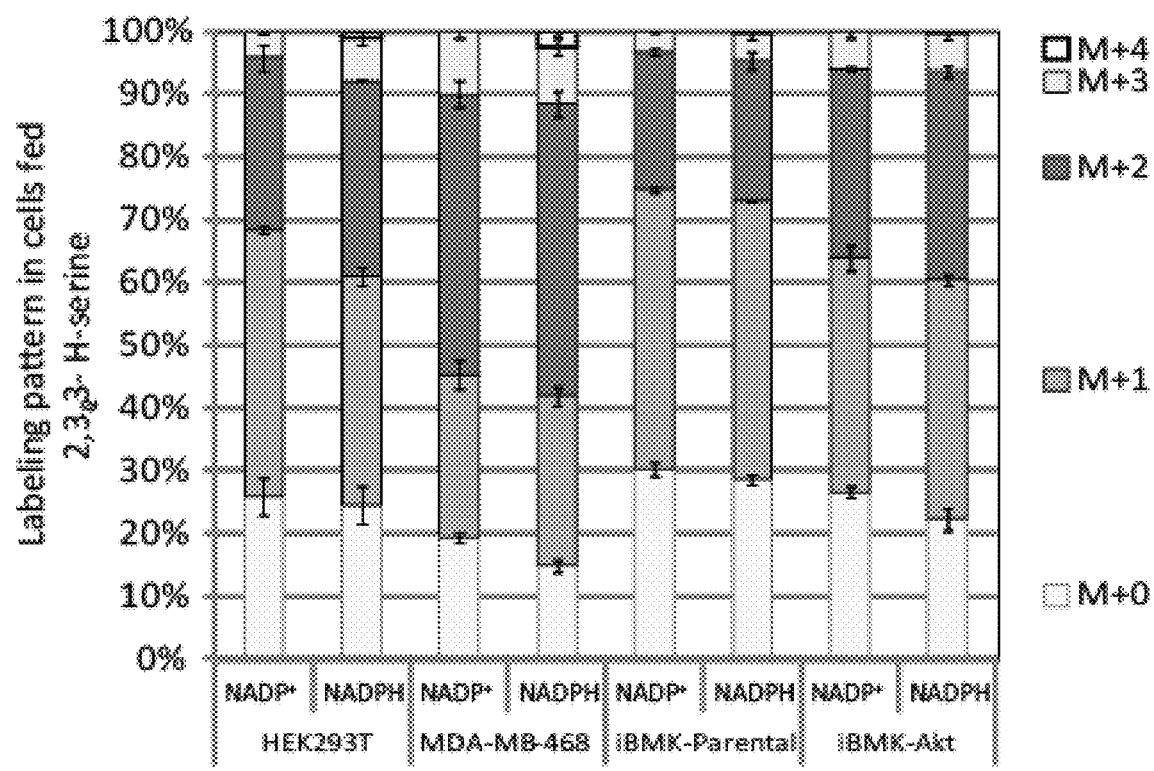

FIGS. 9A-9D show computational and experimental evidence for THF-dependent NADPH production. FIG. 9A shows the contribution of folate metabolism to NADPH production predicted herein based on flux balance analysis, using minimization of total flux as the objective function, across different biomass compositions. The biomass fraction of cell dry weight consisting of protein, nucleic acid, and lipid was varied as follows: protein 50%-90% with a step size of 10%; RNA/DNA 3%-20% with step size of 1%, and lipids 3%-20% with step size of 1% (considering only those combinations that sum to no more than 100%). With this range of physiologically possible biomass compositions, the model predicts a median contribution of folate metabolism of 24%. Note that with the constraint of experimentally measured biomass composition, yet without constraining the uptake rate of amino acids other than glutamine to be ≤1/3 of the glutamine uptake rate, the contribution of folate pathway to total NADPH production is predicted to be 23%. FIG. 9B shows the range of feasible flux through NADPH-producing reactions in Recon1 model computed via Flux Variability Analysis under the constraint of maximal growth rate. As shown, the model predicts that each NADPH-producing reaction can theoretically have zero flux, with all NADPH production proceeding through alternative pathways. Only reactions whose flux upper bound is greater than zero are shown. Reactions producing NADPH via a thermodynamically infeasible futile cycle were manually removed. As shown, among all NADPH-producing reactions, MTHFD has the highest flux consistent with maximal growth. FIG. 9C provides a pathway diagram showing the potential for 2,3,3-$^2$H-serine to label NADPH via methylene-tetrahydrofolate dehydrogenase. FIG. 9D shows the NADP+ and NADPH labeling pattern after 48 h incubation with 2,3,3-$^2$H-serine (no glycine present in the media). The greater abundance of more heavily labeled forms of NADPH relative to NADP+ indicates redox-active hydrogen labeling. Results are mean±SD, N≥2 biological replicates from a single experiment and were confirmed in N≥2 experiments. Based on the data in FIG. 9D, the contribution of MTHFD 1 to cytosolic NADPH production spans a broad range (10%-40%) of total NADPH; the range is due to variation across cell lines, experimental noise, and the large KIE (Pawelek, P. D. et al. (1998) "*Methenyltetrahydrofolate Cyclohydrolase Is Rate Limiting For The Enzymatic Conversion Of 10-Formyltetrahydrofolate To 5,10-Methylenetetrahydrofolate In Bifunctional Dehydrogenase-Cyclohydrolase Enzymes*," Biochemistry 37:1109-1115). This range includes the flux calculated based on purine biosynthetic rate and $^{14}CO_2$ release from serine (FIG. 3D). Note that the total contribution of the cytosolic folate metabolism to NADPH production can exceed that of MTHFD1, as 10-formyl-THF dehydrogenase also produces NADPH.

Figure 10A:
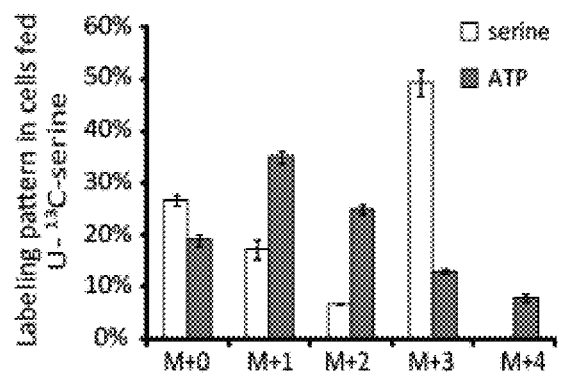
Figure 10B:
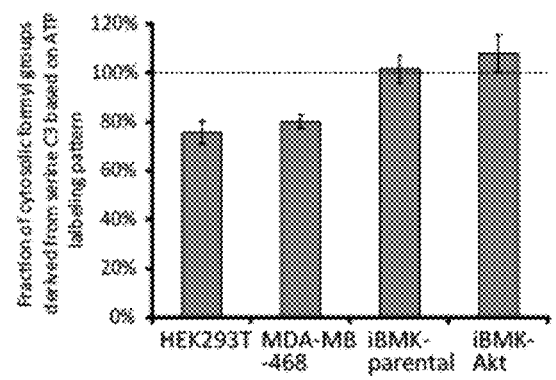
Figure 10C:
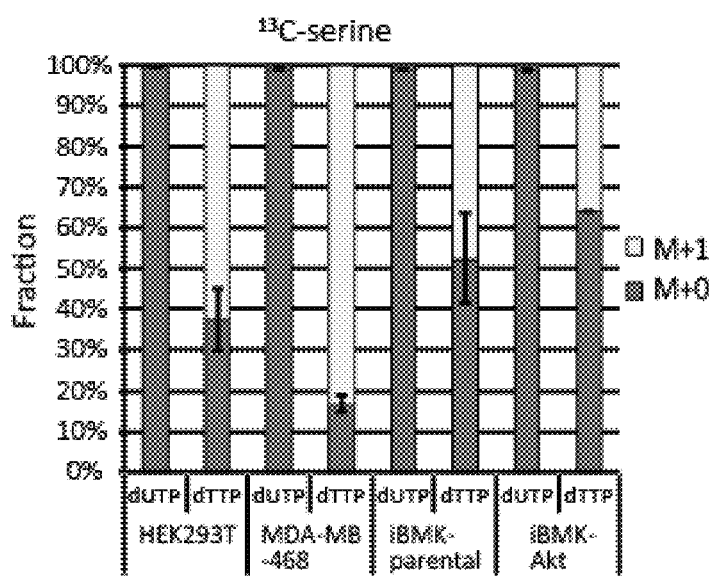
Figure 10D:
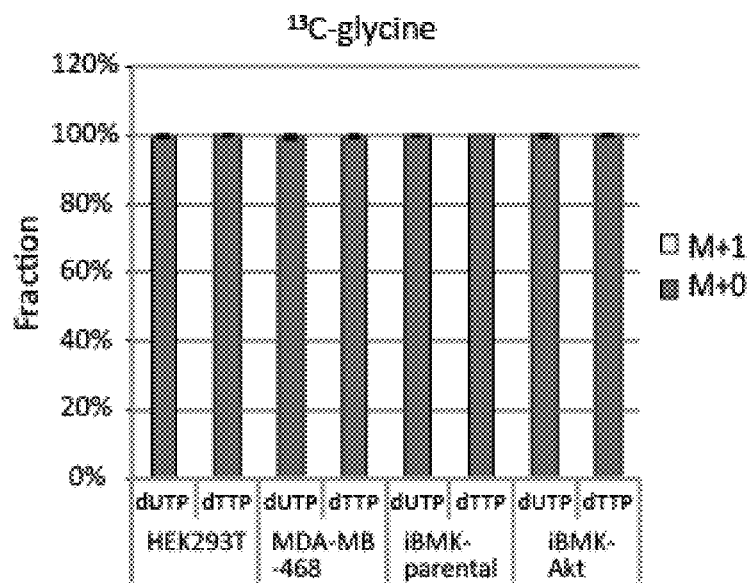
Figure 10E:
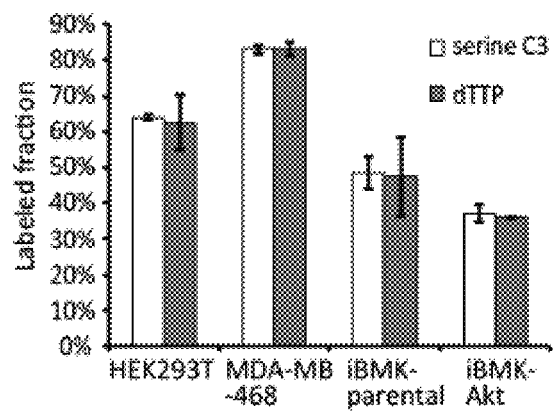
Figure 10F:
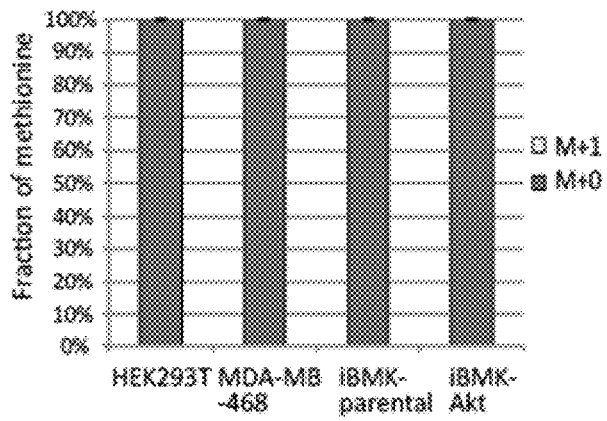

FIGS. 10A-10F show that one-carbon units used in purine and thymidine synthesis are derived from serine. FIG. 10A shows the serine and ATP labeling pattern after 24 h incubation of HEK293 T cells with U-$^{13}$C-serine. The presence of M+1 to M+4 ATP indicates that serine contributes carbon to purines both through glycine and through one-carbon units derived from serine C3. FIG. 10B provides a quantitative analysis of cytosolic one-carbon unit labeling from measured the intracellular ATP, glycine, and serine labeling that reveals that most cytosolic 10-formyl-THF assimilated into purines comes from serine. FIG. 10C shows that U-$^{13}$C-serine labels the methyl group that distinguishes dTTP from dUTP. FIG. 10D shows that U-$^{13}$C-glycine does not label dTTP. FIG. 10E shows that the extent of dTTP labeling mirrors the extent of intracellular serine labeling. FIG. 10F shows that methionine does not label from U-$^{13}$C-glycine. In all experiments, cells were grown in U-13C-serine or glycine for 48 h. Mean±SD, N=3.

Figure 11A:
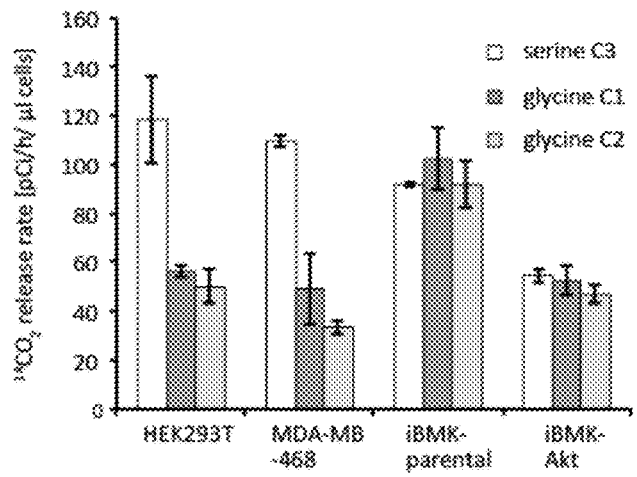
Figure 11B:
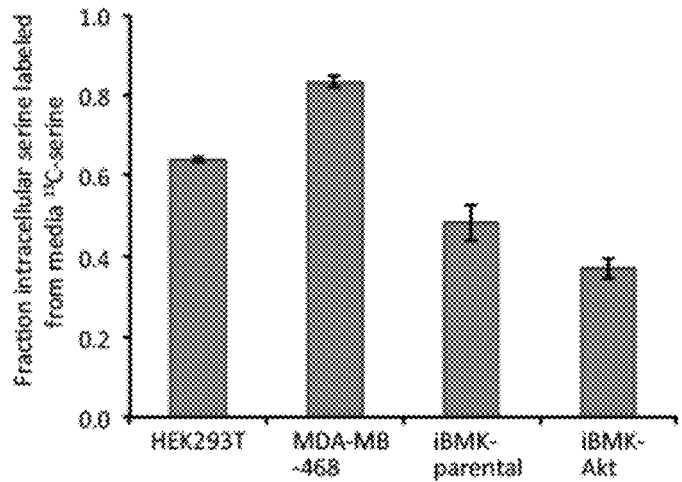
Figure 11C:
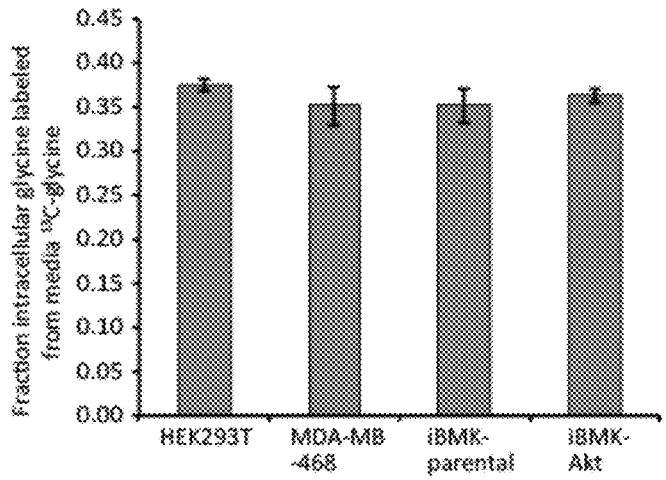
Figure 11G:
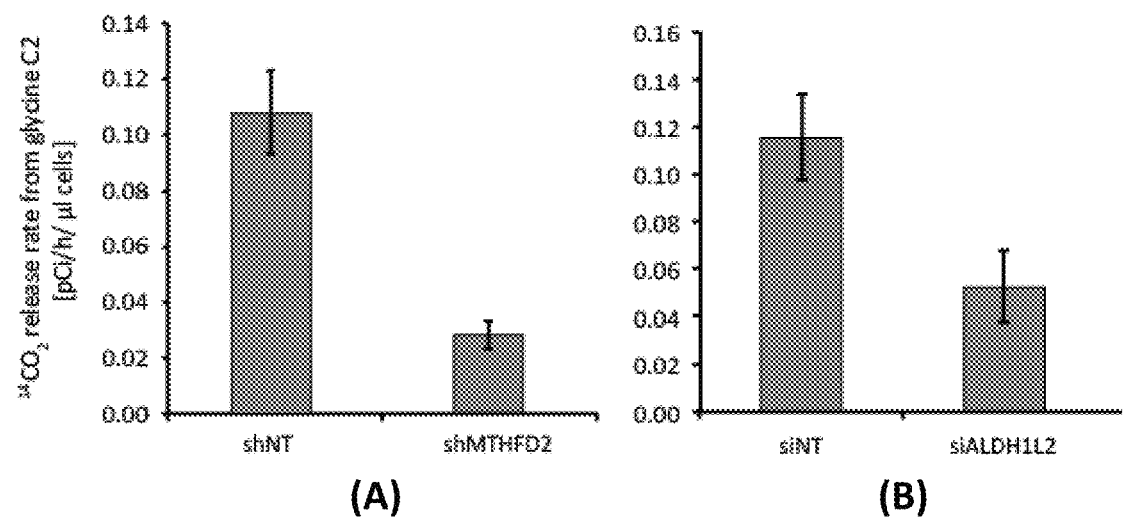
Figure 11H:
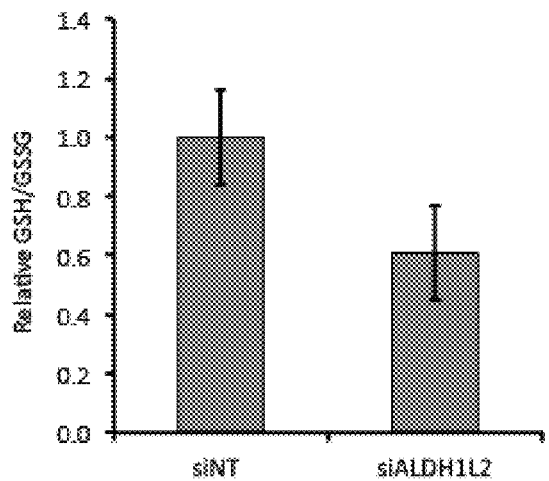

FIGS. 11A-11H show a measurement of the $CO_2$ release rate from serine and glycine by combination of $^{14}$C- and $^{13}$C-labeling. FIG. 11A shows the $^{14}CO_2$ release rate when cells are fed medium with a trace amount of 3-$^{14}$C-serine, 1-$^{14}$C-glycine or 2-$^{14}$C-glycine. FIG. 11B shows the fraction of intracellular serine labeled in cells grown in DMEM medium containing 0.4 mM 3-$^{13}$C-serine in place of unlabeled serine. The residual unlabeled serine is presumably from de novo synthesis. FIG. 11C shows the fraction of intracellular glycine labeled in cells grown in DMEM medium containing 0.4 mM U-13C-glycine in place of unlabeled glycine. FIG. 11D shows the $CO_2$ release rates from serine C3, glycine C1 or C2. FIG. 11E shows a potential alternative pathway to metabolize glycine or serine into $CO_2$ via pyruvate. FIG. 11F shows the pyruvate labeling fraction after 48 h labeling with U-$^{13}$C-serine or U-$^{13}$C-glycine. The lack of labeling in pyruvate indicates that serine and glycine are not metabolized through this pathway. FIG. 11G shows that knockdown of MTHFD2 (FIG. 11G, Panel (A)) or ALDH1L2 (FIG. 11G, Panel (B)) decreases $CO_2$ release from glycine C2. FIG. 11H shows that knockdown of ALDH1L2 decreases the GSH/GSSG ratio. Mean+SD, N=3.

Figure 12A:
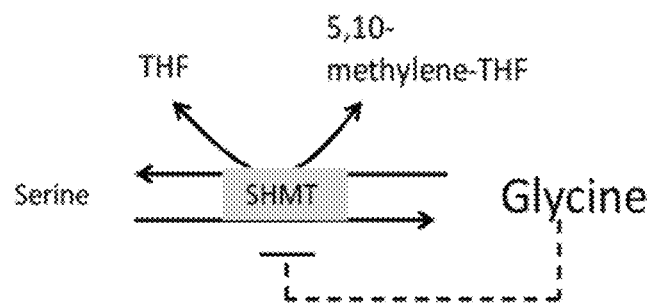
Figure 12B:
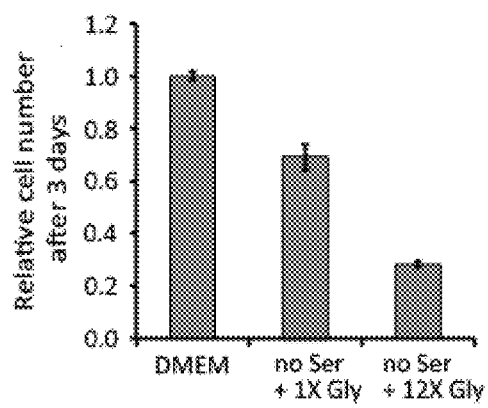
Figure 12C:
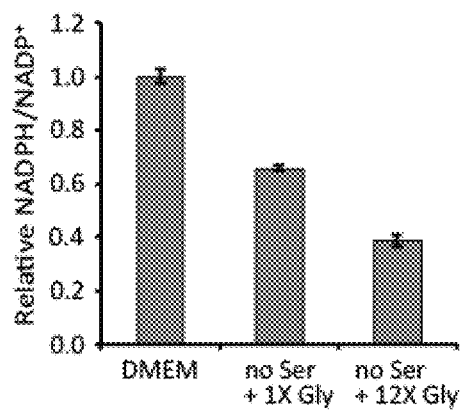
Figure 12D:
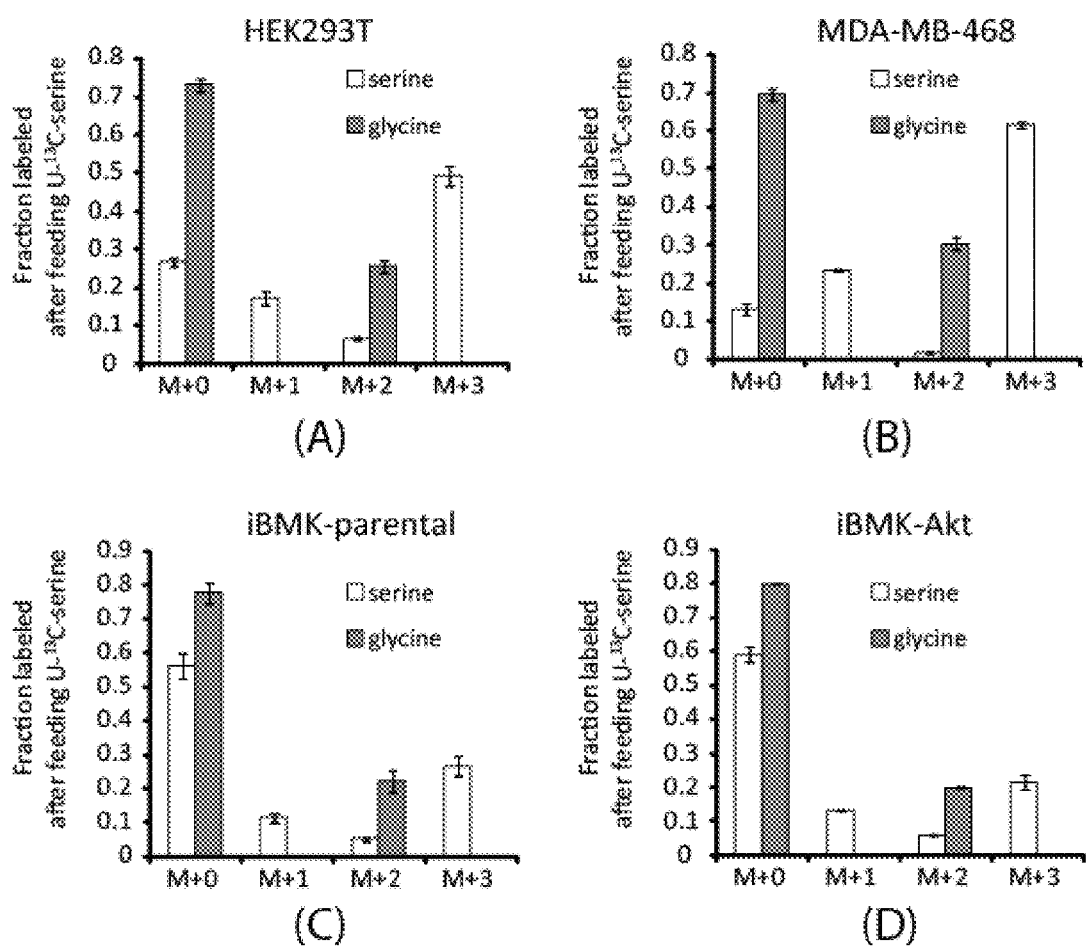
Figure 12E:
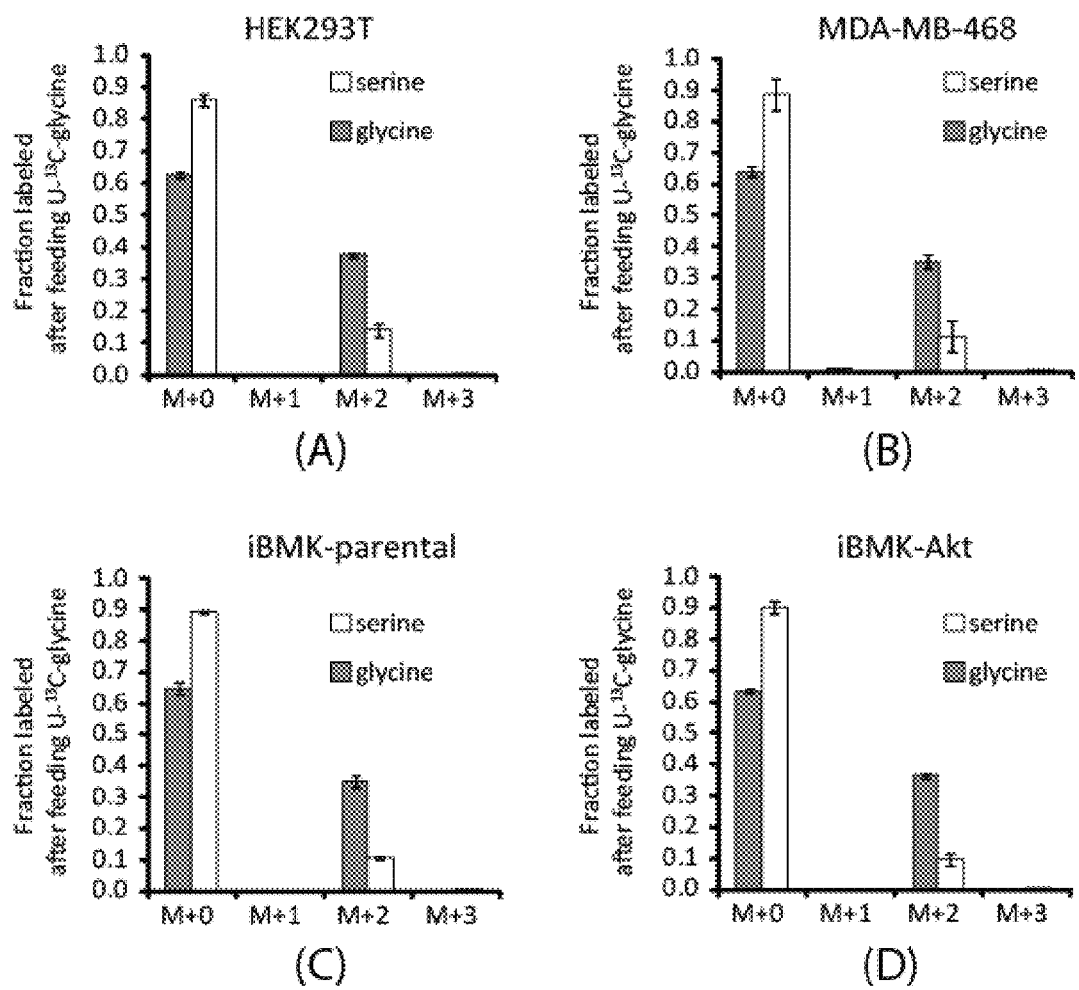

FIGS. 12A-12E show that in the absence of serine, elevated concentrations of glycine inhibit cell growth and decrease the NADPH/NADP+ ratio. FIG. 12A provides a schematic of the serine hydroxymethyltransferase reaction. High glycine may either inhibit forward flux (product inhibition) or drive reserve flux. FIG. 12B shows the relative cell number observed after culturing HEK293T cells for 3 days in regular DMEM, DMEM with no serine, and DMEM with no serine and 12.5-times the normal concentration of glycine (5 mM instead of 0.4 mM). FIG. 12C shows the relative NADPH/NADP+ ratio (normalized to cells grown in DMEM) after culturing HEK293T cell for 3 days in regular DMEM, DMEM with no serine, and DMEM with no serine and 12.5-times the normal concentration of glycine. FIGS. 12D and 12E show that the labeling of serine and glycine after feeding HEK293 T cells (FIGS. 12D-12E, Panel (A)) MDA-MB-498 cells (FIGS. 12D-12E, Panel (B)), iBMK-parental cells (FIGS. 12D-12E, Panel (C)) or iBMK-Akt cells (FIGS. 12D-12E, Panel (D)) U-$^{13}$C-serine (FIG. 12D) or U-$^{13}$C-glycine (FIG. 12E) reveals reverse serine hydroxymethyltransferase flux. Mean+SD, N=3.

Figures 13A, 13B, 13C:
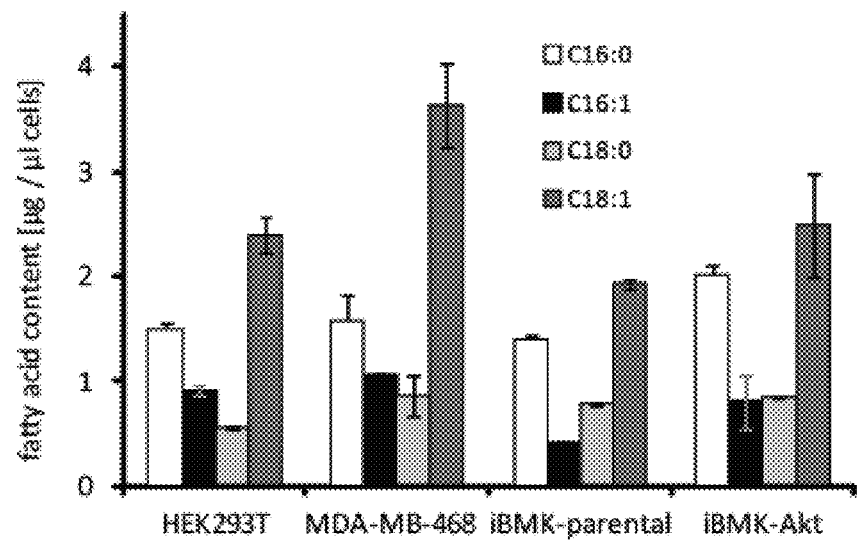
Figure 13D:
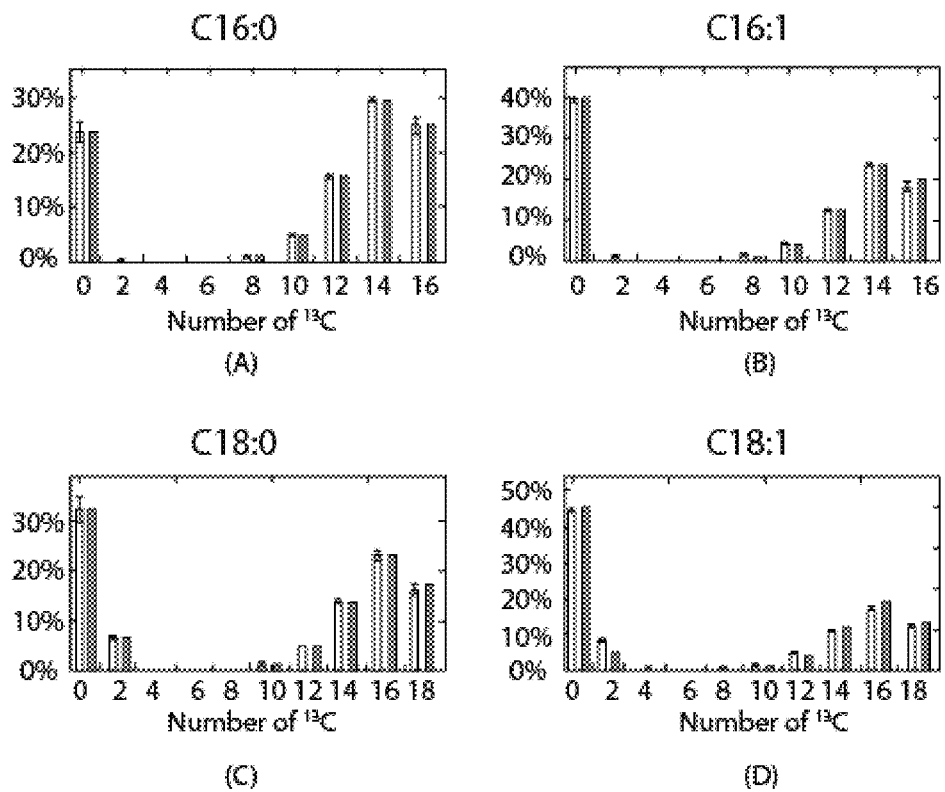
Figure 13E:
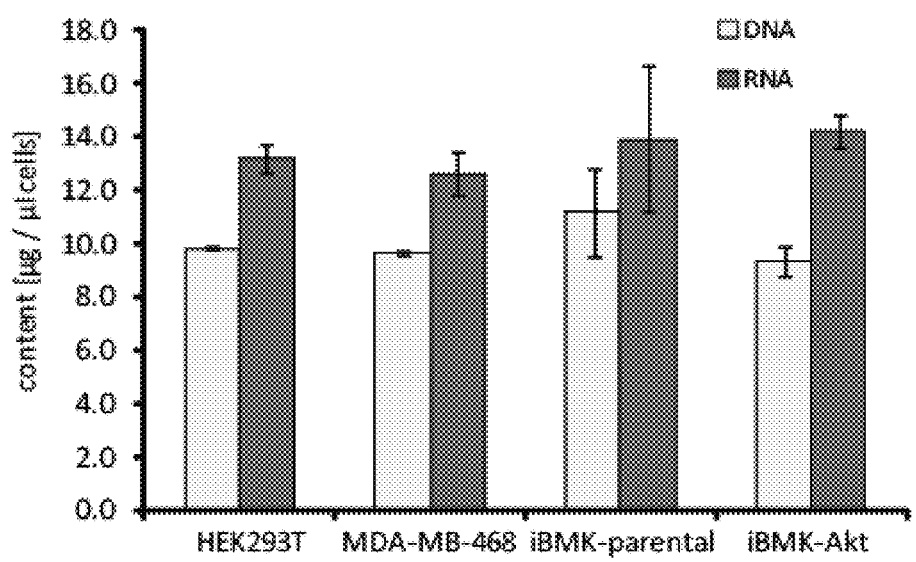
Figure 13F:
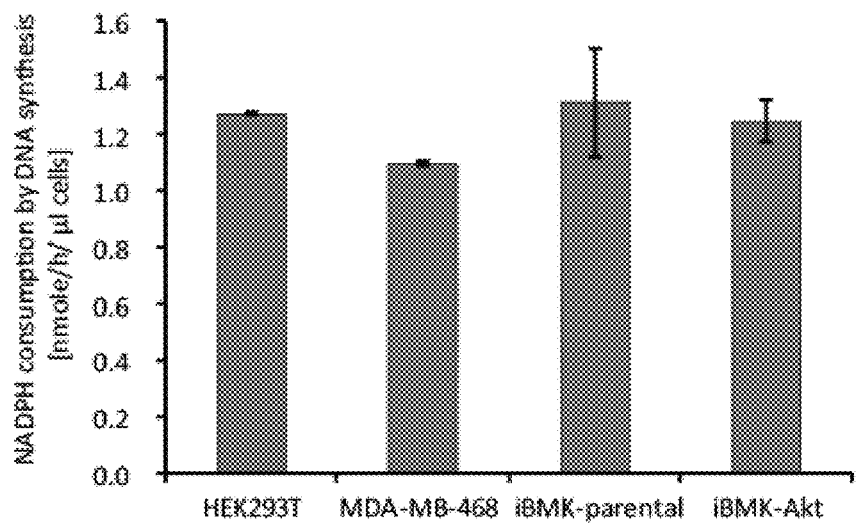
Figure 13G:
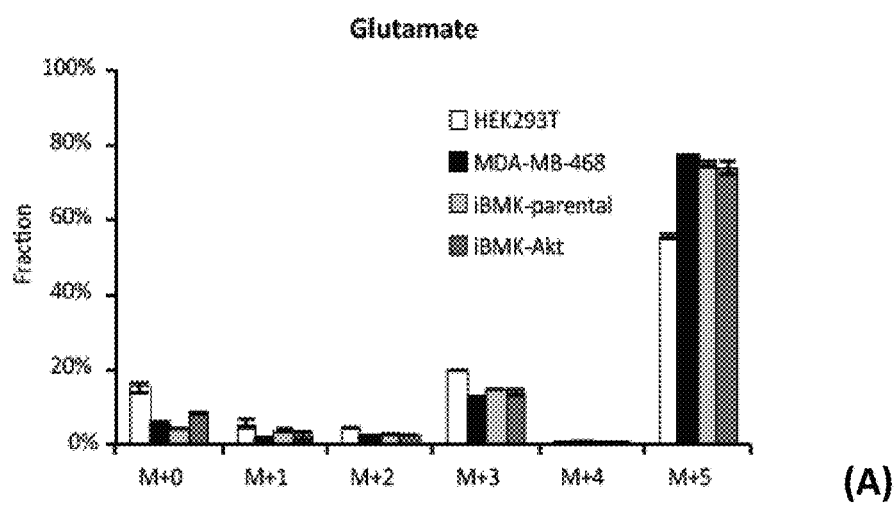
Figure 13G:
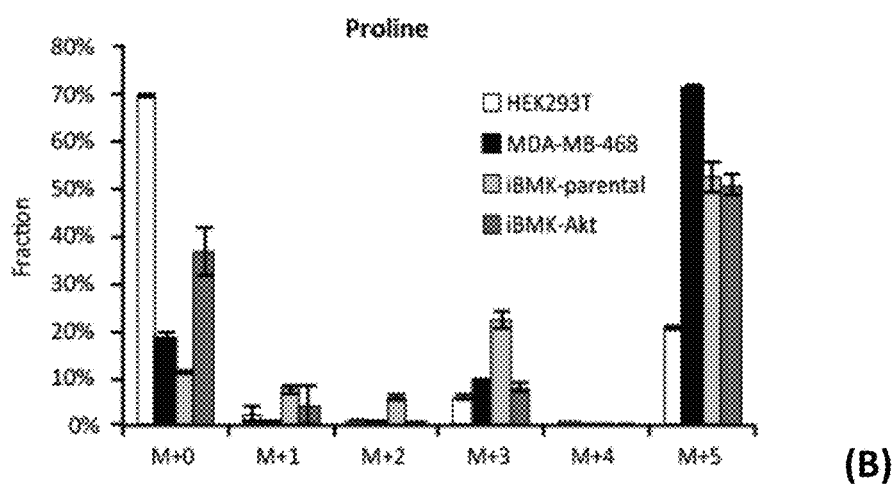
Figure 13H:
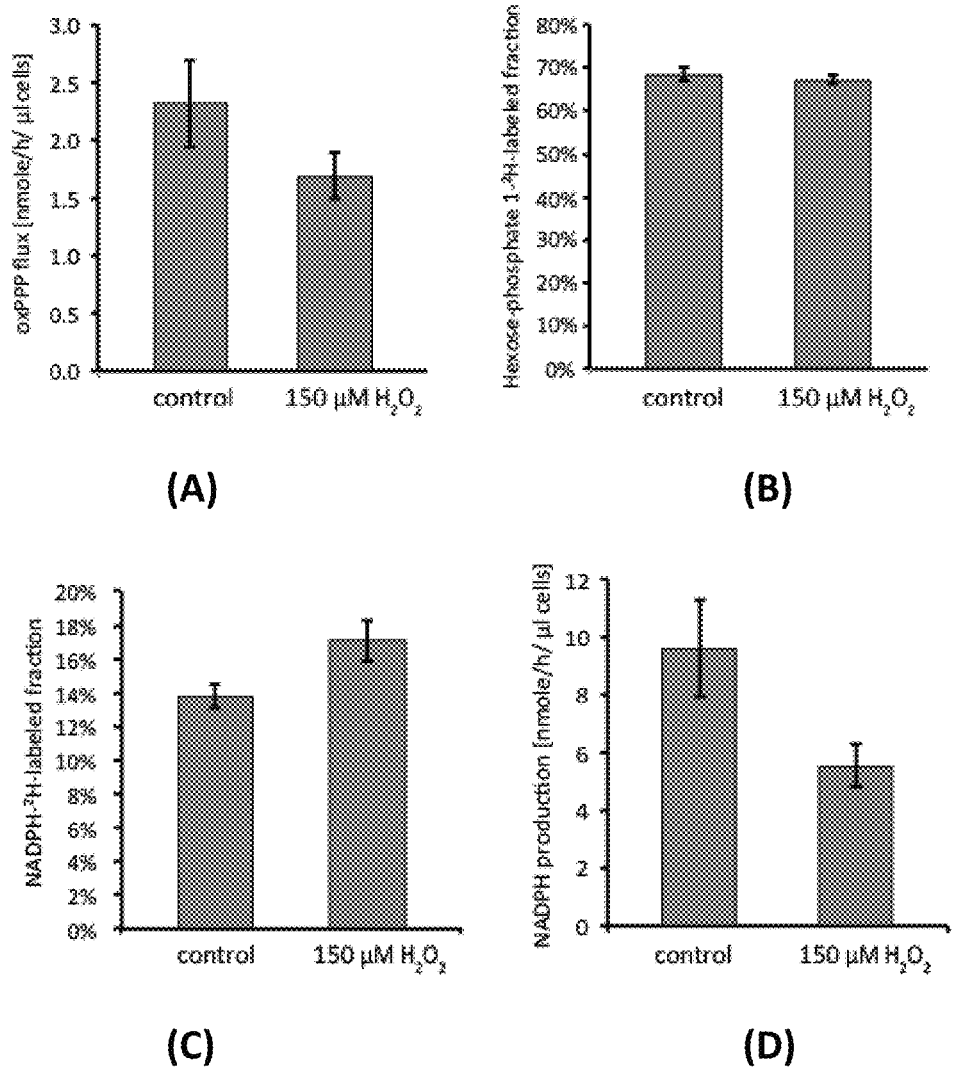

FIGS. 13A-13H show a quantitative analysis of NADPH consumption for biomass production and antioxidant defense. FIG. 13A shows cell doubling times, which are inversely proportional to biomass production rates. FIG. 13B shows cellular protein content. FIG. 13C shows cellular fatty acid content (from saponification of total cellular lipid). FIG. 13D shows quantitation of fatty acid synthesis versus import, with synthesis but not import requiring NADPH. HEK293T cells were cultured in U-$^{13}$C-glucose and U-$^{13}$C-glutamine until pseudo-steady-state, and fatty acids saponified from total cellular lipids and their labeling patterns measured (light bars), and production versus import of each fatty acid was stimulated based on this experimental data. The fractional contribution of each route was determined by least square fitting, with the theoretical labeling pattern based on the elucidated routes shown (dark bars). FIG. 13D, Panel (A): C16:0; FIG. 13D, Panel (B): C16:1; FIG. 13D, Panel (C): C18:0; FIG. 13D, Panel (D): C18:1. Similar data were obtained also for MD-MBA-468, iBMK-parental, and iBMK-Akt cells and used to calculate associated NADPH consumption by fatty acid synthesis. FIG. 13E shows cellular DNA and RNA contents. FIG. 13F shows NADPH consumption by de novo DNA synthesis. FIG. 13G shows glutamate (Panel (A)) and proline (Panel (B)) labeling patterns after 24 h in U-$^{13}$C-glutamine media, which was used to quantitate different proline synthesis routes and associated NADPH consumption. FIG. 13H shows a quantitative analysis of cytosolic NADPH consumption in normally growing HEK293T cells (control) and non-growing cell under oxidative stress (150 µM $H_2O_2$, 5 h). Total cytosolic NADPH turnover was measured based on the absolute oxPPP flux divided by the fractional contribution of the oxPPP to total NADPH as measured using NADP2H formation from 1-$^2$H-glucose. Mean±SD, N=3. FIG. 13H, Panel (A): oxPPP flux; FIG. 13H, Panel (B): hexose-phosphate 1-$^2$H-labeled fraction; FIG. 13H, Panel (C): NADPH-$^2$H-labeled fraction; FIG. 13H, Panel (D): NADPH production [nmole/h/µl cells].

Figure 14A:
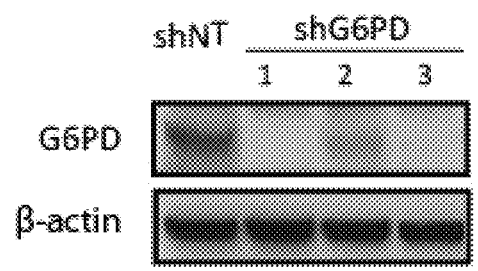
Figure 14B:
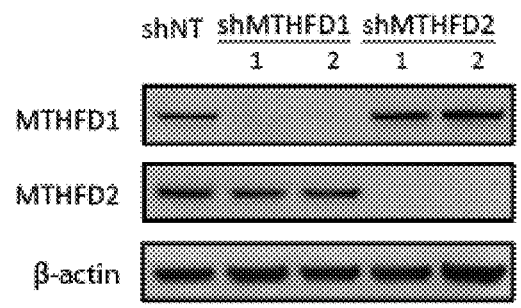
Figure 14C:
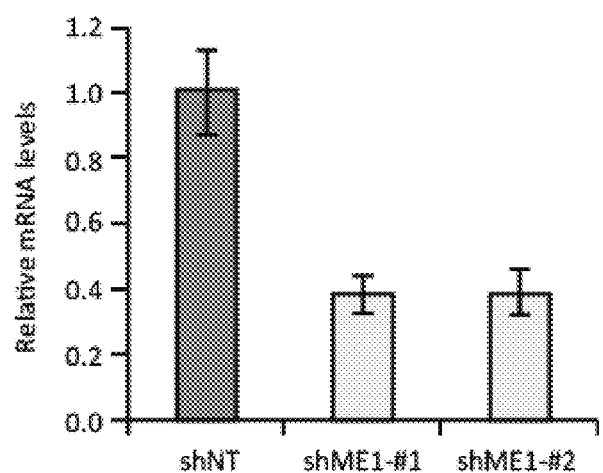

FIGS. 14A-14G show confirmation of knockdown efficiency by Western blot or Q-PCR. FIG. 14A shows a Western blot for G6PD knockdown. FIG. 14B shows a Western blot for MTHFD1 and MTHFD2 knockdown. FIG. 14C shows the mRNA level for ME1 knockdown. FIG. 14D shows the mRNA level for NNT knockdown. FIG. 14E shows the Western blot for IDH1 and IDH2 knockdown. FIG. 14F shows a Western blot for ALDH1L2 knockdown. FIG. 14G shows cell doubling times of HEK293T cells with stable knockdown of indicated genes (results for different hairpins of the same gene were indistinguishable).

Figure 15A:
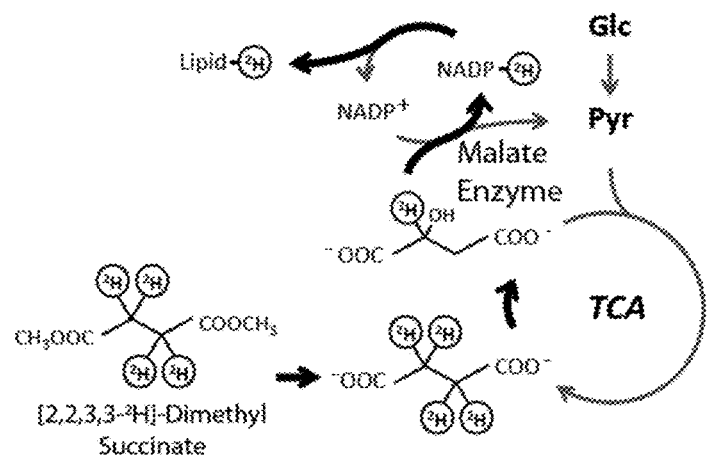
Figure 15B:
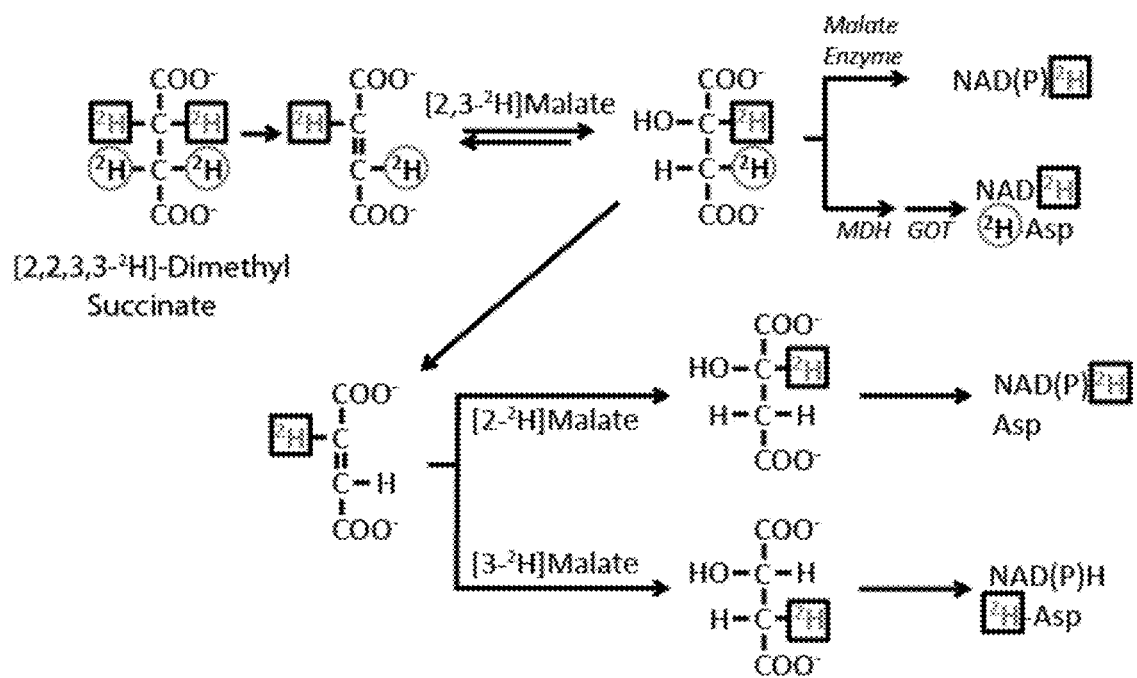
Figure 15C:
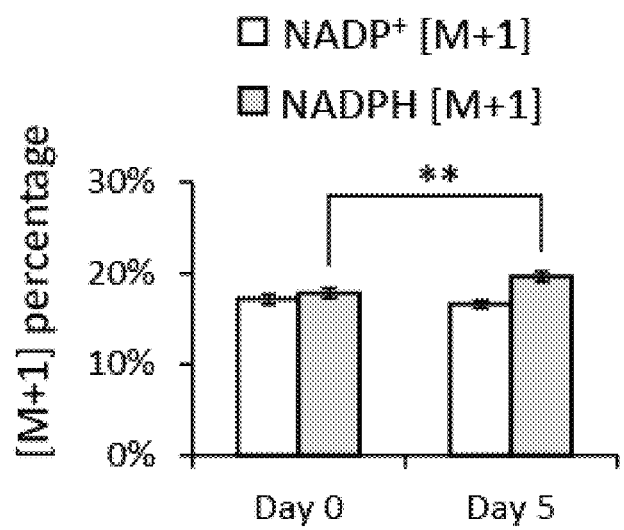
Figure 15D:
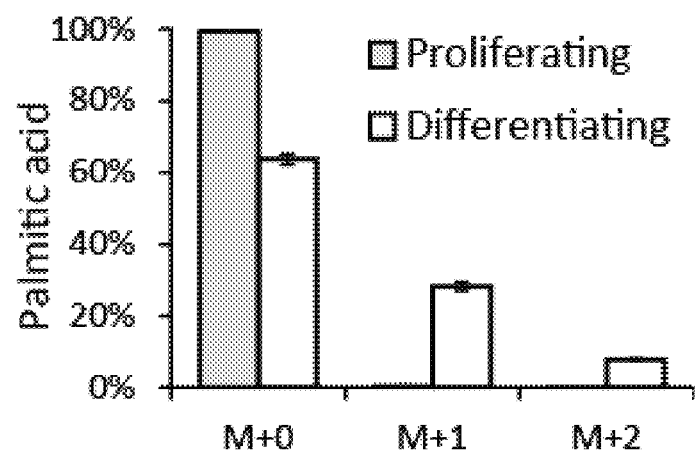
Figures 15E, 15F:
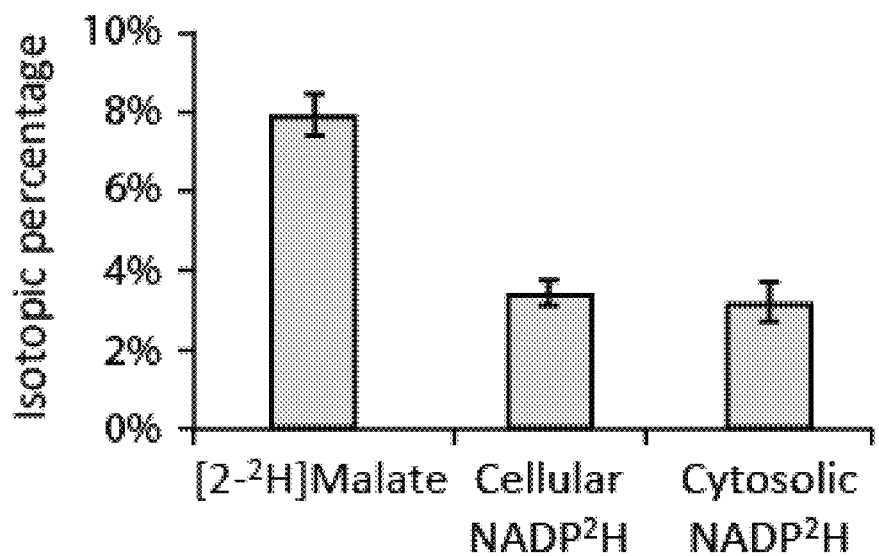

FIGS. 15A-15F show the tracing of hydride flux through malic enzyme and total adipocyte central metabolic activity. FIG. 15A is a schematic of 2,2,3,3-$^2$H-dimethyl-succinate metabolism. As shown in the Figure, $^2$H at malate position 2 is transferred to NADPH and lipid via malic enzyme (thick black arrows). Glc, glucose; Pyr, pyruvate; ME, malic enzyme; Suc, succinate; Mal, malate. FIG. 15B shows the differential fate of $^2$H at malate position 2 versus 3, and the potential for exchange between the two positions due to the symmetry of fumarate. MDH, malate dehydrogenase; GOT, glutamate-oxaloacetate transaminase; Asp, aspartate. FIG. 15C shows NADP(H) $^2$H-labeling in 3T3-L1 adipocytes (day 0 or day 5) fed 2,2,3,3-$^2$H-dimethyl succinate for 24 hours. FIG. 15D shows the results of mass spectroscopy analysis of palmitic acid in 3T3-L1 adipocytes fed 2,2,3,3-$^2$H-dimethyl succinate for 5 days. In the proliferating condition, cells were maintained at ≤80% confluency with no differentiating reagents. In the differentiating condition, cells were provided with a differentiation cocktail with tracer added starting on day 0. FIG. 15E shows the extent of $^2$H-labeling of malate and aspartate in 3T3-L1 adipocytes at day 5. FIG. 15F shows labeling in 3T3-L1 adipocytes (at day 5) of malate (fraction labeled at redox-active hydride at position 2, whether or not also labeled at other positions, see FIG. 5E), whole cell NADPH (measured directly), and cytosolic NADPH (inferred from labeling of a set of abundant fatty acids).

Figure 16:
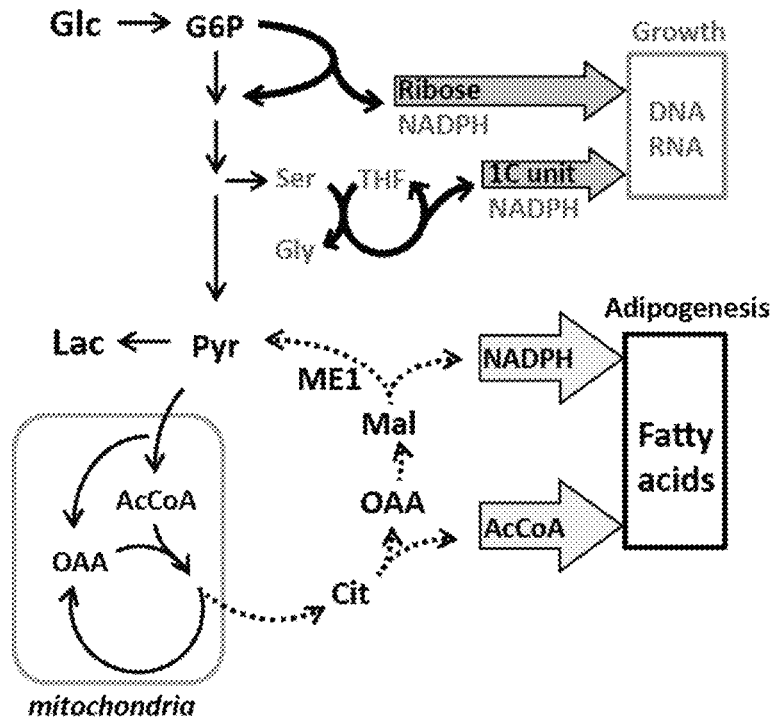

FIG. 16 is a schematic of the pyruvate-citrate cycle driven by malate enzyme 1 (ME1) to promote fatty acid synthesis.

Figure 17:
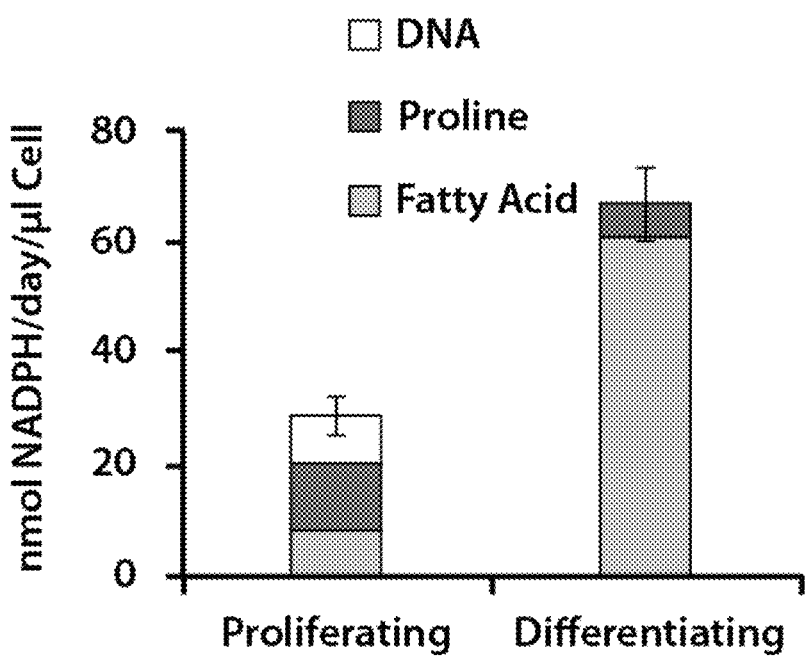

FIG. 17 shows NADPH biosynthetic consumption fluxes in proliferating and differentiating (day 5) 3T3-L1 cells. Data are mean±s.d., n=3.

Figure 18:
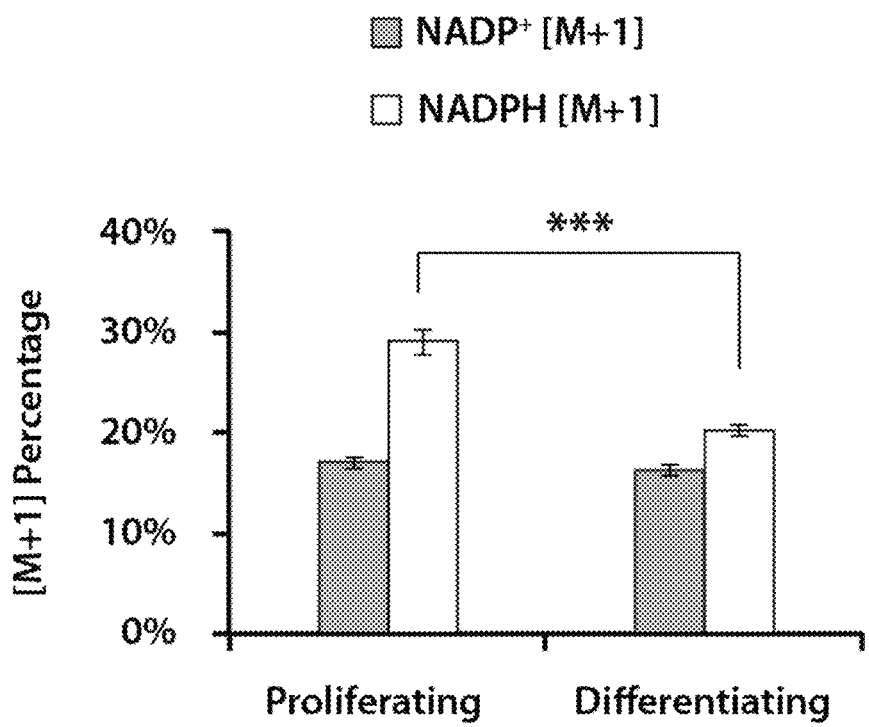

FIG. 18 shows NADP(H) $^2$H-labeling in 3T3-L1 cells fed 1-$^2$H-glucose for 2 h.

Figure 19:
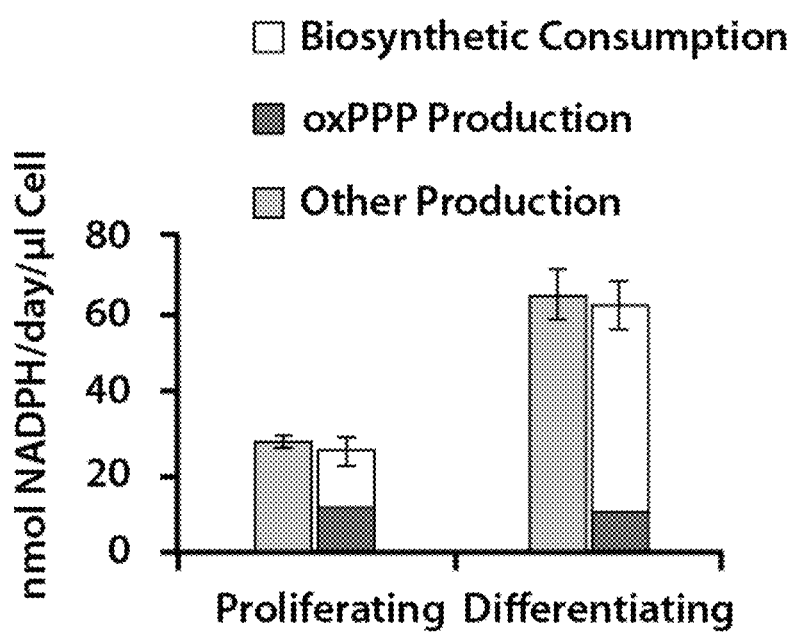

FIG. 19 shows a comparison of NADPH production with biosynthetic NADPH consumption. Total NADPH consumption was calculated from absolute oxPPP flux divided by NADPH fraction measured by NADPH labeling. Data are mean±s.d., n=3.

Figure 20:
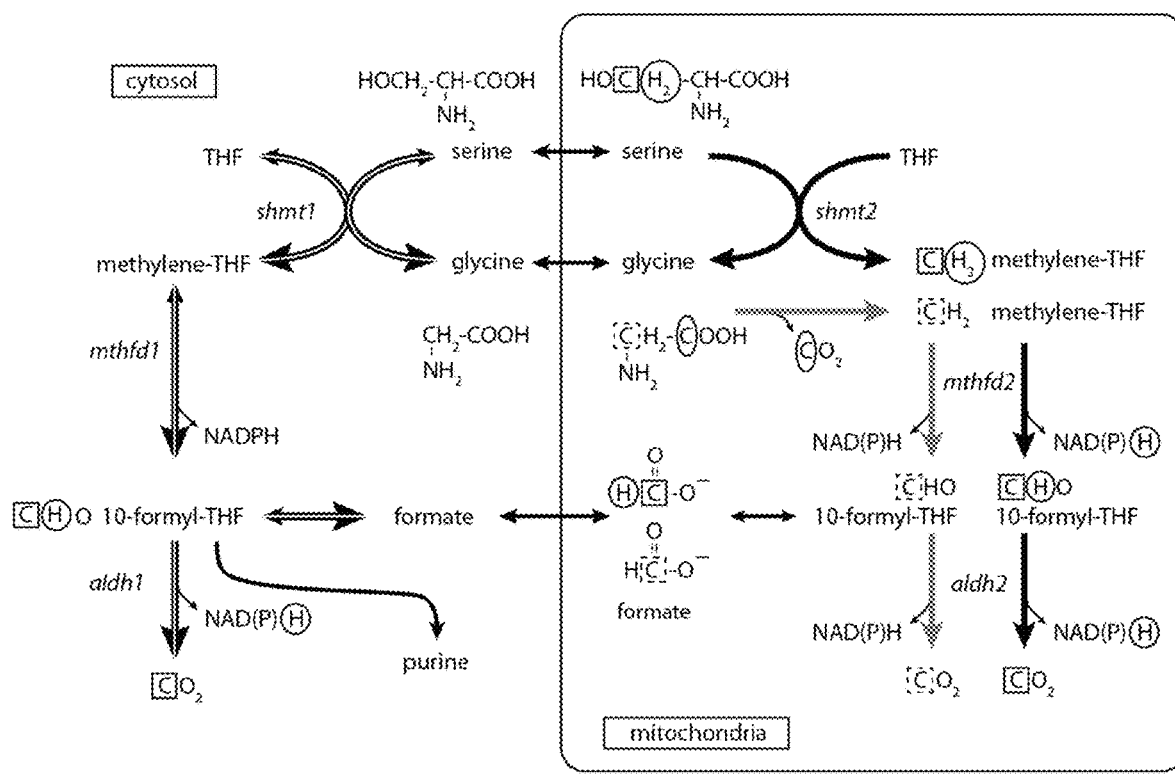

FIG. 20 shows a schematic of the folate pathway. MTHFD, methylenetetrahydrofolate dehydrogenase; ALDH, aldehyde dehydrogenase. Depending on conditions, the catalyzed reactions may proceed in the reverse direction (indicated with smaller arrowheads).

Figure 21:
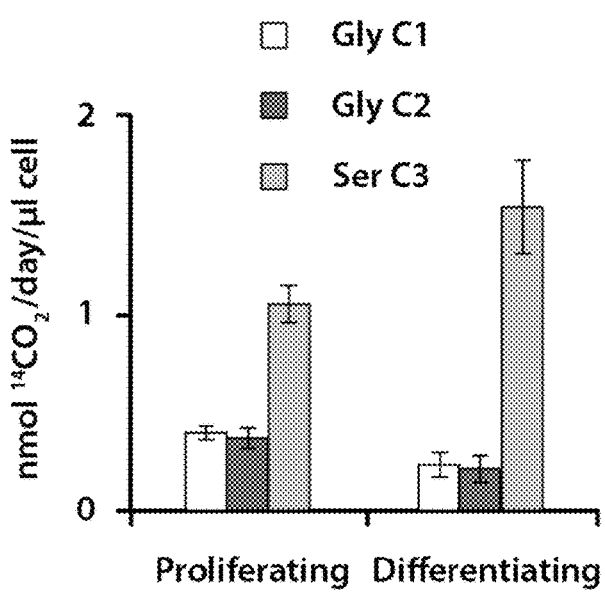

FIG. 21 shows $^{14}CO_2$ release from 1-$^{14}$C-glycine, 2-$^{14}$C-glycine, or 3-$^{14}$C-Serine by proliferating 3T3-L1 cells.

Figure 22:
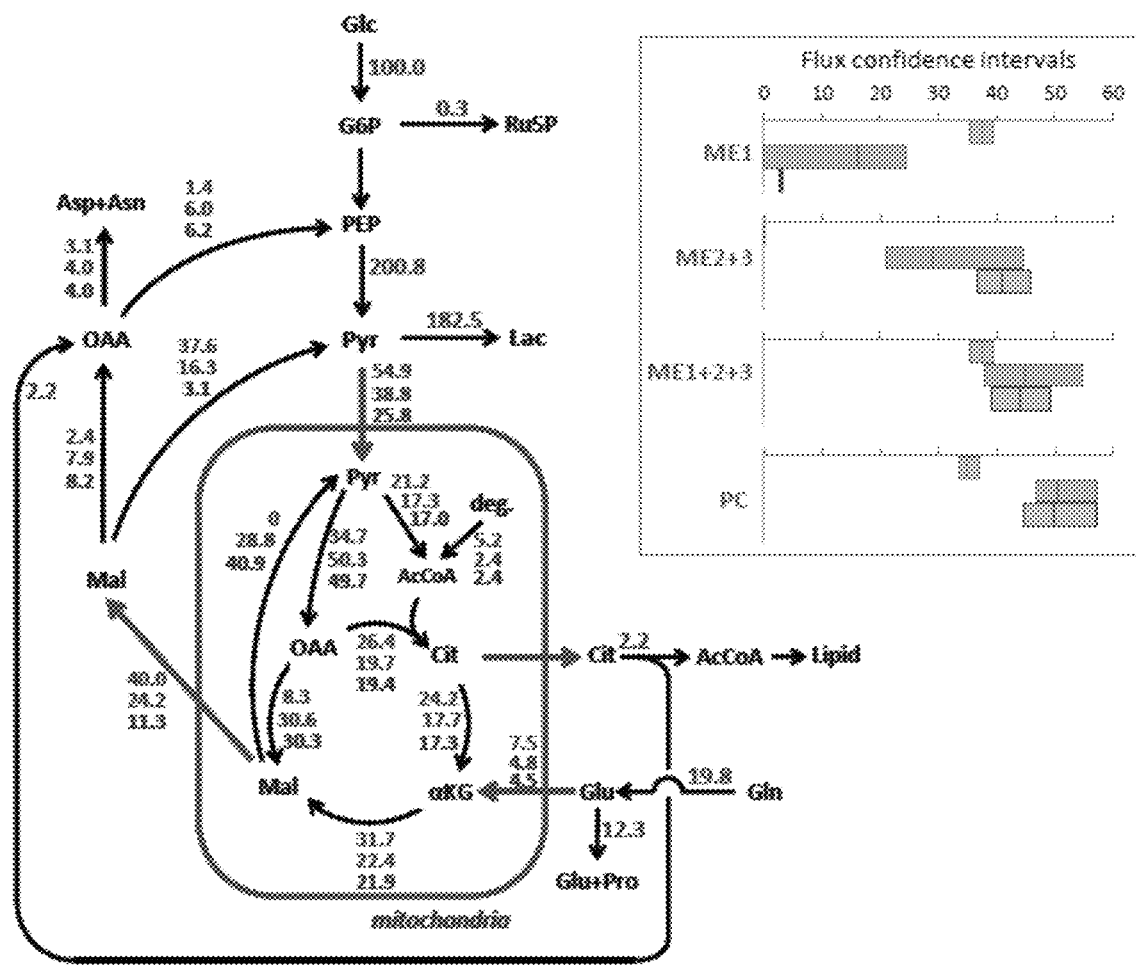

FIG. 22 shows determinations of the central carbon metabolic fluxes in differentiating 3T3-L1 adipocytes based on metabolic flux analysis informed by nutrient uptake, waste excretion, and biomass production fluxes, as well as LC-MS analysis of intracellular metabolite labeling in 3T3-L1 adipocytes fed U-$^{13}$C-glucose or U-$^{13}$C-glutamine. Numbers shown are the best fitting flux sets for 3 different conditions: topmost values ("ME1 Only") reflect a simplified network with cytosolic (ME1) but not mitochondrial (ME2 or ME3) malic enzyme; middle values ("ME1/2/3") reflect the simplified network with inclusion of mitochondrial malic enzyme (ME2 or ME3); bottom values ("ME1(constrained)/2/3") reflect a constraint of the ME1 flux based on $^2$H labeling data. ME1/2/3 and ME1(constrained)/2/3 flux values are only shown when they are more than 10% different from the ME1 Only value. Confidence intervals for malic enzyme and pyruvate carboxylase fluxes are shown in the inset. The inset shows sets of three horizontal bars, each corresponding to a flux confidence interval (topmost bar: ME1 Only; middle bar: ME1/2/3; bottom bar: ME1(constrained)/2/3).

Figure 23A:
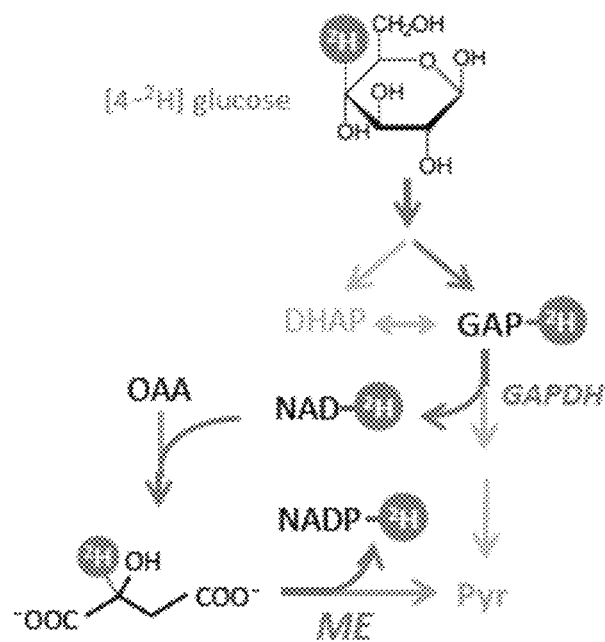
Figure 23B:
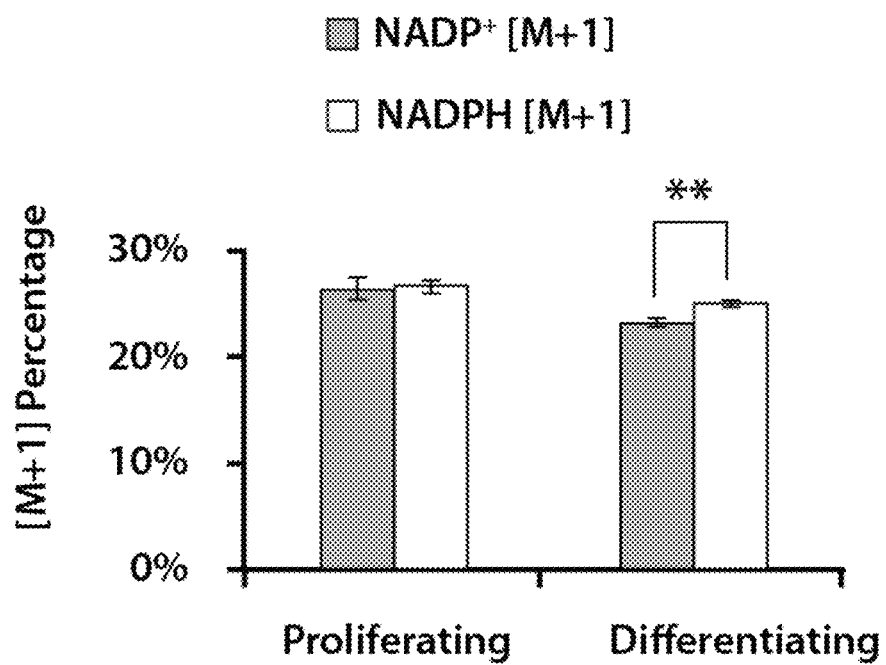
Figure 23C:
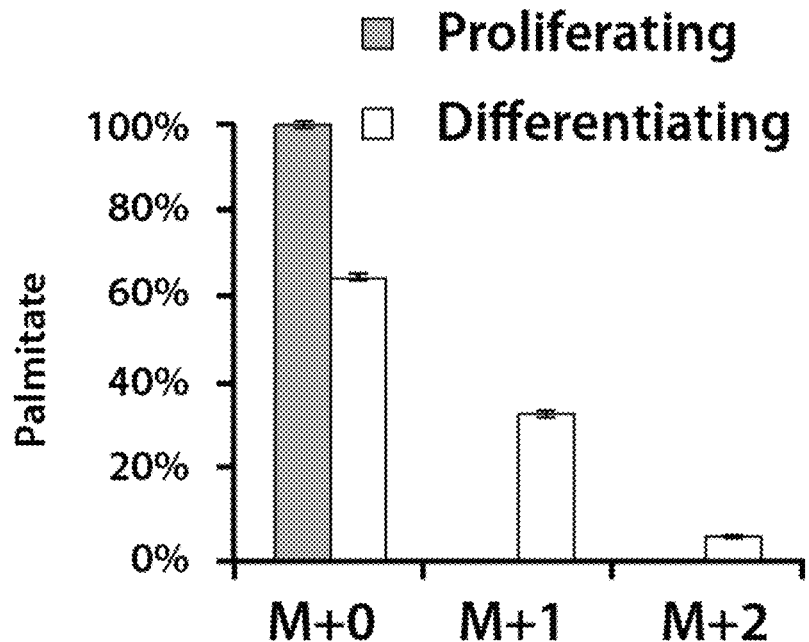
Figure 23D:
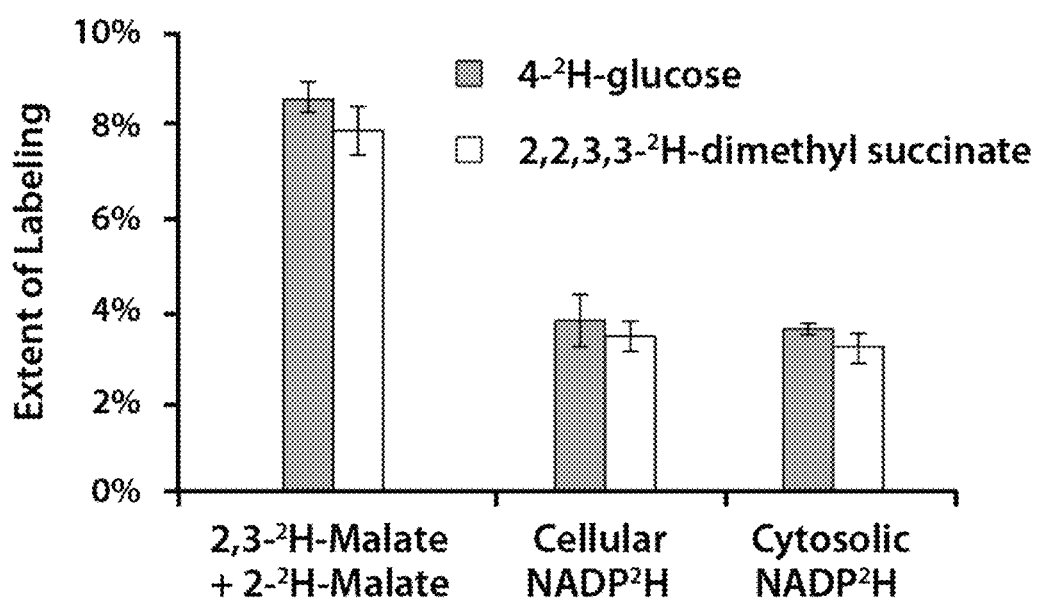

FIG. 23A-23D relate to the tracing of hydride flux of the deuterium atoms of 4-$^2$H-glucose through malic enzyme. FIG. 23A shows a schematic of 4-$^2$H-glucose metabolism. Catabolism of 4-$^2$H-glucose via glycolysis labels cytosolic NADH at the glyceraldehyde-3-phosphate dehydrogenase step. The labeled hydride can then be transferred to malate position 2 via malate dehydrogenase. Hydride at malate position 2 is transferred to NADPH via malic enzyme. FIG. 23B shows the NADP(H) $^2$H-labeling in cells fed 4-$^2$H-glucose for 24 h. FIG. 23C shows palmitate $^2$H-labeling in cells fed 4-$^2$H-glucose for 5 days. FIG. 23D shows the extent of $^2$H-labeling of malate, aspartate, whole cell NADPH, and cytosolic NADPH (inferred from fatty acid labeling) in differentiating 3T3-L1 adipocytes fed 4-$^2$H-glucose (labeling duration 24 h except for the fatty acids).

Figure 24:
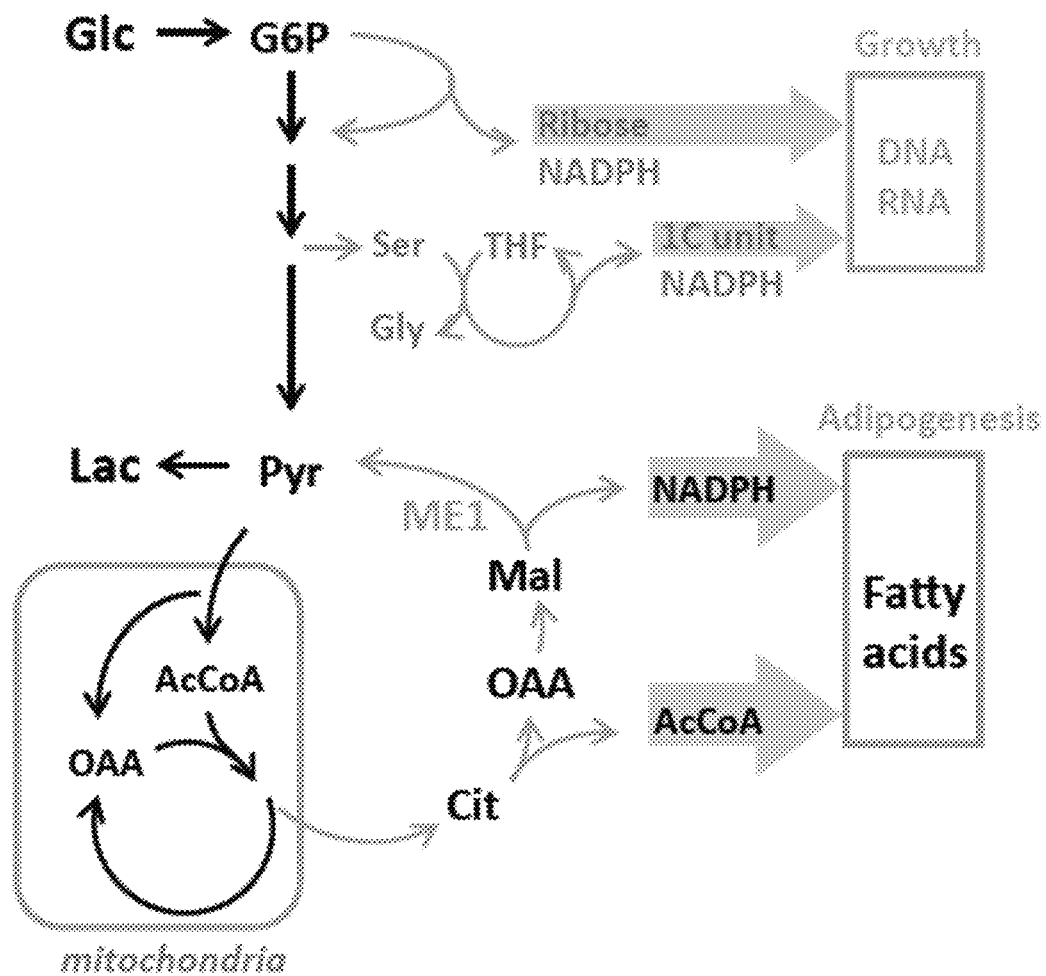

FIG. 24 shows a schematic of a pyruvate-citrate cycle driven by ME1 to promote fatty acid synthesis.

Figure 25:
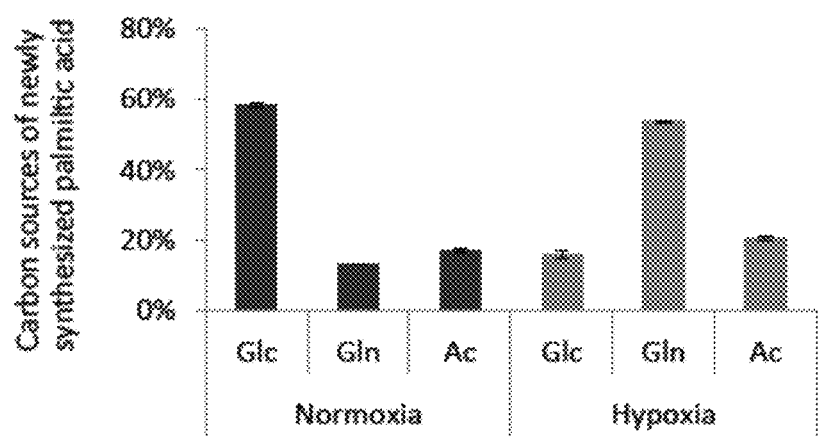

FIG. 25 shows the acetyl-group sources of newly synthesized palmitic acid in differentiating normoxic or hypoxic 3T3-L1 cells (day 5).

FIG. 26, Panels A-D show that hypoxia increases adipocyte NADPH production by the oxidative pentose phosphate pathway and blocks production by malic enzyme. Panel A: Labeling of palmitate in 3T3-L1 adipocytes fed 1-$^2$H-glucose to trace cytosolic NADPH production by the oxPPP. Panel B: Labeling of palmitate in 3T3-L1 adipocytes fed 4-$^2$H-glucose or 2,2,3,3-$^2$H-dimethyl succinate to trace cytosolic NADPH production by malic enzyme. Cells were cultured throughout the 5-day differentiation period in the presence of tracer and either ambient oxygen or 1% $O_2$. Panel C: Summary of metabolic activity in differentiating normoxic or hypoxic adipocytes, showing disruption of the citrate-pyruvate cycle in hypoxia and its replacement by reductive carboxylation, with concomitant shift away from NADPH production by malic enzyme. Panel D: Quantitative comparison of NADPH production routes in differentiating normoxic or hypoxic adipocytes. Data are mean±s.d., n=3.

DETAILED DESCRIPTION OF THE INVENTION

Cells employ two fundamental energy currencies: high-energy phosphate bonds and high-energy electrons. High-energy phosphate bonds in the form of ATP are produced in significant quantities by only two routes: glycolysis and oxidative phosphorylation, with glycolysis providing a significant ATP source specifically when oxygen is limited. High-energy electrons in the form of NADPH, in contrast, can be produced by a variety of pathways.

The present invention relates to the recognition of a 10-formyl-THF pathway for producing NADPH, and to the use of that recognition in the diagnosis and treatment of cancer and metabolic disease, in the development of new antineoplastic agents and/or regimens, in the development of new methods for measuring metabolic pathway activity, and in the development of new therapeutics for treating metabolic disease (Fan, K. et al. (2014) "*Quantitative Flux Analysis Reveals Folate Dependent NADPH Production,*" Nature 510(7504):298-302, herein incorporated by reference in its entirety).

One important NADPH producing enzyme is malic enzyme. Despite significant interest in malic enzyme's role in cancer (Rosen, E. D. et al. (2006) "*Adipocyte Differentiation From The Inside Out,*" Nat. Rev. Mol. Cell Biol. 7:885-896) and obesity (Al-Dwairi, A. et al. (2012) "*Cytosolic Malic Enzyme 1 (ME1) Mediates High Fat Diet-Induced Adiposity, Endocrine Profile, And Gastrointestinal Tract Proliferation-Associated Biomarkers In Male Mice,*" PLoS One 7, e46716 (2012); Lee, C. Y. et al. (1980) "*Identification And Biochemical Analysis Of Mouse Mutants Deficient In Cytoplasmic Malic Enzyme,*" Biochemistry 19:5098-5103), isotope tracer studies had demonstrated significant malic enzyme activity in only a few cell types, notably SF188 glioblastoma cells (DeBerardinis, R. J. et al. (2007) "*Beyond Aerobic Glycolysis: Transformed Cells Can Engage In Glutamine Metabolism That Exceeds The Requirement For Protein And Nucleotide Synthesis,*" Proc. Natl. Acad. Sci. (U.S.A.) 104:19345-19350), and had not conducted controls to rule out alternative pathways between malate and pyruvate (e.g., via PEPCK). Although recent work observed NADH and NADPH labeling from 4-$^2$H-glucose, the NADPH labeling was attributed to an unknown mechanism rather than malic enzyme. No prior study has specifically traced NADPH-dependent malic enzyme.

Herein, two exemplary tracers are provided for this purpose: 2,2,3,3-$^2$H-dimethyl succinate and 4-$^2$H-glucose. The two exemplary tracers are complementary: production of labeled malate by 2,2,3,3-$^2$H-dimethyl succinate is more direct, but relies on a non-physiologic uptake mechanism and transfer of malate from mitochondrion to cytosol. In contrast, 4-$^2$H-glucose uses a physiological uptake mechanism and sequence of cytosolic reactions to label malate. As glucose is the most important circulating carbon source, 4-$^2$H-glucose is well suited to in vivo application, particularly for the diagnosis and prognosis of metabolic diseases such as obesity and diabetes, for the diagnosis and prognosis of cancer and for the assessment of normoxia/hypoxia, in a subject.

Importantly, the results obtained with the two exemplary tracers provided herein are in quantitative agreement in examples where application of both is scientifically appropriate: a malic enzyme contribution to cytosolic NADPH in differentiating (day 5) 3T3-L1 adipocytes of roughly 60% in normoxia and 3% in hypoxia.

A. Nomenclature

As used herein, the terms "subject" and "patient" refer to an animal (e.g., a bird, a reptile or a mammal), preferably a mammal including a non-primate (e.g., a camel, donkey, zebra, cow, pig, horse, goat, sheep, cat, dog, rat or mouse) and a primate (e.g., a monkey, chimpanzee, or a human) and, most preferably, a human.

An atom of glucose or any of its derivatives is described hereon with reference to the carbon backbone of D-glucose molecule, with carbon atoms being numbered from 1 to 6, starting from the carbonyl carbon. Thus, for example, reference to "3-H" denotes a hydrogen atom pendant from the carbon that corresponds to carbon 3 of the D-glucose backbone. Likewise, reference to "C1," "C2," etc. with respect to a molecule denotes the first, second, etc. carbon atom of that molecule. Reference to "1-$^{14}$C" or "6-$^{14}$C" of a molecule denotes a $^{14}$C-labeled carbon atom corresponding, respectively, to carbon 1 or carbon 6 of that molecule. Reference to "U" in the context of labeling denotes compounds that are uniformly or randomly labeled.

An atom of the amino acids serine and glycine is likewise described with reference to the carbon backbone of such molecules, with carbon atoms being numbered from 1 to 3 (for serine) or 1 to 2 for glycine, with the carboxylic carbon being designated as carbon 1 (i.e., 1-C). Thus, for example, "3-$^2$H-serine" denotes a serine molecule that has been labeled with deuterium ($^2$H) at serine carbon 3 (the carbon furthest from the a-carboxy carbon). Similarly, "2,3,3-$^2$H-serine" denotes a serine molecule that has been labeled with three deuterium atoms, one of which is pendant from serine carbon 3 and two of which are pendant from serine carbon 3. Similarly, "3,3-$^2$H-serine" denotes a serine molecule that has been labeled with two deuterium atoms, both being pendant from serine carbon 3. Likewise, "4-$^2$H-glucose" denotes a glucose molecule that has been labeled with deuterium ($^2$H) (i.e., "deuterated") at glucose carbon 4.

As used herein, a molecule that comprises "deuteration" or has been "deuterated" at a recited carbon atom is intended to denote that at least one of the hydrogen atoms pendant from such carbon atom is deuterium. Thus, for example, the phrase "a serine molecule that comprises deuteration at serine carbon C-3" is intended to denote a serine molecule in which at least one of the 3-C serine hydrogens is $^2$H (for example, 3-$^2$H-serine; 2,3-$^2$H-serine, 2,3,3-$^2$H-serine, U-$^2$H-serine (uniformly labeled with $^2$H).

A biomolecule that contains a single labeled deuterium atom is referred to herein as being "M+1" (i.e., mass of the biomolecule+1, with the "1" being the differential weight of deuterium ($^2$H) relative to hydrogen ($^1$H)). A biomolecule that contains a two labeled deuterium atoms is thus referred to herein as being "M+2," etc.

The term "fatty acid moiety" refers to a carboxylic acid group (HO—C(O)—) bonded to a saturated or unsaturated aliphatic chain (R) (i.e., HO—C(O)—R). The term "thymine moiety" refers to a 5-methylpyrimidine-2,4(1H,3H)-dione group. Examples of molecules comprising a thymine moiety include thymidine, thymidine, thymidine triphosphate, thymidine diphosphate, thymidine monophosphate, DNA, etc. The term "formate moiety" refers to a methanoate group —OC(O)H). Examples of molecules comprising a formate moiety include formate esters (e.g., ROC(O)H) such as ethyl formate, methyl formate, triethyl orthoformate, trimethyl orthoformate, etc.). The term "glycine" refers to $NH_2CH_2COOH$. The term "purine" refers a heterocyclic aromatic organic compound that comprises a pyrimidine ring fused to an imidazole ring (e.g., adenine, caffeine, guanine, uric acid, xanthine, etc.). A "pyrimidine" is a 6 membered heterocyclic diazine having nitrogen atoms at positions 1 and 3 in the ring (e.g., cytosine, thymine, uracil, etc.). An "imidazole" is a five membered ring having nitrogen atoms at positions 1 and 3 in the ring.

The term "anti-folate anticancer agent" is intended to refer to a compound that is an inhibitor of an enzyme of folate metabolism, for example, an inhibitor of dihydrofolate reductase (DHFR), an inhibitor of β-glycinamide ribonucleotide transformylase (GARFT), an inhibitor of 5 '-amino-4'-imidazolecarboxamide ribonucleotide transformylase (AICARFT), an inhibitor of thymidylate synthetase (TYMS), an inhibitor of methylene tetrahydrofolate dehydrogenase 1 or 2 (MTHFD1 or MTHFD2), an inhibitor of serine hydroxymethyltransferase 1 or 2 (SHMT1 or SHMT2), formyltetrahydrofolate dehydrogenase 1 or 2 (ALDH1L1 or ALDH1L2), etc. In one embodiment, such anti-folate anticancer agents may be structural analogues of a folate pteroylglutamate. Examples of anti-folate anticancer agents include 2,4-diamino-pteroylglutamate (4-amino-folic acid; Aminopterin or "AMT"), its 10-methyl congener, methotrexate ("MTX"), Tomudex (D1694, raltitrexed), Pemetrexed (Alimta, Eli Lilly), Pralatrexate (PDX; 10'-propargyl 10'-deazaaminopterin), Lometrexol (LMTX), Edatrexate (EDX), Talotrexin (PT-523), TMQ, Piritrexim (PTX), Nolatrexed (Thymitaq, TM), etc. (see, e.g., Hagner, N. et al. (2010) *Cancer Chemotherapy: Targeting Folic Acid Synthesis*," Cancer Manag. Res. 2:293-301; Surmont, V. F. et al. (2011) "*Raltitrexed in Mesothelioma*," Expert Rev. Anticancer Ther. 11(10):1481-1490; Tomao, F. et al. (2009) "*Emerging Role Of Pemetrexed In Ovarian Cancer*," Expert Rev. Anticancer Ther. 9(12):1727-1735; Joerger, M. et al. (2010) "*The Role Of Pemetrexed In Advanced Non Small-Cell Lung Cancer: Special Focus On Pharmacology And Mechanism Of Action*," Curr. Drug Targets 11(1):37-47; Calvert, A. H. (2004) "*Biochemical Pharmacology Of Pemetrexed*," Oncology (Williston Park) 18(13 Suppl 8):13-17; McGuire, J. J. (2003) "*Anticancer Antifolates: Current Status And Future Directions*," Curr. Pharm. Des. 9(31): 2593-2613). As used herein, the term "anti-folate anticancer agent" also refers to prodrugs of folate inhibitors, for example, formate esters thereof.

B. Measurement of NADPH Production

Past examination of NADPH production during cell growth has analyzed metabolic fluxes in cells using $^{13}$C and $^{14}$C isotope tracers (Lee, W. N. et al. (1998) *Mass Isotopomer Study Of The Nonoxidative Pathways Of The Pentose Cycle With [1,2-$^{13}$C2]Glucose*," Am. J. Physiol. 274:E843-E851; Metallo, C. M. et al. (2009) "*Evaluation Of $^{13}$C Isotopic Tracers For Metabolic Flux Analysis In Mammalian Cells*," J. Biotechnol. 144:167-174; Fan, T. W. et al. (2008) "*Rhabdomyosarcoma Cells Show An Energy Producing Anabolic Metabolic Phenotype Compared With Primary Myocytes*," Mol. Cancer 7:79 (pages 1-20); Brekke, E. M. et al. (2012) "*Quantitative Importance Of The Pentose Phosphate Pathway Determined By Incorporation Of $^{13}$C From [2-$^{13}$C]-And [3-$^{13}$C]Glucose Into TCA Cycle Intermediates And Neurotransmitter Amino Acids In Functionally Intact Neurons*," J. Cereb. Blood Flow Metab. 32:1788-1799).

For NADPH metabolism, however, carbon tracers alone are insufficient, because they cannot determine whether a particular redox reaction is making reduced nicotinamide adenine dinucleotide ("NADH") versus NADPH or the reaction's fractional contribution to total cellular NADPH production. To address these limitations, a deuterium ($^2$H) tracer approach was developed and used in conjunction with improved methods for analyzing $^{13}$C labeling.

In a preferred method, the biomass fraction (normalized to packed cell volume) of DNA (DNA assay kit, Life Technologies), total protein (DC protein assay kit, Bio-Rad), proline (LC-MS), and fatty acids (LC-MS) are determined. Then, for each component, the relative contribution of different acquisition routes (e.g. biosynthesis versus uptake) is measured. The resulting total NADPH consumption is given by:

$$NADPH \text{ Consumption} = \sum_i \left(\frac{\text{Product } i}{PCV}\right) * \left(\frac{NADPH \text{ Consumed}}{\text{Product } i}\right) * \text{Growth Rate} \quad \text{(Equation 1)}$$

For the differentiating cells, because growth rate is not well-defined and biomass composition is changing, we instead inferred DNA synthesis based on rate of increase in cell number (which was negligible by day 5) and measured directly the rate of increase in protein and fat:

$$NADPH \text{ Consumption} = \sum_i \left(\frac{\text{Newly Synthesized Product } i}{PCV}\right) * \left(\frac{NADPH \text{ Consumed}}{\text{Product } i}\right) \quad \text{(Equation 2)}$$

Taking NADPH consumed by fatty acid biosynthesis, for example, one corrects for newly synthesized fatty acid based on $^{13}$C-enrichment from U-$^{23}$C-glucose and U-$^{23}$C-glutamine. For each fatty acid species, its unlabeled fraction comes either from pre-existing fat (synthesized or taken up before the labeling began) or fat taken up directly from serum in the medium; neither of these consume NADPH. Since only the fraction of fatty acid newly synthesized from 2C units during the labeling interval uses NADPH, the amount of a newly synthesized fatty acid species (palmitate for example) where labeling fractions are [M+0], [M+1], etc. is given by:

Newly Synthesized Palmitate = (Equation 3)

$$\text{Palmitate Amount} * \sum_{i=1}^{16} \frac{[M+i]}{16}$$

Figure 1A:
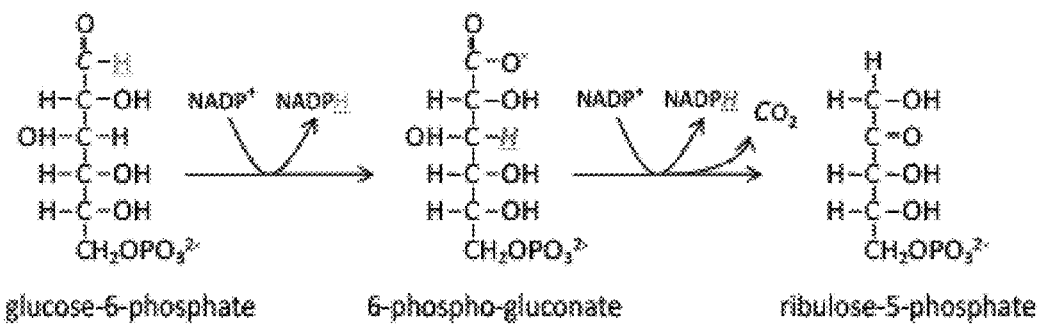
FIGS. 1A-1H show the quantitation of NADPH labeling via oxPPP and of total cytosolic NADPH production.

C. Preferred Methods for the Measurement of NADPH Redox-Active Hydrogen Labeling A deuterium tracer approach was developed that directly measures NADPH redox-active hydrogen labeling. To probe the oxPPP, cells were shifted from unlabeled to 1-$^2$H-glucose or 3-$^2$H-glucose (FIG. 1A) and the resulting NADP+ and NADPH labeling was measured using liquid chromatography-mass spectrometry (Lu, W. et al. (2010) "*Metabolomic Analysis Via Reversed-Phase Ion-Pairing Liquid Chromatography Coupled To A Stand Alone Orbitrap Mass Spectrometer*," Analytical Chemistry 82:3212-3221). $^2$H-labeling may be similarly used to directly observe NADPH production by other pathways by providing other labeled compounds. Exemplary compounds include: 2,3,3-$^2$H-aspartate; 1-$^2$H-citrate; 2,2-$^2$H-citrate; 2,2,4,4-$^2$H-citrate; 1-$^2$H fructose-6-phosphate; 3-$^2$H fructose-1,6-biphosphate; 1-$^2$H glucose-6-phosphate; 2,3,3,4,4-$^2$H-glutamate; 2,3,3,4,4-$^2$H-glutamine; 1,2,3-$^2$H-malate; 2,2,3-$^2$H-malate; 2,2-$^2$H-oxaloacetate; 3-$^2$H 6-phospho-gluconate; 2,3,3-$^2$H-serine; 3,3-$^2$H-serine; 1-$^2$H-glucose, 2-$^2$H-glucose, 3-$^2$H-glucose, 4-$^2$H-glucose, 5-$^2$H-glucose, 6-$^2$H-glucose, etc. Uptake of the labeled compound may be facilitated by permeabilizing the cells (Aragón, J. J. et al. (1980) "*Permeabilization Of Animal Cells For Kinetic Studies Of Intracellular Enzymes: In Situ Behavior Of The Glycolytic Enzymes Of Erythrocytes*," Proc. Natl. Acad. Sci. (U.S.A.) 77(11):6324-6328), or a cell-free system may be used (Stoecklin, F. B. et al. (1986) "*Formation Of Hexose 6-Phosphates From Lactate-Pyruvate+Glutamate By A Cell-Free System From Rat Liver*," Biochem J. 236(1):61-70). Because labeling of glycolytic and oxPPP intermediates and the redox active hydride of NADPH reaches steady state over approximately 5 min, where for TCA intermediates this can take several hours, and for amino acids yet longer, to ensure steady-state labeling, oxPPP tracing with 1-2H-glucose and 1,2-13C-glucose is performed for a minimum of 30 min and other labeling experiments for a minimum of 12 h.

Figure 1B:
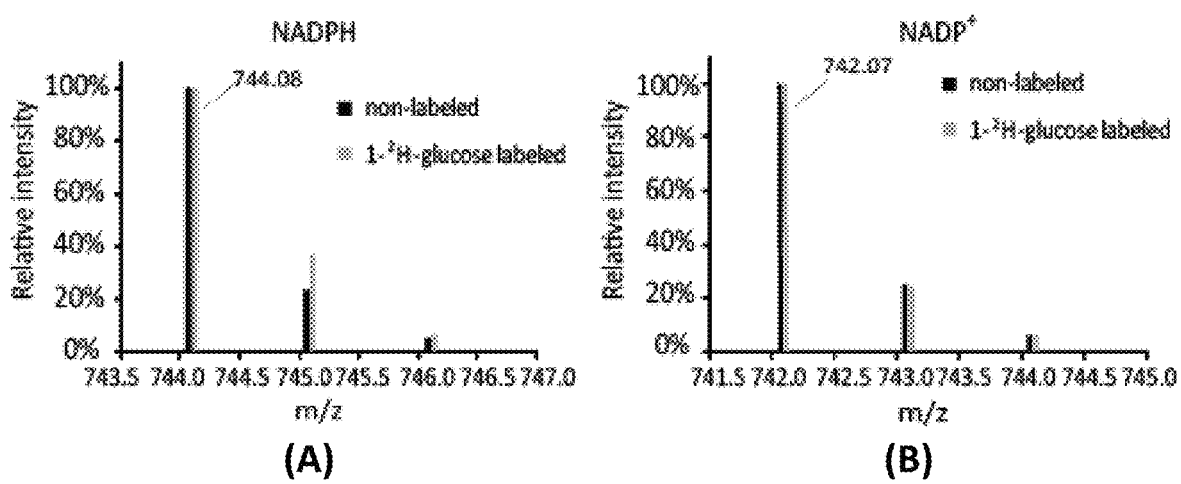
Figure 1C:
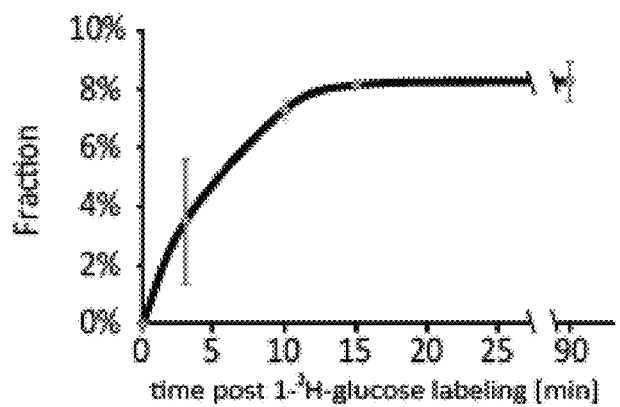
Figure 1D:
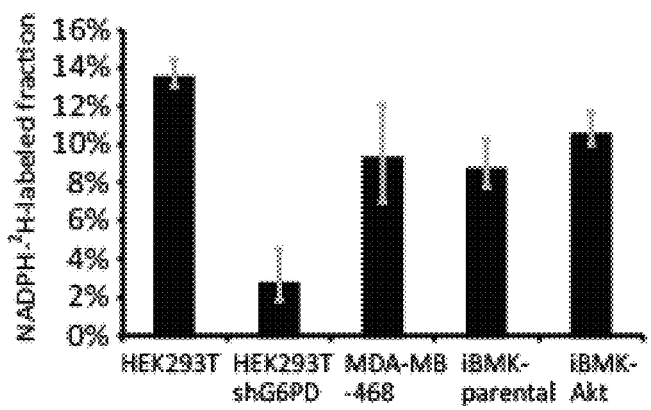
Figure 1E:
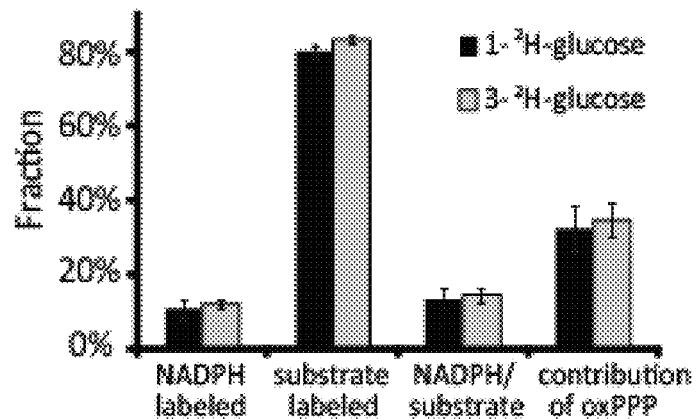
Figure 1F:
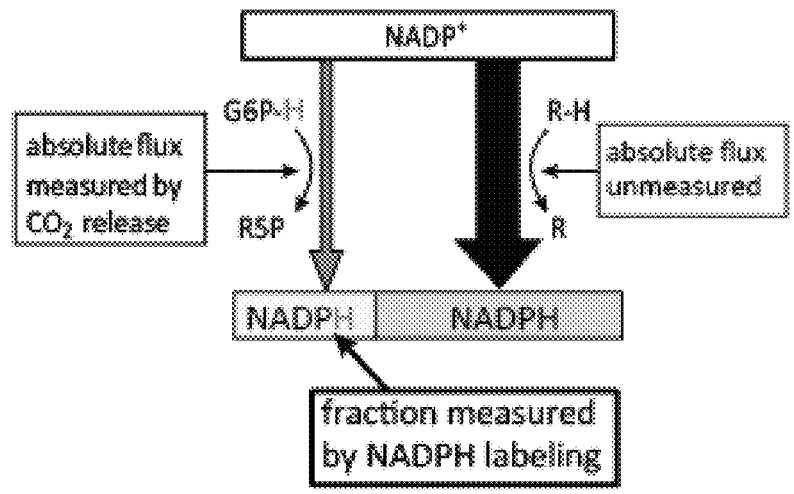

As shown in FIG. 1F, the total pool of NADPH comprises molecules produced through the addition of a hydrogen atom from glucose-6-phosphate ("G6P") via a cytosolic glycolysis reaction that yields ribulose-5-phosphate:

and $CO_2$, and molecules produced through the reduction of NADP to NADPH via other reactions. Since most NADPH production is cytosolic (Circu, M. L. et al. (2011) "*Disruption Of Pyridine Nucleotide Redox Status During Oxidative Challenge At Normal And Low-Glucose States: Implications For Cellular Adenosine Triphosphate, Mitochondrial Respiratory Activity, And Reducing Capacity In Colon Epithelial Cells*," Antioxid. Redox Signal 14:2151-2162), $^2$H-glucose labeling results can be used to quantitate the fractional contribution of the oxPPP to total cytosolic NADPH production:

$$\text{Fraction}_{NADPH \text{ from } oxPPP} = \frac{2 \times (NADP^2H/\text{Total } NADPH)}{(^2H\text{-}G6P/\text{Total}G6P)} \times C_{KIE}$$ (Equation 4)

wherein the parenthetical terms are the fractional $^2$H-labeling of NADPH's redox-active hydrogen and the fractional $^2$H-labeling of glucose-6-phosphate (G6P)'s targeted hydrogen (i.e., the H pendant from the 1-C carbon of G6P) (FIG. 1E, FIGS. 5B-5D). The term $C_{KIE}$ accounts for the deuterium kinetic isotope effect (Shreve, D. S. et al. (1980) "*Kinetic Mechanism Of Glucose-6-Phosphate Dehydrogenase From The Lactating Rat Mammary Gland. Implications For Regulation*," J. Biol. Chem. 255:2670-2677; Price, N. E. et al. (1996) "*Kinetic And Chemical Mechanisms Of The Sheep Liver 6-Phosphogluconate Dehydrogenase*," Arch. Biochem. Biophys. 336:215-223) (FIGS. 5E-5G). Correction for the deuterium kinetic isotope effect was based on the assumption that total metabolic fluxes are not impacted. This correction was used as the default herein.

Let x be the fractional labeling of the relevant substrate hydrogen, $F_U$ be the NADPH production flux from unlabeled substrate and $F_L$ be the NADPH production flux from the labeled substrate, then:

$$\frac{F_L}{F_U} = \frac{x/(V_H/V_D)}{1-x}$$ (Equation 5)

$$F_{reaction} = F_L + F_U = F_L \frac{V_H/V_D + x(1 - V_H/V_D)}{x}$$ (Equation 6)

wherein $F_L/x$ is the flux in cases without a discernible kinetic isotope effect (e.g., for $^{13}$C). The remaining term is the correction factor for the kinetic isotope effect:

$$C_{KIE} = V_H/V_D + x(1 - V_H/V_D)$$ (Equation 7)

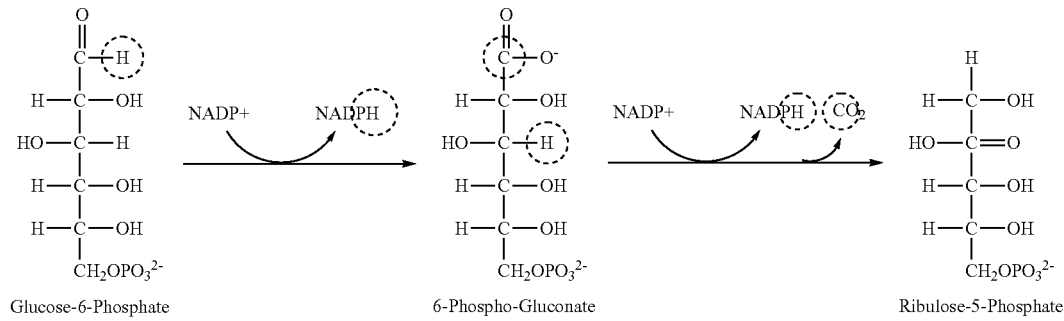

Glucose-6-Phosphate     6-Phospho-Gluconate     Ribulose-5-Phosphate

Alternatively, the largest reasonable correction for the deuterium kinetic isotope effect is based on the assumption that pathway flux is decreased by the introduction of $^2$H-labeled tracer equivalent to the decrease in activity of the associated enzyme observed in vitro:

$$C_{KIE} = \frac{V_H/V_D}{1 + N \times (V_H/V_D - 1) \times X_{NADPH}} \quad \text{(Equation 8)}$$

where N is the number of NADPH produced per substrate molecule passing through the pathway. For the oxPPP, N=2. Note that the impact of the kinetic isotope effect on NADP$^2$H production may be partially offset by an analogous (albeit smaller) kinetic isotope effect in NADP$^2$H consuming reactions. VH/VD for fatty acid synthetase is approximately 1.1 (Yuan, Z. et al. (1984) "*Elementary Steps In The Reaction Mechanism Of Chicken Liver Fatty Acid Synthase. pH Dependence Of NADPH Binding And Isotope Rate Effect For Beta-Ketoacyl Reductase*," J. Biol. Chem. 259:6748-6751). The impact of different mechanisms of correcting for the deuterium kinetic isotope is shown in FIGS. 5A-5G.

The kinetic isotope effect ($V_H/V_D$) for isolated NADPH-producing enzymes ranges from 1.8-4, with isolated G6PD and 6-phosphogluconate dehydrogenase having a $V_H/V_D$=1.8 (Shreve, D. S. et al. (1980) "*Kinetic Mechanism Of Glucose-6-Phosphate Dehydrogenase From The Lactating Rat Mammary Gland. Implications For Regulation*," J. Biol. Chem. 255:2670-2677; Price, N. E. et al. (1996) "*Kinetic And Chemical Mechanisms Of The Sheep Liver 6-Phosphogluconate Dehydrogenase*," Arch. Biochem. Biophys. 336:215-223). However, cellular homeostatic mechanisms (including flux control being distributed across multiple pathway enzymes) may result in a lesser impact on labeling patterns in cells.

The fractional NADPH redox-active site labeling (x) was measured from the observed NADPH and NADP+ labeling patterns from the same sample. x was calculated to best fit the steady-state mass distribution vectors of NADPH and NADP+ (MNADPH and MNADP+) by least square fitting in MATLAB (function: lsqcurvefit).

$$M_{NADP+} = \begin{bmatrix} m_0 \\ m_1 \\ m_2 \\ \vdots \\ m_N \end{bmatrix} \begin{matrix} M+0 \\ M+1 \\ M+2 \\ \\ M+N \end{matrix} \quad \text{(Equation 9)}$$

$$M_{NADPH} = \begin{bmatrix} m_0 \times (1-x) \\ m_1 \times (1-x) + m_0 \times x \\ m_2 \times (1-x) + m_1 \times x \\ \vdots \\ m_N \times (1-x) + m_{N-1} \times x \\ m_N \times x \end{bmatrix} \begin{matrix} M+0 \\ M+1 \\ M+2 \\ \\ M+N \\ M+N+1 \end{matrix}$$

D. Preferred Methods for Deducing the Total Cytosolic NADPH Production Rate

The inferred fractional contribution of oxPPP to NADPH production can be used to deduce the total cytosolic NADPH production rate, which is equal to the absolute oxPPP flux divided by the fractional contribution of oxPPP to NADPH production (FIG. 1F).

A first method for achieving this goal involves measuring $^{14}CO_2$ release from 1-$^{14}$C-glucose versus 6-$^{14}$C-glucose (FIG. 6A-6C, FIG. 7A-7F). Since oxPPP converts glucose-6-phosphate to a phospho-pentose by removing carbon 1, use of 6-$^{14}$C-glucose (in which glucose carbon 6 is labeled) will not lead to the evolution of any labeled $^{14}CO_2$, whereas use of 1-$^{14}$C-glucose (in which glucose carbon 1 is labeled) results in the evolution of labeled $^{14}CO_2$ for glucose molecules that enter the oxPPP. Conversely, glycolysis of both 1-$^{14}$C-glucose and 6-$^{14}$C-glucose yields pyruvate, which then, via the TCA cycle, leads to the evolution of $CO_2$. Thus, by measuring the ratios of $^{14}CO_2$ released using 1-$^{14}$C-glucose or 6-$^{14}$C-glucose, one can determine the relative ratios of oxPPP and glycolytic processing of glucose.

$$\text{Fraction}_{NADPH\,from\,oxPPP} = 2 \times (\text{Fraction}_{CO_2\,from\,Glucose\,C1} - \text{Fraction}_{CO_2\,from\,Glucose\,C6}) \quad \text{(Equation 10)}$$

A second method for achieving this goal involves measuring the kinetics of 6-phosphogluconate labeling from U-$^{13}$C-glucose (FIGS. 6D-6F). U-$^{13}$C-glucose is converted, via oxPPP, into 6-phosphogluconate in a reaction that produces NADPH. Thus, for example, by monitoring the reduction in the percentage of unlabeled 6-phosphogluconate over time after provision of labeled U-$^{13}$C-glucose, one can calculate the contribution of oxPPP to NADPH production.

To quantify the absolute oxPPP flux, cells are switched to media containing U-$^{13}$C-glucose, and the kinetics glucose-6-phosphate and 6-phosphogluconate labeling were measured. Most preferably for such an analysis, cells are grown in Dulbecco's Modified Eagle's Medium (DMEM) without pyruvate (CELLGRO) with 10% dialyzed fetal bovine serum (Invitrogen) in 5% $CO_2$ at 37° C. and harvested at approximately 80% confluency. Preferably, for metabolite measurements, metabolism was quenched and metabolites were extracted by aspirating media and immediately adding −80° C. 80:20 methanol:water. Supernatants from two rounds of extraction were combined, dried under $N_2$, resuspended in water, placed in a 4° C. autosampler, and analyzed within 6 h by reversed-phase ion-pairing chromatography negative mode electrospray ionization high-resolution MS on a standalone orbitrap (Thermo) (Lu, W. et al. (2010) "*Metabolomic Analysis Via Reversed-Phase Ion-Pairing Liquid Chromatography Coupled To A Stand Alone Orbitrap Mass Spectrometer*," Analytical Chemistry 82:3212-3221). Fluxes from $^{14}$C-labeled substrates to $CO_2$ were measured by adding trace $^{14}$C-labeled nutrient to normal culture media, quantifying the radioactive $CO_2$ released (Folger, O. et al. (2011) "*Predicting Selective Drug Targets In Cancer Through Metabolic Networks*," Mol. Syst. Biol. 7:501 (pages 1-10), and correcting for intracellular substrate labeling according to the percentage of radioactive tracer in the media and the fraction of particular intracellular metabolite deriving from media uptake, as measured using $^{13}$C-tracer.

The unlabeled fraction of 6-phosphoglucanate decays with time as:

$$\frac{d[6-\text{phosphogluconate}]^{unlabeled}}{dt} = \quad \text{(Equation 11)}$$
$$-F_{oxPPP} \frac{[6-\text{phosphogluconate}]^{unlabeled}}{[6-\text{phosphogluconate}]^{total}} + F_{oxPPP} \times \text{Fraction}_{G6P}^{Unlabeled}(t)$$

wherein $F_{oxPPP}$ is the flux of oxPPP, [6-phosphogluconate]$^{total}$ is the total cellular 6-phosphogluconate concentration, which was directly measured, and Fraction$_{G6P}^{Unlabeled}(t)$ is the unlabeled fraction of glucose-6-phosphate at time t, which decays exponentially. $F_{oxPPP}$ is preferably obtained by lease square fitting (see, Yuan, J. et al. (2008) "*Kinetic Flux Profiling For Quantitation Of Cellular Metabolic Fluxes,*" Nat. Protoc. 3:1328-1340).

Figure 1G:
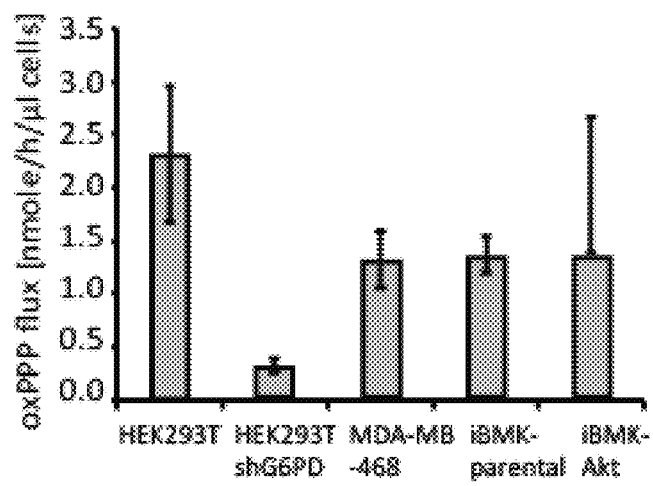
Figure 1H:
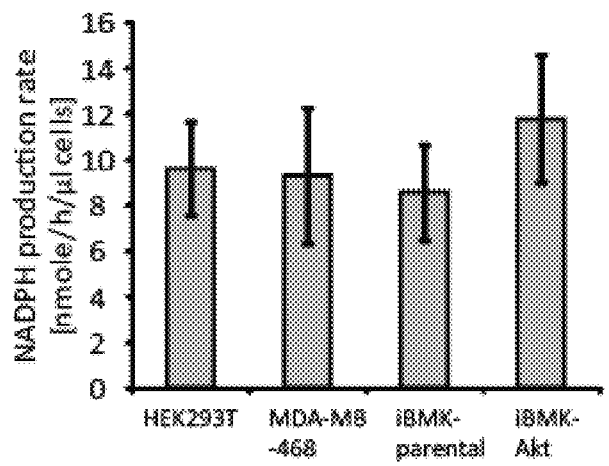

Both methods gave consistent fluxes with the radioactive measurement more precise (FIG. 6G). As confirmation of its specificity, elimination of glucose-6-phosphate dehydrogenase (via knock down) resulted in markedly reduced oxPPP $^{14}CO_2$ release, as expected (FIG. 1G). Suitable knockdown cell lines may be generated using an shRNA-expressing lentivirus (see, e.g., Alimperti, S. et al. (2012) "*A Novel Lentivirus For Quantitative Assessment Of Gene Knockdown In Stem Cell Differentiation,*" Gene. Ther. 19(12): 1123-1132) with puromycin selection. IDH1, IDH2 and ALDH1L2 knockdowns were generated by transfecting cells with siRNA. Knockdown was confirmed by Western blot (see FIGS. 14A-14G). In the absence of such knockdown, the oxPPP flux observed with some transformed cell lines ranged from 1-2.5 nmol $\mu L^{-1}$ $h^{-1}$ (where volume is the packed cell volume; FIG. 1G). This flux is similar to, but slightly less than, the cellular ribose demand (FIG. 7F). In combination with the fractional NADPH labeling, a total cytosolic NADPH production rate of approximately 10 nmol $uL^{-1}$ $h^{-1}$ (FIG. 1H) was determined using proliferating cells, which is 5-20% of the glucose uptake rate.

E. Identification and Analysis of NADPH-Producing Tetrahydrofolate Pathway (The "10-Formyl-THF Pathway")

A genome-scale human metabolic model (Duarte, N. C. et al. (2007) "*Global Reconstruction Of The Human Metabolic Network Based On Genomic And Bibliomic Data,*" Proc. Natl. Acad. Sci. (U.S.A.) 104:1777-1782) was used in order to identify other potential NADPH-producing pathways. The model is biochemically, genetically, and genomically structured and accounts for the functions of 1,496 ORFs, 2,004 proteins, 2,766 metabolites, and 3,311 metabolic and transport reactions.

Preferably, the model is constrained based on the observed steady-state growth rate, biomass composition, and metabolite uptake and excretion rates of cancer cells without enforcing any constraints on NADPH production routes. The flux balance equations were solved in MATLAB with the objective function formulated to minimize the total sum of fluxes (Folger, O. et al. (2011) "*Predicting Selective Drug Targets In Cancer Through Metabolic Networks,*" Mol. Syst. Biol. 7:501 (pages 1-10).

NADPH consumption by reductive biosynthesis is preferably determined based on reaction stoichiometries, experimentally measured cellular biomass composition, growth rate, fractional de novo synthesis of fatty acids (by $^{13}C$-labeling from U-$^{23}C$-glucose and U-$^{23}C$-glutamine), and fractional synthesis of proline from glutamate versus arginine (by $^{13}C$-labeling from U-$^{23}C$-glutamine).

This approach may be applied to a wide diversity of cell lines and other cells in culture, including immortalized baby mouse kidney cells (iBMK-parental cells) (Degenhardt, K. et al. (2002) "*BAX And BAK Mediate P53-Independent Suppression Of Tumorigenesis,*" Cancer Cell 2:193-203). Similar results are obtained with many different transformed and/or cancerous proliferating cell lines.

Figure 2A:
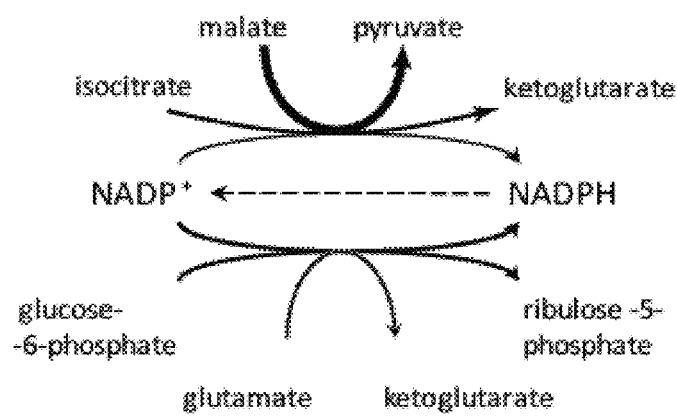
FIGS. 2A-2F show pathways contributing to NADPH production.
Figure 2B:
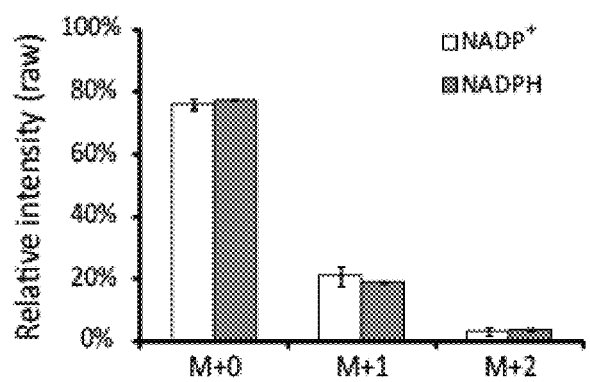
Figure 2C:
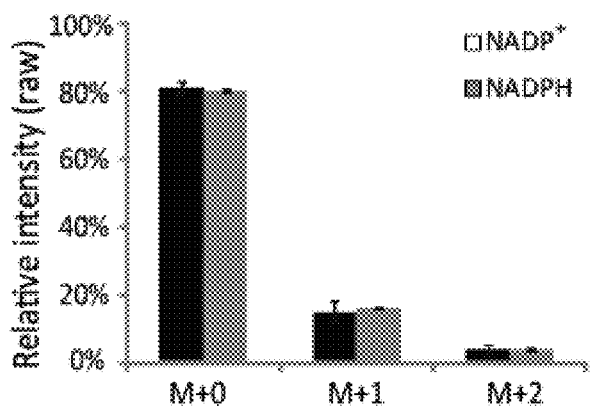
Figure 2D:
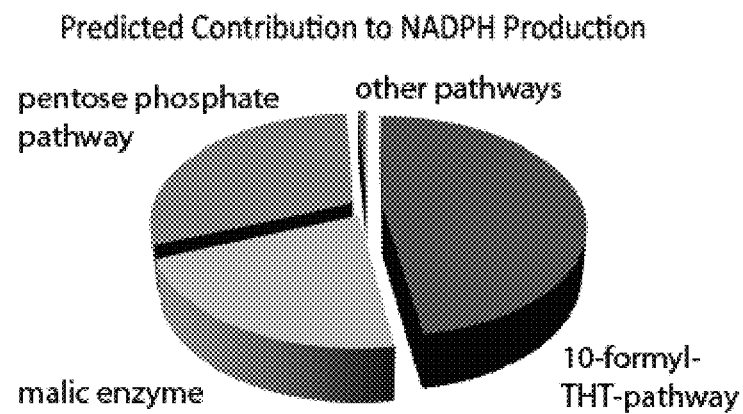

The model, assessed via flux balance analysis with an objective of minimizing total enzyme expression requirements and hence flux (Folger, O. et al. (2011) "*Predicting Selective Drug Targets In Cancer Through Metabolic Networks,*" Mol. Syst. Biol. 7:501 (pages 1-10), predicted that both the oxPPP and malic enzyme contribute approximately 30% of NADPH (FIG. 2D). Surprisingly, however, an even greater percentage (approximately 40%) of NADPH production was predicted to come from a mitochondrial folate-dependent pathway (FIG. 3A)

In this mitochondrial pathway (the "10-formyl-THF mitochondrial pathway"), serine is converted to glycine via a reaction catalyzed by mitochondrial serine hydroxymethyltransferase ("shmt2") that transfers serine's 3-C carbon atom to tetrahydrofolate ("THF") thereby producing $N^5, N^{10}$-methylene-tetrahydrofolate ("Methylene-THF"). This reaction is distinct from the reaction, mediated by glycine decarboxylase, that produces methylene-THF from THF by decarboxylating the 2-C of glycine (and generating $CO_2$). Methylene-THF, produced from either reaction, is converted to 10-formyl-tetrahydrofolate ("10-formyl-THF") in a reaction catalyzed by the bifunctional methylene-tetrahydrofolate dehydrogenase/cyclohydrolase, mitochondrial enzyme ("mthfd2") (Peri, K. G. et al. (1989) "*Nucleotide Sequence Of The Human NAD-Dependent Methylene-Tetrahydrofolate Dehydrogenase-Cyclohydrolase,*" Nucleic Acids Res 17(21):8853; Yang, X. M., et al. (1993) "*NAD-Dependent Methylenetetrahydrofolate Dehydrogenase-Methenyltetrahydrofolate Cyclohydrolase Is The Mammalian Homolog Of The Mitochondrial Enzyme Encoded By The Yeast MIS1 Gene*" Biochemistry 32(41):1118-1123). This reaction produces NADH or NADPH. An alternative objective function of maximizing growth rate further predicts a potentially substantial contribution of folate metabolism to NADPH production (FIGS. 9A-9B).

Similar to quantifying relative contribution of oxPPP to cytosolic NADPH production, the contribution of the 10-formyl-THF cytosolic pathway can be estimated from $^2H$-serine labeling as follows:

$$\text{Fraction}_{NADPH(c) \text{ from } MTHFD1} = \frac{NADP^2H(c)}{\text{total } NADP^2H(c)} \times \frac{\text{total serine}}{^2H - \text{serine}} \times C_{KIE}(MTHFD1) \quad \text{(Equation 12)}$$

Existing methods do not allow direct measurement of methylene-THF labeling, but such labeling can be approximated based on intracellular serine labeling (formally, the $^2H$-serine labeling places an upper bound on $^2H$-methylene-THF labeling):

$$\text{Fraction}_{NADPH(c) \text{ from } MTHFD1} \geq \frac{NADP^2H(c)}{\text{total } NADP^2H(c)} \times \frac{\text{total serine}}{^2H - \text{serine}} \times C_{KIE}(MTHFD1) \quad \text{(Equation 13)}$$

wherein MTHFD1 has a deuterium kinetic isotope effect $V_H/V_D$ of approximately 3.

The production of NADPH via a THF cycle is confirmed by Maddocks, O. D. et al. (2014) ("*Localization of NADPH Production: A Wheel within a Wheel,*" Mol. Cell. 17; 55(2): 158-160).

F. Exemplary Method for Measuring $CO_2$ Release and oxPPP Flux in Cell Culture

In one embodiment, $^{14}CO_2$ fluxes are quantified as described by Fan et al. (Fan, J. et al. (2014) "*Quantitative Flux Analysis Reveals Folate Dependent NADPH Production,*" Nature 510:298-302). Briefly, cells are grown in 12.5 $cm^2$ tissue culture flasks with DMEM with low bicarbonate buffer (0.74 g/L) and additional HEPES buffer (6 g/L, pH7.4). $^{14}C$ tracer is added to the media and the flask is sealed with a stopper with a center well (Kimble Chase) containing thick pieces of filter paper saturated with 200 µL 10 M KOH. Cells are incubated for 24 h. Thereafter, 1 mL 3 M acetic acid is added to the culture medium to quench metabolism. Filter paper (and any associated residue) in the center well is collected into liquid scintillation cocktail (PerkinElmer). The signal is corrected for intracellular substrate labelling according to percentage of radioactive tracer in the media, and fraction of particular intracellular metabolite from media uptake, which is measured by $^{13}$C-tracer. The $^{14}$C flux (per packed cell volume per time) after correction is given by:

$$^{14}CO_2 = \frac{^{14}C \text{ Signal}}{\text{Labeling Time} + PCV} * \frac{^{12}C \text{ Signal}}{^{14}C \text{ Tracer}} * \frac{\text{Fraction Medium Nutrient }^{13}C \text{ Labeled}}{\text{Fraction Intracellular Substrate }^{13}C \text{ Labeled}} \quad \text{(Equation 14)}$$

G. Preferred Methods for Analyzing Fat Synthesis to Determine the NADPH Production Rate The most NADPH-demanding biosynthetic activity in mammals is fat synthesis, which consumes a majority of cytosolic NADPH in typical transformed cells in culture (Fan, J. et al. (2014) "*Quantitative Flux Analysis Reveals Folate-Dependent NADPH Production*," Nature 510:298-302). In intact mammals, fat synthesis is thought to be localized primarily to liver and adipose (Nguyen, P. et al. (2008) "*Liver Lipid Metabolism*," J. Anim. Physiol. Anim. Nutr. (Berl). 92:272-283). Significant malic enzyme activity was described in adipose tissue more than 50 years ago, and malic enzyme is generally accepted to contribute to meeting the high NADPH needs of adipocytes; however, prior quantitative analysis of its contributions suggest that it is small relative to the oxPPP (Flatt, J. P. et al. (1964) "*Studies on the Metabolism of Adipose Tissue:* XV. AN EVALUATION OF THE MAJOR PATHWAYS OF GLUCOSE CATABOLISM AS INFLUENCED BY INSULIN AND EPINEPHRINE." J. Biol. Chem. 239:675-685). When desired, the observed rate of total cellular fatty acid accumulation may be corrected for the fraction of fatty acid synthesized de novo, which can be determined by administering U-$^{23}$C-glucose and U-$^{23}$C-glutamine and measuring the extent of fatty acid labeling by mass spectrometry.

In one embodiment, PPP activity is measured by incubating cultured adipocytes (e.g., 3T3-L1 adipocytes) in the presence of 1-$^{14}$C-glucose versus 6-$^{14}$C-glucose and detecting the released $^{14}CO_2$. The oxPPP releases C1 of glucose as $CO_2$. The 6-$^{14}$C-glucose corrects for release of C1 by other pathways, because C1 and C6 are rendered identical by the triose phosphate isomerase step in glycolysis. After determining the oxPPP flux, the cells are provided with 1-$^2$H-glucose, which selectively labels NADPH in the first step (G6PDH) of the PPP.

The $^2$H-glucose labeling results can be used to quantitate the fractional contribution of the PPP to total cytosolic NADPH production. The inferred fractional contribution of the PPP to NADPH production can be used to deduce the total cytosolic NADPH production rate, which is equal to the absolute oxidative PPP flux divided by the fractional contribution of the PPP to NADPH production:

$$\text{Fraction}_{NADPH \text{ from oxPPP}} = \frac{2 \times NADP^2H / \text{Total } NADPH)}{(^2H\text{-}G6P / \text{Total}G6P)} \times C_{KIE} \quad \text{(Equation 4 (repeated))}$$

-continued $$\text{Fraction}_{NADPH \text{ from oxPPP}} = \quad \text{(Equation 15)}$$
$$2 \times \frac{NADP^2H}{NADPH_{total}} \times \frac{G6P_{total}}{^2H\text{-}G6P} \times$$
$$\text{Fraction}_{NADPH \text{ from all cytosolic sources}} \times C_{KIE}$$

In Equation 4, the determination of $CO_2$ from glucose C1 is based on the measured release rates of $^{14}C$—$CO_2$ corrected for the fractional radioactive labeling of glucose (and similarly for C6). These rates are multiplied by 2 to account for the stoichiometry of the oxPPP (2 NADPH per glucose). In Equation 15, the measured fractional $^2$H-labeling of NADPH is corrected for the $^2$H-labeling of glucose-6-phosphate and for the deuterium kinetic isotope effect ($C_{KIE}$) and multiplied by 2 to account for the 1-$^2$H-glucose tracer being labeled but that only one of the two hydrogens that are transferred to NADPH via the oxPPP.

The folate metabolic enzymes MTHFD and ALDH have NADPH-producing dehydrogenase activity. MTHFD is required for oxidizing methylene-THF into the key one-carbon donor formyl-tetrahydrofolate (formyl-THF), which is required for purine synthesis. In contrast, ALDH does not produce a useful one-carbon donor, but instead oxidizes formyl-THF into THF, $CO_2$, and NADPH (FIG. 3A). To evaluate total malic enzyme flux (sum of NADPH- and NADH-dependent malic enzyme), cells may be provided with U-$^{13}$C-glutamine, whose metabolism through the citric acid cycle and malic enzyme results in labeling of pyruvate.

$$\frac{\text{Fraction}_{malic \text{ } enzyme}}{\text{Fraction}_{glycolysis}} = \quad \text{(Equation 16)}$$
$$\frac{Pyr_{[M+2]}}{Pyr_{[M+0]}} \times \frac{\text{Malate}_{total}}{\text{Malate}_{[M+4]} + \text{Malate}_{[M+3]}}$$

This assay measures gross flux (the forward reaction flux from malate to pyruvate). Because malic enzyme is reversible, net flux (forward minus reverse flux) may be less.

Gross carbon flux through malic enzyme (ME) was quantified based on pyruvate labeling from U-$^{13}$C-glutamine. Since the observed fraction of M+1 and M+2 pyruvate are small (sum of both is less than 0.5%) relative to M+3 pyruvate (3%), the analysis is based solely on the observed M+3 pyruvate signal relative corrected for the fractional proportion of malate capable of making M+3 pyruvate. Forward flux from U-$^{13}$C-glutamine results in M+4 malate (1,2,3,4-$^{23}$C-malate) (21%). Reductive carboxylation of glutamine coupled to citrate lyase can produce M+3 malate in the form of 2,3,4-$^{23}$C-malate, which produces M+2, not M+3, pyruvate. Malate M+3 (total fractional abundance 8%) exists also as 1,2,3-$^{23}$C-malate, which produces M+3 pyruvate. Assuming rapid exchange between malate and fumarate (which is symmetric), the abundances of 1,2,3-$^{23}$C-malate and 2,3,4-$^{23}$C-malate will be equal; incomplete exchange will result in less 1,2,3-$^{23}$C-malate. This equation applies when malic enzyme flux is much less than glycolytic flux; otherwise, one would include a term to account for unlabeled pyruvate made via malic enzyme.

$$\frac{\text{Fraction}_{Malic \text{ } Enzyme}}{\text{Fraction}_{Glycolysis}} = \quad \text{(Equation 17)}$$

$$\frac{Pyr_{[M+3]}}{Pyr_{unlabelled}} \times \frac{Malate_{total}}{Malate_{[M+4]} + a*Malate_{[M+3]}}$$

where: $a = \frac{Malate_{[1,2,3-^{13}C]}}{Malate_{[1,2,3-^{13}C]} + Malate_{[2,3,4-^{13}C]}} \approx 0.5$ To more directly establish the contribution of malic enzyme to NADPH production, cells are provided with the $^2$H-labeled succinate analogue, 2,2,3,3-$^2$H-dimethyl-succinate, and deuterium labeling is followed through the C2 hydride of malate to NADPH and finally to newly synthesized fatty acid molecules (FIGS. 15A-15F). Although any suitable labeled molecule may be used to trace hydride flux from malate to NADPH and subsequently into fat, it is preferred to use 2,2,3,3-$^2$H-dimethyl-succinate for the above purpose.

NADPH labeling at its redox active hydride was analyzed by comparing the M+1 fraction of NADPH to NADP+. In the absence of 2,2,3,3-$^2$H-dimethyl succinate, the NADP+ and NADPH labeling patterns were identical; addition of tracer resulted in increased labeling of NADPH but not NADP+ selectively in differentiating (day 5) but not proliferating (day 0) 3T3-L1 cells, with 3.4%±0.3% of the total adipocyte NADPH labeled (FIG. 15C). Analysis of fatty acids (which was corrected for the fraction of newly synthesized fatty acids based on carbon labeling, which reflects specifically cytosolic NADPH, similarly revealed selective 2H-labeling in the differentiating adipocytes (FIG. 15D). Quantitative analysis of the mass isotope distribution of a set of abundant fatty acids revealed an average hydride 2H-labeling fraction of 2.87%±0.31%. Correction for the kinetic isotope effect in hydride transfer from NADPH to fat (approximately 1.1) yields an associated NADPH labeling fraction of 3.2%±0.5%, in excellent agreement with the directly measured whole cell NADPH labeling.

Converting the NADPH labeling fraction from 2,2,3,3-$^2$H-dimethyl-succinate into the fractional NADPH contribution of malic enzyme requires two important corrections: (i) fractional $^2$H-labeling of malate's C2 hydride and (ii) the malic enzyme deuterium kinetic isotope effect (approximately 1.5).

$$\text{Fraction}_{NADPH \text{ from Malic Enzyme}} = \frac{NADP^2H}{NADPH} \times \qquad \text{(Equation 18)}$$
$$\frac{Malate}{Malate_{C2-deuteron}} \times \text{Fraction}_{NADPH \text{ from all sources}} \times C_{KIE}$$

Forward flux from 2,2,3,3-$^2$H-succinate results in 2,3-$^2$H-malate, i.e., M+2 malate (FIG. 15B). The observed fraction of M+2 malate was, however, only 1.5%. The larger peak was M+1 malate (FIG. 15E). Reverse flux through malate dehydrogenase can produce M+1 malate labeled at the C3 hydride (3-$^2$H-malate). As fumarate is symmetric, fumarase will interconvert 3-$^2$H-malate and 2-$^2$H-malate (FIG. 15B). Because malic enzyme will produce NADP$^2$H selectively from malate labeled at the C2 hydride, the relative abundance of 2-$^2$H-malate versus 3-$^2$H-malate was determined. 3-$^2$H-malate (and also 2,3-$^2$H-malate) yields M+1 oxaloacetate and hence M+1 aspartate, whereas 2-$^2$H-malate yields unlabeled oxaloacetate and aspartate. Hence, subtracting the fraction of M+1 aspartate from that of M+1 plus M+2 malate gives the fraction of 2-$^2$H-malate (FIG. 15E), which was approximately 6.4%. Summing 2-$^2$H-malate and 2,3-$^2$H-malate, the fraction of malate that is capable of making NADP$^2$H was 7.9% (FIG. 15F).

$$\frac{Mal_{C2-deuteron}}{Mal} = \frac{[2-^2H]Mal}{Mal} + \frac{[2,3-^2H]Mal}{Mal} = \qquad \text{(Equation 19)}$$
$$\left(\frac{Mal_{[M+1]} + Mal_{[M+2]}}{Mal}\right) - \left(\frac{Asp_{[M+1]}}{Asp} - \frac{Mal_{[M+2]}}{Mal}\right)$$

Correction for the isotope effect is:

$$\frac{F_D}{F_H} = \frac{x}{(1-x)} * \frac{v_D}{v_H} \qquad \text{(Equation 20)}$$

Thus, while 2,2,3,3-$^2$H-dimethyl succinate labeled only approximately 3.2% of NADPH, after correction for the extent of malate labeling and the malic enzyme kinetic isotope effect, the fraction of NADPH generated via malic enzyme is approximately 60%. Thus, the deuterium tracer studies directly demonstrate that malic enzyme is the predominant NADPH source in 3T3-L1 adipocytes.

FIG. 16 shows the pyruvate-citrate cycle driven by ME1 to promote fatty acid synthesis.

H. Preferred Methods

1. Cell Lines and Culture Conditions

HEK293T and MDA-MB-468 cells may be purchased from ATCC. Immortalized baby mouse kidney epithelial cells (iBMK) with or without myr-AKT are obtainable from E. White (see, e.g., Degenhardt, K. et al. (2002) "*BAX And BAK Mediate P53-Independent Suppression Of Tumorigenesis,*" Cancer Cell 2:193-203; Mathew, R. (2008) "*Immortalized Mouse Epithelial Cell Models To Study The Role Of Apoptosis In Cancer,*" Methods Enzymol. 446:77-106). All cell lines are preferably grown in Dulbecco's Modified Eagle's Medium (DMEM) without pyruvate (CELLGRO), supplemented with 10% dialyzed fetal bovine serum (Invitrogen) in a 5% $CO_2$ incubator at 37° C. 3T3-L1 pre-adipocytes were grown in Dulbecco's modified Eagle's media (DMEM, Cellgro, 10-017) with 10% FBS (Gibco, heat-inactivated). Adipogenesis was induced in 3T3-L1 pre-adipocytes with a cocktail containing 5 μg/ml insulin, 0.5 mM isobutylmethylxanthine, 1 μM dexamethasone and 5 μM troglitazone (Sigma). After 2 days, new medium was added and cells were maintained in 5 μg/ml insulin. For all isotope labeling experiments, dialyzed serum was used.

Knockdown of enzymes is preferably accomplished by infection with lentivirus expressing the corresponding shRNA (Table 1) and puromycin selection.

TABLE 1

| Gene | shRNA | Sequence | | SEQ ID NO. |
|---|---|---|---|---|
| MTHFD1 | #1 | ccgggctgaa gagattggga tcaaactcga gtttgatccc aatctcttca gcttttttg | | 1 |
|  | #2 | ccgggccatt gatgctcgga tatttctcga gaaatatccg agcatcaatg gcttttttg | | 2 |
| MTHFD2 | #1 | ccgggcagtt gaagaaacat acaatctcga gattgtatgt ttcttcaact gcttttttg | | 3 |
|  | #2 | ccgggctggg tatatcactc cagttctcga gaactggagt gatataccca gcttttttg | | 4 |

TABLE 1-continued

| Gene | | shRNA Sequence | SEQ ID NO. |
|---|---|---|---|
| G6PD | #1 | ccggcaacag atacaagaac gtgaactcga gttcacgttc ttgtatctgt tgtttttg | 5 |
| | #2 | ccgggctgat gaagagagtg ggtttctcga gaaacccact ctcttcatca gctttttg | 6 |
| NNT | #1 | ccggccctat ggttaatcca acattctcga gaatgttgga ttaaccatag ggtttttg | 7 |
| ME1 | #1 | ccgggccttc aatgaacggc ctattctcga gaataggccg ttcattgaag gctttttg | 8 |
| | #2 | ccggccaaca atatagtttg gtgttctcga gaacaccaaa ctatattgtt ggtttttg | 9 |

To obtain the shRNA-expressing virus, pLKO-shRNA vectors (Sigma-Aldrich) are cotransfected with the third generation lentivirus packaging plasmids (pMDLg, pCMV-VSV-G and pRsv-Rev) into HEK293T cells using FuGENE 6 Transfection Reagent (Promega), fresh media added after 24 h, and viral supernatants collected at 48 h. Target cells are infected by viral supernatant (preferably diluted 1:1 with DMEM; 6 µg/ml polybrene), fresh DMEM is added after 24 h, and selection with 3 µg/ml puromycin initiated at 48 h and allowed to proceed for 2-3 days. Thereafter, cells are preferably maintained in DMEM with 1 µg/ml puromycin. For IDH1, IDH2 and ALDH1L2 knockdown, siRNA targeting IDH1 or IDH2 (Thermo Scientific, 40 nM) or ALDH1L2 (Santa Cruz, 30 nM) are transfected into H293T cells using LIPOFECTAMINE™ RNAiMAX (Invitrogen).

Knockdown of enzymes is preferably confirmed by immunoblotting using, for example, commercial antibodies: G6PD (Bethyl Laboratories), MTHFD1 and MTHFD2 (Abgent), IDH1 (Proteintech Group), IDH2 (Abcam) and ALDH1L2 (Santa Cruz) or quantitative RT-PCR probes (ME1 and NNT, Applied Biosystems) (FIGS. 14A-14G).

2. Measurement of Metabolite Concentrations and Labeling Patterns

Cells are preferably harvested at a consistent confluency, e.g., approximately 80% confluency. For metabolomic experiments, medium is preferably replaced on a regular schedule, e.g., every 2 days and additionally 2 h before metabolome harvesting and/or isotope tracer addition. Metabolism is quenched and metabolites extracted, e.g., by aspirating media and immediately adding −80° C. 80:20 methanol:water. Supernatants from two rounds of methanol:water extraction are then preferably combined, dried under $N_2$, resuspended in HPLC water, placed in a 4° C. autosampler, and analyzed, preferably within 6 h to avoid NADPH degradation.

One suitable LC-MS method involves reversed-phase ion-pairing chromatography coupled by negative mode electrospray ionization to a standalone orbitrap mass spectrometer (Thermo Scientific) scanning from m/z 85-1000 at 1 Hz at 100,000 resolution (Lu, W. et al. (2010) "*Metabolomic Analysis Via Reversed-Phase Ion-Pairing Liquid Chromatography Coupled To A Stand Alone Orbitrap Mass Spectrometer*," Analytical Chemistry 82:3212-3221; Munger, J. et al. (2008) "*Systems-Level Metabolic Flux Profiling Identifies Fatty Acid Synthesis As A Target For Antiviral Therapy*," Nat. Biotechnol. 26:1179-1186; Lemons, J. M. et al. (2010) "*Quiescent Fibroblasts Exhibit High Metabolic Activity*," PLoS Biol. 8:e1000514 (pages 1-10) with LC separation on a Synergy Hydro-RP column (100 mm×2 mm, 2.5 µm particle size, Phenomenex, Torrance, Calif.) using a gradient of solvent A (97:3 $H_2O$/MeOH with 10 mM tributylamine and 15 mM acetic acid), and solvent B (100% MeOH). A preferred gradient is: 0 min, 0% B; 2.5 min, 0% B; 5 min, 20% B; 7.5 min, 20% B; 13 min, 55% B; 15.5 min, 95% B; 18.5 min, 95% B; 19 min, 0% B; 25 min, 0% B. Injection volume was 10 µL, flow rate 200 µl/min, and column temperature 25° C. Data is preferably analyzed using the MAVEN software suite (Melamud, E. et al. (2010) "*Metabolomic Analysis And Visualization Engine For LC-MS Data*," Anal. Chem. 82:9818-9826). Other suitable methods are known in the art.

Data from $^{13}C$-labeling experiments are preferably adjusted for natural $^{13}C$ abundance and impurity of labeled substrate; those from $^2H$-labeling are preferably not adjusted (natural $^2H$ abundance is negligible) (Millard, P. et al. (2012) "*IsoCor: Correcting MS Data In Isotope Labeling Experiments*," Bioinformatics 28:1294-1296).

The absolute concentration of 6-phosphogluconate may be quantified by comparing the signal of $^{13}C$-labeled intracellular compound (from feeding U-$^{13}C$-glucose) to the signal of unlabeled internal standard.

3. Network Analysis of Potential NADPH-Producing Pathways

To assess the potential contribution of various metabolic pathways to NADPH production, feasible steady-state fluxes of a genome-scale human metabolic network model (Duarte, N. C. et al. (2007) "*Global Reconstruction Of The Human Metabolic Network Based On Genomic And Bibliomic Data*," Proc. Natl. Acad. Sci. (U.S.A.) 104:1777-1782) is analyzed. The glucose (98 nmol/(µL*h)), glutamine (40 nmol/(µL*h)), and oxygen uptake rates (21 nmol/(µL*h)), and lactate (143 nmol/(µL*h)), alanine (2 nmol/(µL*h)), pyruvate (15 nmol/(µL*h)), and formate (<0.25 nmole/(µL*h)) excretion rates are preferably set to experimental measured fluxes in the iBMK cell line (such values from exemplary experimental measurements of iBMK cells are written in parentheses above), as measured by a combination of electrochemistry (glucose, glutamine, lactate on YSI7200 instrument, YSI, Yellow Springs, Ohio), LC-MS (alanine, pyruvate with isotopic internal standards), fluorometry (oxygen on XF24 flux analyzer, Seahorse Bioscience, North Billerica, Mass.), and nuclear magnetic resonance (NMR) (formate by 1H 500 MHz, Bruker, 10 µM limit of detection). The uptake of amino acids from DMEM media can be measured directly or may be assumed to be bounded by a reasonable limit based on the cell type being studied, e.g., to not more than a third of that of glutamine, which is a loose constraint relative to experimental observations in iBMK cells and in NCI-60 cells (Jain, M. et al. (2012) "*Metabolite Profiling Identifies A Key Role For Glycine In Rapid Cancer Cell Proliferation*," Science 336:1040-1044). Biomass requirements are based on the experimentally determined growth rate of the cell line with protein, fatty acids and nucleotides accounting for 60%, 10% and 10% of the total cellular dry mass, respectively, based on experimental measurements, in iBMK cells. Steady-state intracellular fluxes that best fit these experimental constraints are then selected by solving the flux balance equations in MATLAB with the objective function formulated to minimize the sum of total fluxes (Folger, O. et al. (2011) "*Predicting Selective Drug Targets In Cancer Through Metabolic Networks*," Mol. Syst. Biol. 7:501 (pages 1-10).

4. ROS Measurement, Cell Proliferation and Cell Death Assay

Cells constantly generate reactive oxygen species (ROS) during aerobic metabolism. ROS measurement may be accomplished as described by Eruslanov, E. et al. (2010) ("*Identification Of ROS Using Oxidized DCFDA And Flow-Cytometry*," Methods Molec. Biol. 594:57-72). Briefly, cells are incubated with 5 μM CM-H2DCFDA (Invitrogen) for 30 min. Cells are trypsinized, and mean FL1 fluorescence is measured by flow cytometry. Cell proliferation is measured by trypsinizing cells and counting, for example, using a Beckman Multisizer 4 Coulter Counter. To measure cell death, cells are preferably stained with Trypan Blue. The stained and unstained cells are counted and cell death percentages are tabulated.

5. Measurement of $^{14}CO_2$ Release

Radioactive $CO_2$ released by cells from positionally-labeled substrates is preferably measured by trapping the $CO_2$ in filter paper saturated with 10 M KOH as described by Folger, O. et al. (2011) ("*Predicting Selective Drug Targets In Cancer Through Metabolic Networks*," Mol. Syst. Biol. 7:501 (pages 1-10). Cells are preferably grown in tissue culture flasks with DMEM medium with less than normal bicarbonate (0.74 g/L) and addition of HEPES buffer (6 g/L, pH 7.4). At the beginning of experiment, trace amount of desired 14C-labeled tracer is preferably added to the media. For each cell line, the amount added is preferably selected to be the minimum that gives a sufficient radioactive $CO_2$ signal to quantitate accurately (for example, approximately 1 μCi/ml).

All knockdown lines are treated identically to their corresponding parental line. Then the flask is sealed (e.g., with a rubber stopper with a central well (Kimble Chase) containing a piece of filter paper saturated with 10 M KOH solution). The flasks are preferably incubated at 37° C. for 24 h. $CO_2$ released by cells is absorbed by the base (i.e., KOH) in the central well. Metabolism is preferably stopped by injection of 1 mL 3 M acetic acid solution through the rubber stopper. The flasks are then incubated, e.g., at room temperature for 1 h, to ensure all the $CO_2$ dissolved in media has been released and absorbed into the central well. The filter paper and all the liquid in central well is then transferred to a scintillation vial containing 15 mL liquid scintillation cocktail (PerkinElmer Inc.). The central well is washed, e.g., with 100 μL water twice, and the water is added to the same scintillation vial. Radioactivity is then measured by liquid scintillation counting. Most preferably, in parallel, the same experiments are performed using U-$^{13}$C-labeled nutrient (in amounts that fully replace the unlabeled nutrient in DMEM) and the extent of labeling of the intracellular metabolite that is the substrate of the $CO_2$-releasing reaction is measured by LC-MS. Absolute $CO_2$ release rates from the nutrients of interest are calculated as follows:

$$\text{Rate}_{CO_2 \text{ from source}_i}[\text{nmole}/h/\mu l \text{ cells}] = \frac{\text{Rate}_{CO_2 \text{ from } ^{14}C-labeled-tracer_i}[\mu Ci/h/\mu l \text{ cells}]}{\text{overall media tracer}_i \text{ activity}[\mu Ci/nmole]} \times \frac{1}{\text{fraction}_{intracellular\ compound_i\ from\ media}}$$

(Equation 21)

6. Fractional Labeling of Cytosolic Formyl Groups from U-$^{13}$C-Serine

To measure the fractional labeling of cytosolic formyl groups from U-$^{13}$C-serine, cells are cultured with media containing U-$^{13}$C-serine, e.g., for 48 h, washed three times with cold PBS to remove extracellular serine, extracted, and the intracellular labeling pattern analyzed by LC-MS for ATP (representing purines; there is no labeling of ribose-phosphate based on LC-MS measurements), glycine, and serine. The purine ring has 5 carbons: 1 from $CO_2$, 2 from glycine, and 2 from formyl groups (from 10-formyl-THF). It is assumed that $CO_2$ labeling is negligible, which is realistic for cells grown in a 5% $CO_2$ incubator. Let $X_{ATP-i}$ and $X_{Gly-j}$ represent the experimentally observed fraction ATP and glycine with i and j labeled carbons. The cytosolic 10-formyl-THF labeling fraction, x, is then fit by least squares:

$$X_{ATP-0}=X_{Gly-0}*(1-x)^2$$

$$X_{ATP-1}=2*X_{Gly-0}*x(1-x)$$

$$X_{ATP-2}=X_{Gly-2}*(1-x)^2+X_{Gly-0}*x^2$$

$$X_{ATP-3}=2*X_{Gly-2}*x(1-x)$$

$$X_{ATP-4}=X_{Gly-2}*x^2 \quad \text{(Equation 22)}$$

7. Cytosolic NADPH Production from 10-Formyl-THF Pathway

Cytosolic NADPH production from 10-formyl-THF pathway is preferably quantified by tracking its end products: 10-formyl-THF consumed by purine synthesis and $CO_2$, since formate excretion into media is typically below the detection limit of NMR. All 10-formyl-THF consumed by purine synthesis is generated in cytosol and associated with the production of 1 NADPH. For each $CO_2$ released from serine C3, assuming reaction happens in cytosol, one molecule of NADPH is produced from 10-formyl-THF oxidation, and a second molecule of NADPH is produced via MTHFD1. Total cytosolic NADPH production via the 10-formyl-THF pathway is:

$$\text{Flux}_{NADPH(c)\ from\ THF-pathway} = 2 \times \text{Flux}_{purine\ synthesis} + 2 \times \text{Flux}_{CO_2\ from\ serine\ C3} \quad \text{(Equation 23)}$$

If complete oxidation of serine C3 instead happens in mitochondria, there is no cytosolic NADPH production associated with $CO_2$ released from serine C3 (i.e., no black bar in FIG. 3D). Instead, one molecule of mitochondrial NADPH is produced from 10-formyl-THF oxidation, and zero to one other molecules of mitochondrial NADPH is produced from 5,10-methylene-THF oxidation, depending on the enzyme used to catalyze the reaction and its cofactor specificity. In mitochondria, this reaction can be catalyzed by MTHFD2, which (at least in the presence of high phosphate in vitro) preferentially uses NAD+, or it can be catalyzed by MTHFD2L, which uses NADP+).

The complete oxidation of 3C of serine is found to be a meaningful source (approximately 5-10%) of NADPH in adipose cells.

8. Quantitation of NADPH Consumption by Reductive Biosynthesis

The general strategy for measuring consumption fluxes is preferably as follows: (i) identifying the biomass components produced in cells grown in culture media (such as DMEM) by NADPH-driven reductive biosynthesis (these are DNA, proline, and fatty acids); (ii) determining the biomass fraction of each component in each cell line; (iii) quantifying the cellular growth rate $R_{growth}=\ln(2)/t_{1/2}$; (iv) measuring the fractional contribution of different biosynthetic routes to each biomass component via experiments with $^{13}$C-labeled glucose and/or glutamine and LC-MS analysis; (v) computing the average number of NADPH per unit of biomass component, which equals the sum of the fractional contribution of each route multiplied by the number of NADPH consumed by that route; and (vi) determining NADPH consumption as follows:

Consumption flux=(product abundance/cell volume)×
$R_{growth}$×(average NADPH/product)     (Equation 24)

The data employed in such a determination can be acquired as follows:

DNA: Cellular DNA and RNA are extracted and separated with TRIzol reagent (Invitrogen), purified, and quantified by Nanodrop spectrophotometer;

Fatty acids: Total cellular lipid is extracted and saponified after addition of isotope-labeled internal standards for the C16:0, C16:1, C18:0, and C18:1. Samples are analyzed by negative ESI-LC-MS with LC separation on a C8 column. Concentrations of other fatty acids, for which isotope-labeled internal standard are not available, are measured by comparison to the palmitate internal standard. The calculated fatty acid concentrations are multiplied with a correction factor to account for incomplete lipid recovery in the first step of the sample preparation procedure. This correction factor is empirically determined to be 1.9 by experiments in which lipid standards were spiked into extraction solution. The extent of fatty acid synthesis and elongation (both of which consume NADPH) is determined by feeding cells U-$^{23}$C-glucose and U-$^{23}$C-glutamine for multiple doublings to achieve pseudo-steady-state labeling of their lipid pools. Fatty acid labeling patterns were measured and computationally simulated to quantify the fraction of production versus import for each individual fatty acid species. FIGS. 13A-13H show the associated data for C16:0, C16:1, C18:0, and C18:1, which together account for approximately 80% of total cellular fatty acids and greater than 90% of non-essential fatty acids (essential fatty acids are imported, not synthesized, and thus do not impact NADPH production). NADPH calculations include similar data for all measurable fatty acids.

Proline: Proline can be made from either arginine or glutamate. Proline synthesis from either substrate requires two high-energy electrons at the step catalyzed by pyrroline-5-carboxylate reductase, which may use NADH or NADPH (for simplicity, an equal contribution from each is assumed). Proline synthesis from glutamate consumes one additional NADPH (Lorans, G. et al. (1981) "*Proline Synthesis And Redox Regulation: Differential Functions Of Pyrroline-5-Carboxylate Reductase In Human Lymphoblastoid Cell Lines*," Biochem. Biophys. Res. Commun. 101:1018-1025). To quantify the fraction of proline synthesized from each substrate, cells are labeled with U-13C-glutamine to steady-state, which labels glutamate but not arginine. Labeling of intracellular proline and glutamate are measured:

$$X_{Glu} = \frac{\text{Fraction}_{proline\ 13C-labeled}}{\text{Fraction}_{glutamate\ 13C-labeled}}$$     (Equation 25)

$$\text{Flux}_{NADPH\ for\ proline} =$$     (Equation 26)
$$\frac{\text{growth rate} \times \text{protein content}}{\text{average formula weight per residue}} \times$$
$$\text{proline frequency} \times (1.5 X_{Glu} + 0.5(1 - G_{Glu}))$$

Proline synthesis enzymes are present in both the cytosol and mitochondria. For simplicity, exclusive cytosolic proline synthesis may be assumed (see, e.g., FIG. 4A-4B).

I. Diagnostic Utility

As discussed above, cells obtain NADPH both from reactions occurring in the cytosol, such as those of the oxPPP, and from reactions occurring in the mitochondria, such as those mediated by malic enzyme. One finding of the present invention is that a second pathway (the "10-formyl-THF pathway") can be a major contributor of NADPH in proliferating cells. In selected embodiments of the invention, the extent to which the amount (or relative proportion) of NADPH produced in cancer cells via the 10-formyl-THF pathway is greater than the amount (or relative proportion) of NADPH produced in non-cancerous cells is indicative of the presence and/or aggressiveness of such cancer.

Thus, the methods of the present invention permit one to diagnose cancer or metabolic disease (especially diabetes) and/or to assess the prognosis of a patient (i.e., a human or non-human mammal suspected or known to have cancer) having such disease by determining whether the contribution of its 10-formyl-THF pathway to cellular NADPH production is greater than that observed in normal, non-cancer cells.

The present invention thus provides a method for the diagnosis of cancer. Such method will most preferably be accomplished by administering a deuterium-labeled substrate of a biomolecule to actual or suspected tumor cells of a subject, and then determining the extent of deuterium labeling of the biomolecule by such cells. A determination that the rate of such deuterium labeling is elevated relative to that of healthy cells (preferably, of the same tissue type, and most preferably of the same tissue type and from the subject) is indicative of the presence of cancer. In one embodiment of such diagnostic method, the determination of the extent of deuterium labeling of the biomolecule is conducted in vivo (for example, using magnetic resonance imaging (MRI), etc.) or may be determined in vitro (for example, by first biopsying or otherwise obtaining a specimen of, the tumor or suspected tumor, and then subjecting the biomolecules produced by the cells of such biopsy or specimen to Liquid Chromatography-Mass Spectroscopy (LC-MS) analysis, Gas Chromatography-Mass Spectroscopy (GC-MS) analysis, etc.).

Although any suitable deuterium-labeled substrate may be employed, it is particularly preferred that such substrate be substrate of a redox-active hydride of NADPH, a substrate of a redox-active hydride of NADH, a substrate of a fatty acid molecule, or a substrate of a thymine moiety-containing biomolecule.

A particularly preferred deuterium-labeled substrate is 3,3-$^2$H-serine. Providing serine labeled at the hydrogens of carbon 3 (i.e., the methanolic carbon) results in formation of methylene-tetrahydrofolate (THF) with the one-carbon unit labeled at these hydrogens. Use of this methylene-THF to donate its 1 carbon unit to dUMP to form dTMP (which contains a thymine moiety) results in the thymine moiety-containing 2 deuteriums (i.e., mass is M+2). In contrast, if this methylene-THF first forms formyl-THF which then reforms methylene-THF, then one of the deuteriums is lost and the resulting thymine moiety contains one deuterium (i.e., mass is M+1). When thymine is form solely via the cytosolic folate pathway, either M+1 or M+2 may be formed, depending on the extent of reversible flux through the enzyme MTHFD1. In addition, methylene-THF can directly exchange with formaldehyde (non-enzymatically or enzymatically), thereby losing label. In contrast when thymine is formed via feeding of 1 carbon units formed by the mitochondrial folate pathway into the cytosol, only M+1 thymine is formed. Hence, the extent of thymine labeling, or thymine labeling relative to serine labeling, can be used to ascertain whether cytosolic methylene-THF units contain one-carbon units formed originally in the mitochondrion versus cytosol. This in turn informs the relative activities of the cytosolic and mitochondrial folate pathways. Specifically, significant formation of thymine M+2 indicates a preference for inhibition of the cytosolic pathway for treatment of a tumor, whereas lack of thymine M+2 indicates the suitability of the inhibition of the mitochondrial pathway.

Although the presence or rate of production of any deuterium-labeled biomolecule formed from such substrate may be determined in accordance with the present invention, it is particularly preferred that such deuterium-labeled biomolecule be a product of NADPH, product of a redox-active hydride of NADPH, a product of a redox-active hydride of NADH, a fatty acid molecule, or a thymine moiety-containing biomolecule (such as thymidine, thymidine triphosphate, thymidine diphosphate, thymidine monophosphate, DNA, etc.).

Alternatively, such assessment may be conducted by incubating tumor cells of a patient in the presence of glycine having one or more isotopically-labeled carbon atoms, determining the rate of isotopically-labeled $CO_2$ release, and comparing the rate of such $CO_2$ release to the rate of isotopically-labeled $CO_2$ release by healthy cells of that individual, or by cells of a healthy individual, receiving the isotopically-labeled glycine. Alternatively, such assessment may be made by determining the rate of isotopically-labeled $CO_2$ release after administration of serine having one or more isotopically-labeled carbon atoms. Any detectable isotope of carbon may be used for such labeling, however, $^{13}C$ (detectable via NMR) and $^{14}C$ (detectable via beta particle emission) are preferred. In selected embodiments, a determination that the cells of the patient exhibit a higher rate of isotopically-labeled $CO_2$ release than that exhibited by healthy cells is indicative of the presence of tumor cancer cells, or a determination that the tumor cells of the cancer patient exhibit a higher rate of isotopically-labeled $CO_2$ release than that exhibited by healthy cells is indicative of a poor cancer prognosis.

The present invention may also be used to diagnose cancer by measuring the amount (or relative proportion) of NADPH produced in cancer cells via oxPPP. In selected embodiments, a finding that such amount (or proportion) is lower or higher than the amount (or proportion) of NADPH produced in non-cancerous cells is indicative of the aggressiveness of such cancer.

The cancers that may be diagnosed in the above manners include a cancer such as: an adrenal gland tumor, an AIDS-associated cancer, an alveolar soft part sarcoma, an astrocytic tumor, a bladder cancer (e.g., a squamous cell carcinoma and a transitional cell carcinoma), a bone cancer (e.g., an adamantinoma, an aneurismal bone cyst, an osteochondroma, an osteosarcoma, etc.), a brain and spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder and bile duct cancer, a gestational trophoblastic disease cancer, a germ cell tumor, a head and neck cancer, an islet cell tumor, a Kaposi's sarcoma, a kidney cancer (e.g., a nephroblastoma, a papillary renal cell carcinoma, etc.), a leukemia, a lipoma/benign lipomatous tumor, a liposarcoma/malignant lipomatous tumor, a liver cancer (e.g., a hepatoblastoma, a hepatocellular carcinoma), a lymphoma, a lung cancer (e.g., a small cell carcinoma, a non-small cell carcinoma, an adenocarcinoma, a squamous cell carcinoma, a large cell carcinoma, etc.), a medulloblastoma, a melanoma, a meningioma, a multiple endocrine neoplasia, a multiple myeloma, a myelodysplastic syndrome cancer, a neuroblastoma, a neuroendocrine tumor, an ovarian cancer, a pancreatic cancer, a parathyroid tumor, a pediatric cancer, a peripheral nerve sheath tumor, a phaeochromocytoma, a pituitary tumor, a prostate cancer, a posterious uveal melanoma, a rare hematologic disorder cancer, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid cancer (e.g., a papillary thyroid carcinoma, a follicular thyroid carcinoma, a thyroid metastatic cancer, etc.) or a uterine cancer (e.g., a carcinoma of the cervix, an endometrial carcinoma, a leiomyoma, etc.).

Melanoma and multiple myeloma often have high expression of ALDH1L2 and accordingly are particularly appropriate targets for blocking of mitochondrial NADPH production by targeting folate metabolism.

J. Prognostic Utility

The present invention also provides a method for determining the suitability of a cancer therapy that comprises the administration of an anticancer agent for a particular cancer patient. This embodiment of the invention will most preferably be accomplished by administering a deuterium-labeled substrate of a biomolecule and the anticancer agent to tumor cells of the cancer patient, and then determining the extent of deuterium labeling of the biomolecule by such cells over time (i.e., upon 2 or more determinations made at different times) in the presence or absence of the anticancer agent. The present invention also provides a method for determining the suitability of a therapy for a metabolic disease (especially diabetes) that comprises the administration of a proposed therapeutic agent for a particular patient suffering from the metabolic disease. This embodiment of the invention will most preferably be accomplished by administering a deuterium-labeled substrate of a biomolecule to the patient, and then determining the extent of deuterium labeling of the biomolecule by such cells over time (i.e., upon 2 or more determinations made at different times) in the presence or absence of the proposed therapeutic agent. A finding for such cancer therapy or such therapy for a metabolic disease that the rate of such deuterium labeling is elevated relative to that of healthy cells, and is not substantially reduced over the course of the cancer therapy or the therapy for the metabolic disease is indicative of the non-suitability of the therapy for the particular patient. In selected embodiments, a finding that the administration of such anticancer agent or such proposed therapeutic agent for the metabolic disease has decreased the contribution of the 10-formyl-THF pathway of such cells to cellular NADPH production is indicative of the likely success of the proposed therapy. Significantly, such an assessment may be made prior to the initiation of any treatment, thus permitting doctors to rule out unsuitable therapies more quickly and at lower cost.

The deuterium-labeled substrate of a biomolecule and the anticancer agent may be concurrently administered, or may be administered at different times. In one embodiment, the deuterium-labeled substrate of a biomolecule and the anticancer agent are both administered to the patient. Alternatively, either of such reagents may be provided to the patient, after which a sample of tumor cells of the patient (e.g., a biopsy or other specimen), may be removed and the second of such reagents may be administered to the removed sample, and the determination of the extent of deuterium labeling of the biomolecule is determined in vitro. Alternatively, both the deuterium-labeled substrate of a biomolecule and the anticancer agent are administered to the removed sample, and the determination of the extent of deuterium labeling of the biomolecule is determined in vitro.

As in the above-described diagnostic methods, the determination of the extent of deuterium labeling of the biomolecule may be conducted in vivo (for example, using magnetic resonance imaging (MM), Raman spectroscopy, etc.) or may be determined in vitro (for example, by first obtaining a biopsy or other specimen of the tumor, or suspected tumor, and then subjecting the deuterium-labeled biomolecules produced by the cells of such biopsy or specimen to Liquid Chromatography-Mass Spectroscopy (LC-MS) analysis, Gas Chromatography-Mass Spectroscopy (GC-MS) analysis, magnetic resonance imaging (MRI), Raman spectroscopy, etc.).

Similarly to the above-described diagnostic methods, although any suitable deuterium-labeled substrate may be employed, it is particularly preferred that such substrate be a substrate of NADPH, a substrate of a redox-active hydride of NADPH, a substrate of a redox-active hydride of NADH, a substrate of a fatty acid molecule, or a substrate of a thymine moiety-containing biomolecule. A particularly preferred deuterium-labeled substrate is 3,3-$^2$H-serine.

Particularly when 3,3-$^2$H-serine is used as the deuterium-labeled substrate, such assessments may be made by measuring the production of M+2 deuterium-labeled thymine or a molecule that comprises an M+2 deuterium-labeled thymine moiety, or by measuring the production of $^2$H-labeled fatty acid molecules. The present invention is particularly amenable to assessing the suitability of a cancer therapy that comprises inhibiting cytosolic folate metabolism or inhibiting mitochondrial folate metabolism, especially by employing 3,3-$^2$H-serine as the deuterium-labeled substrate, and by measuring the production of M+2 deuterium-labeled thymine or a molecule that comprises an M+2 deuterium-labeled thymine moiety, or by measuring the production of $^2$H-labeled fatty acid molecules.

Alternatively, as in the above-described diagnostic methods, although the presence or rate of production of any deuterium-labeled biomolecule formed from such substrate may be determined in accordance with the present invention, it is particularly preferred that such deuterium-labeled biomolecule compromise one or more atoms derived from a redox-active hydride of NADPH, a redox-active hydride of NADH, or that it be a fatty acid molecule, or a thymine moiety-containing biomolecule (such as thymidine, thymidine triphosphate, thymidine diphosphate, thymidine monophosphate, DNA, etc.). For example, the invention provides a method for determining the suitability of a cancer therapy that comprises the administration of an anticancer agent for a particular cancer patient in which the anticancer agent and a deuterium-labeled substrate of NADPH are administered to tumor cells of the patient and the rate of passage of deuterium from the labeled substrate into NADPH by the tumor cells in the presence and in the absence of the anticancer agent is measured. A determination that the anticancer agent decreases the rate of passage of deuterium from the labeled substrate into NADPH by the tumor cells is predictive of the effectiveness of the anticancer agent.

Alternatively, such assessment may be conducted by incubating tumor cells of a patient in the presence of glycine having one or more isotopically-labeled carbon atoms and in the presence and absence of the anticancer agent, determining the rate of isotopically-labeled $CO_2$ release, and comparing the rate of such $CO_2$ release to the rate of isotopically-labeled $CO_2$ release by healthy cells of that individual, or by cells of a healthy individual, receiving the isotopically-labeled glycine. Alternatively, such assessment may be made by determining the rate of isotopically-labeled $CO_2$ release after administration of serine having one or more isotopically-labeled carbon atoms. Any detectable isotope of carbon may be used for such labeling, however, $^{13}$C (detectable via NMR) and $^{14}$C (detectable via beta particle emission) are preferred. In selected embodiments, a determination that the cells of the patient exhibit a higher rate of isotopically-labeled $CO_2$ release than that exhibited by healthy cells, and that such rate is not substantially reduced over the course of the cancer therapy is indicative of the non-suitability of the therapy for the particular patient.

The amount (or relative proportion) of NADPH produced by tumor cells via oxPPP may also be used to assess the suitability of a cancer therapy for a particular patient. In selected embodiments, a finding that such amount (or proportion) is lower than the amount (or proportion) of NADPH produced in non-cancerous cells and does not substantially decrease or increase over the course of the cancer therapy is indicative of the non-suitability of the therapy for the particular patient.

The cancers that may be evaluated in the above manners include a cancer such as: an adrenal gland tumor, an AIDS-associated cancer, an alveolar soft part sarcoma, an astrocytic tumor, a bladder cancer (e.g., a squamous cell carcinoma and a transitional cell carcinoma), a bone cancer (e.g., an adamantinoma, an aneurismal bone cyst, an osteochondroma, an osteosarcoma, etc.), a brain and spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder and bile duct cancer, a gestational trophoblastic disease cancer, a germ cell tumor, a head and neck cancer, an islet cell tumor, a Kaposi's sarcoma, a kidney cancer (e.g., a nephroblastoma, a papillary renal cell carcinoma, etc.), a leukemia, a lipoma/benign lipomatous tumor, a liposarcoma/malignant lipomatous tumor, a liver cancer (e.g., a hepatoblastoma, a hepatocellular carcinoma), a lymphoma, a lung cancer (e.g., a small cell carcinoma, a non-small cell carcinoma, an adenocarcinoma, a squamous cell carcinoma, a large cell carcinoma, etc.), a medulloblastoma, a melanoma, a meningioma, a multiple endocrine neoplasia, a multiple myeloma, a myelodysplastic syndrome cancer, a neuroblastoma, a neuroendocrine tumor, an ovarian cancer, a pancreatic cancer, a parathyroid tumor, a pediatric cancer, a peripheral nerve sheath tumor, a phaeochromocytoma, a pituitary tumor, a prostate cancer, a posterious uveal melanoma, a rare hematologic disorder cancer, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid cancer (e.g., a papillary thyroid carcinoma, a follicular thyroid carcinoma, a thyroid metastatic cancer, etc.) or a uterine cancer (e.g., a carcinoma of the cervix, an endometrial carcinoma, a leiomyoma, etc.).

Notably, by periodic assessments of the contribution of the 10-formyl-THF pathway to the cellular NADPH production of tumors or of biopsied tumor cells, the present invention permits one to assess whether a particular therapeutic regimen remains suitable for use in the treatment of cancer in a particular patient. Thus, for example, assessments indicating that the contribution of the 10-formyl-THF pathway to the cellular NADPH production of a tumor or of biopsied tumor cells decreased upon initiation of a therapeutic regimen and has remained depressed (relative to baseline) is indicative of the continued efficacy of the therapeutic regimen. Conversely, assessments indicating that the contribution of the 10-formyl-THF pathway to the cellular NADPH production of biopsied tumor cells decreased upon initiation of a therapeutic regimen and but is rising back to baseline is indicative of a failed efficacy of the therapeutic regimen. Most preferably, such assessment is conducted by incubating a sample of such biopsied tumor cells in the presence of a deuterium-labeled substrate of a biomolecule as described above, and then determine the amount, rate or extent of the production of the labeled biomolecule. Thus, the methods of the present invention provide a general "companion" diagnostic suitable for use with a wide variety of therapeutic regimens, such as:

A. Non-Specific Chemotherapeutic Agents, such as an alkylating agent (e.g., cyclophosphamide, mechlorethamine, chlorambucil, melphalan, nitrosoureas, temozolomide, etc.); an anthracycline (e.g., daunorubicin, doxorubicin, epirubicin, idarubicin, mitoxantrone, valrubicin, etc.); a cytoskeletal disruptor (e.g., paclitaxel, docetaxel, etc.); an epothilone (e.g., epothilone A, epothilone B, epothilone C, epothilone D, epothilone E, epothilone F, etc.); a histone deacetylase inhibitor (e.g., vorinostat, romidepsin, etc.); a nucleotide analogue or precursor analogue (e.g., azacitidine, azathioprine, capecitabine, cytarabine, doxifluridine, fluorouracil, gemcitabine, hydroxyurea, mercaptopurine, methotrexate, tioguanine (formerly thioguanine), etc.); a peptide antibiotic (e.g., bleomycin, actinomycin, etc.); a platinum-based antineoplastic agent (e.g., carboplatin, cisplatin, oxaliplatin, etc.); a retinoid (e.g., tretinoin, alitretinoin, bexarotene, etc.); a vinca alkaloid or derivative (e.g., vinblastine, vincristine, vindesine, vinorelbine, etc.);

B. Target Specific Chemotherapeutic Agents, such as a topoisomerase inhibitor (e.g., irinotecan, topotecan, etoposide, teniposide, tafluposide, etc.), a kinase inhibitor (e.g., bortezomib, erlotinib, gefitinib, imatinib, vemurafenib, vismodegib, etc.);

C. Immunotherapeutic Agents (e.g., antibodies or their epitope-binding fragments, diabodies (e.g., DARTs™, BiTEs™), etc.); or D. Radiotherapeutics (e.g., external beam radiation therapy, auger therapy, ionizing radiation therapy, particle therapy, brachytherapy, etc.).

Alternatively, such assessment may be conducted by incubating a sample of such biopsied tumor cells in the presence of carbon isotope-labeled glycine or serine and determining whether the administration of the potential therapeutic agent affects the rate of isotopically-labeled $CO_2$ release. In one embodiment, cells are transiently incubated in the absence of such agent, the rate of isotopically-labeled $CO_2$ release is measured and then the cells are further incubated in the presence of such agent with the rate of isotopically-labeled $CO_2$ release being measured again. Alternatively, two portions of the biopsied sample may be separately incubated, one in the absence of such agent and the second in the presence of such agent, and the observed rate of isotopically-labeled $CO_2$ release of such portions compared to determine the likely effect of the therapeutic agent. Any detectable isotope of carbon may be used for such labeling, however, $^{13}C$ (detectable via NMR) and $^{14}C$ (detectable via beta particle emission) are preferred.

K. Therapeutic Utility

Anti-folate anticancer agents act to inhibit the growth of cancer cells by inhibiting the enzymes of folate metabolism, thereby inhibiting the synthesis DNA and RNA. Such agents likewise act to inhibit the synthesis of formate or of molecules that comprises a formate moiety, as well as acting to inhibit the synthesis of glycine and of purines. Since such syntheses are required for the growth and survival of both normal cells and cancer cells, the use of anti-folate anticancer agents are associated with significant side effects, such as:

Common severe side effects include: azotemia, bacterial infection of blood or tissues affecting the whole body, bleeding of the stomach or intestines, canker sores, decreased blood platelet counts, decreased white blood cell counts, intestinal ulcers, inflammation of the gums and mouth, inflammation of the lining of the stomach and intestines, and sun-sensitive skin;

Common less severe side effects include: vertigo, nausea, loss of appetite, fatigue, and general infirmity;

Infrequent severe side effects include: anemia, arachnoid membrane inflammation; disease in the white matter area of the brain, hardening of the liver, hepatitis, interstitial pneumonitis, liver tissue death, and lung fibrosis;

Infrequent less severe side effects include: liver function abnormalities, acne, chills, diarrhea, fever, hair loss, itching, skin boils, skin rashes, and throat irritation;

Rare severe side effects include: Leigh's disease, acquired decrease of all cells in the blood, acute liver failure, avascular necrosis of bone, deficiency of granulocytes, elevation of protein levels in the urine, erythema multiforme, excess liver fibrous tissue, increased uric acid in blood, increased eosinophils concentration in blood, increased spinal fluid pressure, inflammation of blood vessels in the skin, inflammation of the alveoli of the lungs, kidney disease, kidney failure, bone marrow failure, pulmonary failure, *Pneumocystis jirovecii*-associated pneumonia, seizures, skin rash with sloughing, Stevens-Johnson Syndrome, and toxic epidermal necrolysis; and Rare less severe side effects include: bloody urine, inflammation of the bladder, and low sperm count.

The recognition that the 10-formyl-THF pathway contributes to cellular NADPH production additionally provides an improved method for using anti-folate anticancer agent to treat cancer. Such a method comprises administering to a cancer patient a pharmaceutical composition comprising:

(A) an anti-folate anticancer agent; and (B) one or more metabolic compounds selected from the group consisting of thymine, a molecule that comprises a thymine moiety, formate, a molecule that comprises a formate moiety, glycine or a pro-drug thereof, and a purine or a pro-drug thereof; and (C) a pharmaceutically acceptable excipient, carrier or diluent.

In accordance with the method, cells are at least partially rescued from the inhibition of thymine synthesis, formate synthesis, glycine synthesis and purine synthesis by the provision of one or more of such metabolic compounds. Accordingly, the effect of the anti-folate anticancer agent will be predominantly or completely focused on inhibiting cellular NADPH production via the 10-formyl-THF pathway. Since this pathway is particularly active in cancer cells (relative to non-cancer cells), the therapeutic index of the treatment (i.e., its selectivity against cancer cells) is enhanced. Thus, the pharmaceutical composition acts to inhibit NADPH production without adversely affecting the concentration of desired metabolic compound(s).

In a further embodiment, tumor cells are monitored for their ability to label fatty acid molecules from $^2$H-serine. Tumor cells that are defective in mitochondrial folate metabolism (for example, due to poor expression of one or more of the involved enzymes, or due to mutations that encode defective enzymes) are reliant on cytosolic folate metabolism. For example, the 8988T pancreatic cell line (Elsässer, H. P. et al. (1992) *"Establishment And Characterisation Of Two Cell Lines With Different Grade Of Differentiation Derived From One Primary Human Pancreatic Adenocarcinoma,"* Virchows Arch. B Cell. Pathol. Incl. Mol. Pathol. 61(5):295-306) exhibits such a defect.

In accordance with the principles of the present invention, tumor cells that are defective in mitochondrial folate metabolism may be recognized by the production of deuterated NADPH in the cytosol from $^2$H-serine, or by the consequent production of deuterated fatty acid molecules. One aspect of the present invention thus relates to diagnosing the presence of such tumor cells by detecting such deuterated compound(s) and treating such cancers with one or more agents that antagonize or block cytosolic folate metabolism. Preferred agents that antagonize or block cytosolic folate metabolism include inhibitors of the enzyme SHMT1, for example, the compound HK-16, whose structure Enantiomer-2 and Enantiomer-1 structures are shown below:

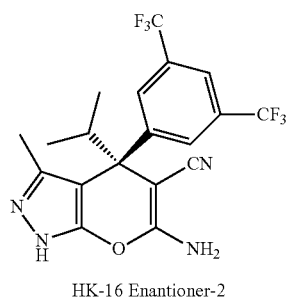

HK-16 Enantioner-2

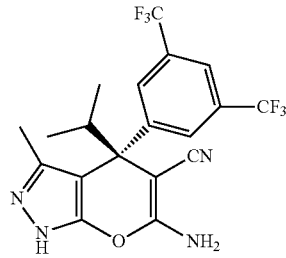

HK-16 Enantioner-1

HK-16 Enantiomer-2 is (R)-6-amino-4-(3,5-bis(trifluoromethyl)phenyl)-4-isopropyl-3-methyl-1,4-dihydropyrano[2,3-c]pyrazole-5-carbonitrile. HK-16 Enantiomer-1 is (S)-6-amino-4-(3,5-bis(trifluoromethyl)phenyl)-4-isopropyl-3-methyl-1,4-dihydropyrano[2,3-c]pyrazole-5-carbonitrile. HK-16 Enantiomer-2 is preferred. Additional SHMT1 inhibitors are disclosed in U.S. Patent Application Ser. No. 62/131,205, which application is herein incorporated by reference in its entirety, and which disclosure of SHMT1 inhibitors is specifically incorporated by reference herein.

Thus, the pharmaceutical composition is preferably provided in an amount sufficient to treat the cancer and the included metabolic compound(s) are preferably provided in an amount(s) sufficient to remediate the attenuation of the concentration of such metabolic compound(s) that would otherwise have been caused by the anti-folate anticancer agent. Preferably, the amount of each such included metabolic compound(s) will be independently determined and will be at least 0.25 µg/kg of the patient's body weight, at least 0.5 µg/kg of the patient's body weight, at least 1 µg/kg of the patient's body weight, at least 2 µg/kg of the patient's body weight, at least 3 µg/kg of the patient's body weight, at least 4 µg/kg of the patient's body weight, at least 5 µg/kg of the patient's body weight, at least 6 µg/kg of the patient's body weight, at least 7 µg/kg of the patient's body weight, at least 8 µg/kg of the patient's body weight, at least 9 µg/kg of the patient's body weight, at least 10 µg/kg of the patient's body weight, at least 25 µg/kg of the patient's body weight, at least 50 µg/kg of the patient's body weight, at least 100 µg/kg of the patient's body weight, at least 250 µg/kg of the patient's body weight, at least 500 µg/kg of the patient's body weight, at least 1 mg/kg of the patient's body weight, at least 5 mg/kg of the patient's body weight, at least 6 mg/kg of the patient's body weight, at least 7 mg/kg of the patient's body weight, at least 8 mg/kg of the patient's body weight, at least 9 mg/kg of the patient's body weight, at least 10 mg/kg of the patient's body weight, at least 20 mg/kg of the patient's body weight, at least 30 mg/kg of the patient's body weight, at least 50 mg/kg of the patient's body weight, at least 100 mg/kg of the patient's body weight, at least 200 mg/kg of the patient's body weight, at least 300 mg/kg of the patient's body weight, at least 500 mg/kg of the patient's body weight, at least 1 g/kg of the patient's body weight, or more than 1 g/kg, or more than 1 g/kg of the patient's body weight.

Alternatively, the included metabolic compound(s) may be provided in an amount(s) sufficient to attenuate an adverse side effect that would otherwise have been caused by the administered anti-folate anticancer agent. In a preferred embodiment, the pharmaceutical composition is preferably provided in an amount sufficient to achieve one, two, three, four, or more of the following effects:

(i) reduce or ameliorate the severity of: azotemia, bacterial infection, intestinal or stomach ulcers, inflammation of the gums and mouth, inflammation of the lining of the stomach and intestines, or sun-sensitive skin;

(ii) increase blood platelet counts;

(iii) increase white blood cell counts;

(iv) reduce or ameliorate the severity of: anemia, arachnoid membrane inflammation; disease in the white matter area of the brain, hardening of the liver, hepatitis, interstitial pneumonitis, liver tissue death, or lung fibrosis;

(v) reduce or ameliorate the severity of: Leigh's disease, an acute liver failure, an avascular necrosis of bone, a deficiency of granulocytes, an elevation of protein level in the urine, erythema multiforme, excess liver fibrous tissue, increased uric acid in blood, increased eosinophils concentration in blood, increased spinal fluid pressure, inflammation of blood vessels in the skin, inflammation of the alveoli of the lungs, kidney disease, kidney failure, bone marrow failure, pulmonary failure, *Pneumocystis jirovecii*-associated pneumonia, seizures, skin rash with sloughing, Stevens-Johnson Syndrome, or toxic epidermal necrolysis;

(vi) reduce or ameliorate the severity of: vertigo, nausea, loss of appetite, fatigue, or general infirmity; or (vii) enhance or improve the prophylactic or therapeutic effect(s) of another therapy.

Such attenuation will preferably attenuate at least 20%, more preferably at least 25%, more preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, and most preferably at least 95% of at least one adverse side effect that would otherwise have been caused by the administered anti-folate anticancer agent.

In accordance with such methods, the anti-folate anticancer agent and the one or more metabolic compounds may be administered simultaneously to the patient, or may be administered to the patient at differing times. For example, the first of such two compositions (i.e., either the anti-folate anticancer agent or the one or more metabolic compounds) can be administered at least 5 minutes prior to, at least 15 minutes prior to, at least 30 minutes prior to, at least 45 minutes prior to, at least 1 hour prior to, at least 2 hours prior to, at least 4 hour prior to, at least 6 hours prior to, at least 12 hours prior to, at least 24 hours prior to, at least 48 hours prior to, at least 96 hours prior to, at least 1 week prior to, at least 2 weeks prior to, at least 3 weeks prior to, at least 4 weeks prior to, at least 5 weeks prior to, at least 6 weeks prior to, at least 8 weeks prior to, or at least 12 weeks prior to the administration of the second of such compositions (i.e., either the one or more metabolic compounds or the anti-folate anticancer agent).

The administration of the pharmaceutical composition (i.e., the anti-folate anticancer agent, the one or more metabolic compounds, whether provided simultaneously or at different times) may be provided once, or the treatment may be repeated 2, 3, 4, 5, or more times in a course of treatment. Any temporal spacing between the administration of the anti-folate anticancer agent and the administration of the one or more metabolic compounds of a treatment may be maintained or altered in a subsequent treatment.

The anti-folate anticancer agent of the pharmaceutical composition may be any anti-folate anticancer agent, including in particular, any of those discussed above. Likewise, the cancers that may be treated in this manner include all of those discussed above.

L. Pharmaceutical Compositions

Generally, the ingredients of the above-described pharmaceutical composition are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be conveniently mixed prior to administration.

The above-described pharmaceutical composition compositions may be formulated for oral administration and presented as discrete dosage forms, such as, but are not limited to, tablets (e.g., chewable tablets), caplets, capsules, and liquids (e.g., flavored syrups). Such dosage forms may be prepared by methods of pharmacy well known to those skilled in the art. See generally, Remington: The Science and Practice of Pharmacy (2000) Twentieth Edition, Lippincott Williams & Wilkins: Philadelphia, Pa. (Gennaro, A.R. ed.). Excipients suitable for use in oral liquid or aerosol dosage forms include, but are not limited to, water, glycols, oils, alcohols, flavoring agents, preservatives, and coloring agents. Excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103.TM. and Starch 1500 LM.

A disintegrant may be used in the composition to provide tablets that disintegrate when exposed to an aqueous environment. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant. Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants may be used in the composition if desired. Suitable lubricants include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The compounds of the pharmaceutical compositions can be formulated to permit their controlled release (see, e.g., U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

The pharmaceutical composition of the present invention may be formulated for parenteral administration. Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Agents that increase the solubility of the compounds of the pharmaceutical compositions of the present invention can be incorporated into the parenteral dosage forms provided herein, if desired.

Transdermal, topical, and mucosal dosage forms of the pharmaceutical compositions of the present invention include, but are not limited to, ophthalmic solutions, sprays, aerosols, creams, lotions, ointments, gels, solutions, emulsions, suspensions, or other forms known to one of skill in the art. See generally, Remington: The Science and Practice of Pharmacy (2000) Twentieth Edition, Lippincott Williams & Wilkins: Philadelphia, Pa. (Gennaro, A. R. ed.). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See generally, Remington: The Science and Practice of Pharmacy (2000) Twentieth Edition, Lippincott Williams & Wilkins: Philadelphia, Pa. (Gennaro, A. R. ed.).

Depending on the specific tissue to be treated, additional components may be used prior to, in conjunction with, or subsequent to treatment with the pharmaceutical compositions of the present invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of the pharmaceutical compositions of the present invention. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of the pharmaceutical compositions of the present invention so as to improve delivery. In this regard, stearates can serve as a lipid vehicle for the formulation, as an emulsifying agent or surfactant, and as a delivery enhancing or penetration enhancing agent. Different salts, hydrates or solvates of the Compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

M. Use in Drug Discovery

The methods of the present invention also find utility in facilitating the discovery of new anticancer therapies. Thus, for example, the contribution of the 10-formyl-THF pathway to cellular NADPH production may be determined with respect to cancer cells (either primary or of an established cell line) in the absence or presence of one or more candidate therapeutic agents, to thereby assess whether any such candidate therapeutic agent decreases the contribution of the 10-formyl-THF pathway of such cells to cellular NADPH production. A finding of such a decrease is indicative that a candidate therapeutic agent possesses efficacy in the treatment of cancer. Such cancer may be any of those discussed above.

Most preferably, such assessment is conducted by incubating a sample of such cancer cells in the presence of isotopically-labeled glycine or serine and determining whether the administration of the candidate therapeutic agent affects the rate of isotopically-labeled $CO_2$ release. In one embodiment, cells are transiently incubated in the absence of any such agent, the rate of isotopically-labeled $CO_2$ release is measured and then the cells are further incubated in the presence of a candidate therapeutic agent with the rate of isotopically-labeled $CO_2$ release being measured again. Alternatively, portions of the cell sample may be separately incubated, one or more in the absence of any such agent and one or more in the presence of a candidate therapeutic agent, and the observed rate of isotopically-labeled $CO_2$ release of such portions compared to determine whether any of the candidate therapeutic agent have anticancer therapeutic potential. Any detectable isotope of carbon may be used for such labeling, however, $^{13}C$ (detectable via NMR) and $^{14}C$ (detectable via beta particle emission) are preferred. In other embodiments, the above approach is applied by using $^2H$-tracers as described in the preceding sections as the readout.

N. Kits

The present invention additionally includes diagnostic kits suitable for facilitating the above-described diagnostic methods. Such kits may comprise, for example, one or more containers having filter paper, 10 M KOH, and other reagents suitable for collecting evolved $CO_2$ for subsequent quantitative measurement.

EXAMPLES

Having now generally described the invention, the same will be more readily understood through reference to the following examples, which are provided by way of illustration and are not intended to be limiting of the present invention unless specified.

Example 1

Use of Deuterium Tracer to Directly Measure NADPH Redox-Active Hydrogen Labeling To probe the oxPPP, cells were shifted from unlabeled to 1-$^2$H-glucose or 3-$^2$H-glucose (FIG. 1A) and the resulting NADP+ and NADPH labeling was measured using liquid chromatography-mass spectrometry (Lu, W. et al. (2010) "*Metabolomic Analysis Via Reversed-Phase Ion-Pairing Liquid Chromatography Coupled To A Stand Alone Orbitrap Mass Spectrometer*," Analytical Chemistry 82:3212-3221).

Results of such measurements are shown in the mass spectrum provided in FIG. 1B and FIG. 5A). The M+1 and M+2 peaks in NADP+ are natural isotope abundance, primarily from $^{13}C$. The difference between NADP+ and NADPH reflects the redox-active hydrogen labeling. The labeling of NADPH's redox-active hydrogen is fast ($t_{1/2}$ approximately 5 min) (FIG. 1C; in the Figure, all fractional labeling data are corrected for natural isotope abundance as opposed to relative mass intensities). NADPH labeling was similar across four different transformed mammalian cell lines. Knockdown of the committed enzyme of the oxPPP, glucose-6-phosphate dehydrogenase, eliminated most of the labeling, confirming that the NADPH-deuterium labeling reflects oxPPP flux (FIG. 1D). Note that these $^2H$-labeling experiments directly measure the fraction of NADPH made by the oxPPP without relying on measurement of the absolute pathway flux. Using either 1-$^2H$- or 3-$^2H$-glucose, we find that oxPPP accounts for 30-50% of overall NADP+ reduction.

Example 2

Use of Deuterium Tracer to Directly Measure NADPH Production from Other Pathways To investigate whether $^2H$-labeling could be used to directly observe NADPH production by other pathways (FIG. 2A), cells were fed 2,3,3,4,4-$^2H$-glutamine and 2,3,3-$^2H$-aspartate. Downstream products of glutamine can potentially transfer $^2H$ to NADPH via glutamate dehydrogenase or malic enzyme, while downstream products of aspartate may do so via isocitrate dehydrogenase (FIGS. 8A-8F).

Malic enzyme can produce either NADH or NADPH. Thus, total malic enzyme flux puts an upper limit on the associated NADPH production. To probe overall malic enzyme activity, cells were incubated with U-$^{13}$C-glutamine for 48 h, which resulted in a majority of intracellular malate being uniformly labeled (4-$^{13}$C, denoting the labeling of all four of the malate carbon atoms, "$^{13}C4$"), with a small portion being 3-$^{13}$C (denoting the labeling of 3 of the 4 malate carbon atoms). For simplicity, it is assumed that 3-$^{13}$C-malate is an equal mix of 1,2,3-$^{13}$C-malate and 2,3,4-$^{13}$C-malate (collectively designated as "$^{13}C_3$" malate) due to its rapid inter-conversion with fumarate (which is symmetric). Malic enzyme produces $^{13}C_3$-pyruvate from both 1,2,3,4-$^{23}C$ malate and 1,2,3-$^{23}C$-malate, whereas glycolysis produces unlabeled pyruvate (FIGS. 8A-8H).

$$\text{Flux}_{NADPHME} \leq \frac{\text{Pyruvate}(^{13}C_3)}{\text{Total Pyruvate}} \times \frac{\text{Total Malate}}{\text{Malate}(^{13}C_4) + 0.5\text{Malate}(^{13}C_3)} \times \text{Flux}_{glycolysis} \quad \text{(Equation 27)}$$

Identical mass spectra was observed for NADP+ and NADPH after feeding the deuterium-labeled glutamine and aspartate (FIG. 2B-2C, FIGS. 8B and 8D), and thus could not directly assign a fractional contribution to these pathways. Given recent evidence that malic enzyme is particularly important in cancer (Jiang, P. et al. (2013) "*Reciprocal*

Regulation Of P53 And Malic Enzymes Modulates Metabolism And Senescence," Nature 493:689-693; Son, J. et al. (2013) "Glutamine Supports Pancreatic Cancer Growth Through A KRAS-Regulated Metabolic Pathway," Nature 496:101-105), an orthogonal approach based on feeding U-$^{13}$C-glutamine and measuring labeling of pyruvate, lactate and citrate was used to evaluate its activity (FIGS. 8G and 8H). While such carbon tracer studies cannot distinguish between NADH-dependent and NADPH-dependent malic enzyme, they put an upper bound on their collective activities, which ranged from 15% to 50% of cytosolic NADPH production depending on the cell line.

Example 3

Use of Deuterium Tracer to Directly Demonstrate the Presence of a Folate-Dependent Pathway for NADPH Production A genome-scale human metabolic model (Duarte, N. C. et al. (2007) "Global Reconstruction Of The Human Metabolic Network Based On Genomic And Bibliomic Data," Proc. Natl. Acad. Sci. (U.S.A.) 104:1777-1782) predicted that the main folate-dependent NADPH-producing pathway involved the transfer of a one-carbon unit from serine to THF, followed by oxidation of the resulting product (methylene-THF) by the enzyme MTHFD to form the purine precursor formyl-THF with concomitant NADPH production. To assess whether this pathway indeed contributed to NADPH production, mouse kidney cells (iBMK-parental cells) (Degenhardt, K. et al. (2002) "BAX And BAK Mediate P53-Independent Suppression Of Tumorigenesis," Cancer Cell 2:193-203) were fed cells 2,3,3-$^2$H-serine, and labeling of both NADP+ and NADPH was observed. NADP+ labeling would result from the incorporation of the serine-derived formyl-THF one-carbon unit into NADP+'s adenine ring.

Figure 2E:
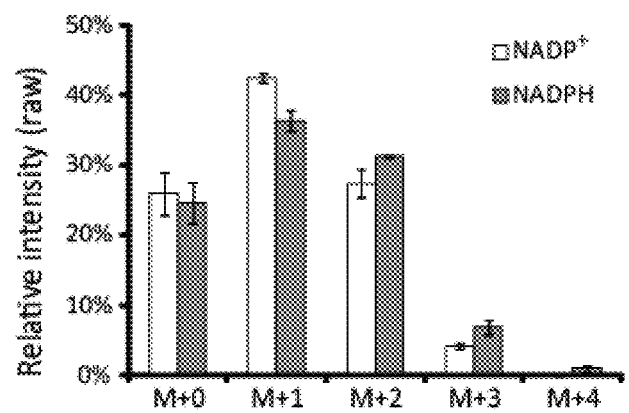

Relative to NADP+, the labeling pattern of NADPH was found to have been shifted towards more heavily labeled forms, indicating the specific labeling of NADPH's redox-active hydrogen (FIG. 2E, FIGS. 9C and 9D). Thus, the experimental results demonstrate that serine-driven folate metabolism contributed to NADP+ reduction.

Figure 2F:
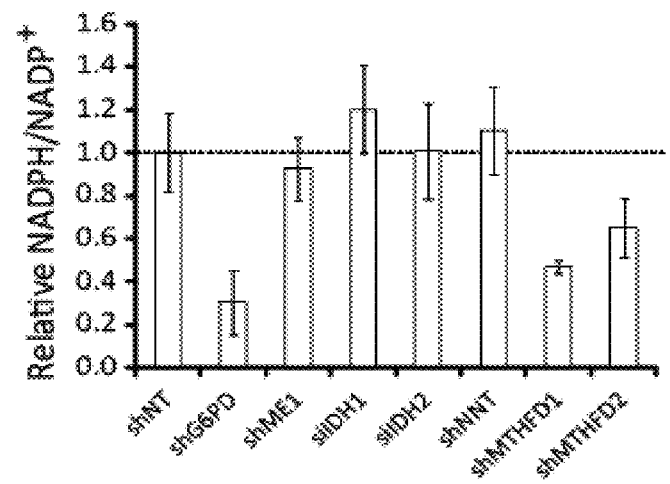

To assess the functional significance of different pathways to NADPH homeostasis, a variety of potential NADPH-producing enzymes were knocked down in HEK293T cells, and the cellular NADPH to NADP+ ratio was measured (FIG. 2F). While knockdown of malic enzyme 1 (ME1), cytosolic or mitochondrial NADP-dependent isocitrate dehydrogenase (IDH1 and IDH2), and transhydrogenase (NNT) did not significantly impact the NADPH to NADP+ ratio, knockdown of glucose-6-phosphate dehydrogenase or either isozyme of methylene-tetrahydrofolate dehydrogenase (MTHFD1, cytosolic, or MTHFD2, mitochondrial) substantially decreased it. These observations further support the primacy of the oxPPP and folate-dependent pathways in NADPH production.

The importance of both isozymes of methylene-tetrahydrofolate dehydrogenase suggests that cytosolic and mitochondrial folate metabolism (FIG. 3A) both contribute to NADPH homeostasis. The product of methylene-tetrahydrofolate dehydrogenase, 10-formyl-THF, is a required purine precursor, with each purine ring containing two formyl groups. Thus, the cytosolic 10-formyl-THF production rate must be at least twice the purine biosynthetic flux. The most direct path to cytosolic 10-formyl-THF is via MTHFD1 with concomitant NADPH production (FIG. 3A, striped lines). Alternatively, 10-formyl-THF could potentially be made from formate initially generated in the mitochondrion (FIG. 3A, dashed lines) (Tibbetts, A. S. et al. (2010) "Compartmentalization Of Mammalian Folate-Mediated One-Carbon Metabolism," Ann. Rev. Nutr. 30:57-81; Christensen, K. E. et al. (2008) "Mitochondrial Methylenetetrahydrofolate Dehydrogenase, Methenyltetrahydrofolate Cyclohydrolase, And Formyltetrahydrofolate Synthetases," Vitamins Hormones 79:393-410). To investigate these possibilities, U-$^{13}$C-glycine, which contributes selectively to mitochondrial one-carbon pools (FIG. 3A, gray lines) was fed to cells. Glycine is assimilated intact into purines, resulting in M+2 labeling of ATP; however, labeling of M+1, M+3, or M+4 ATP was not detected, indicating that mitochondrial glycine-derived one-carbon units do not contribute to purine biosynthesis (FIG. 3B). Consistent with this result, feeding of U-$^{13}$C-serine revealed that most one-carbon units assimilated into purines came from serine (FIGS. 10A and 10B), and knockdown of MTHFD1 nearly eliminated NADPH redox-active hydrogen labeling from 2,3,3-$^2$H-serine (FIG. 3C).

Assuming that all 10-formyl-THF production for purine synthesis is coupled to NADP+ reduction, the total NADPH production rate is approximately 2 nmol uL$^{-1}$ h$^{-1}$ (FIG. 3D) or approximately 25% of total cytosolic NADPH flux. To probe potential further oxidation of serine, cells were fed 3-$^{14}$C-serine and release of $^{14}$CO2 was observed, indicating that the THF pathway runs in excess of one-carbon demand so as to yield additional NADPH (FIG. 3D, FIGS. 11A-11H).

The consequences of elimination of serine from the medium was also investigated (FIGS. 12A-12E). As has been observed previously both in vitro (Locasale, J. W. et al. (2011) "Phosphoglycerate Dehydrogenase Diverts Glycolytic Flux And Contributes To Oncogenesis," Nature Genetics 43:869-874; Possemato, R. et al. (2011) "Functional Genomics Reveal That The Serine Synthesis Pathway Is Essential In Breast Cancer," Nature 476:346-350) and in tumor models (Maddocks, O. D. et al. (2013) "Serine Starvation Induces Stress And P53-Dependent Metabolic Remodelling In Cancer Cells," Nature 493:542-546), serine depletion impaired cell growth (FIG. 12B). Consistent with NADPH being an important downstream product of serine, serine removal decreased the NADPH to NADP+ ratio (FIG. 12C). Glycine is both a product of serine metabolism, and itself a potential source of one-carbon units via the mitochondrial glycine cleavage system, whose expression has been linked to oncogenic transformation (Zhang, W. C. et al. (2012) "Glycine Decarboxylase Activity Drives Non-Small Cell Lung Cancer Tumor-Initiating Cells And Tumorigenesis," Cell 148:259-272). Accordingly, the conversion of serine and glycine were tested by $^{13}$C labeling. It was found that flux through serine hydroxymethyltransferase is reversible, however, glycine-derived one-carbon unit cannot be used to synthesize serine in tested condition (FIGS. 12B-12E). Thus, increased glycine impairs methylene-THF production.

The above results establish that serine-driven, one-carbon metabolism plays a major role in NADPH homeostasis. Knockdown of MTHFD2 also alters the NADPH to NADP+ ratio, suggesting an additional role for mitochondrial one-carbon metabolism. Mitochondrial folate-dependent enzymes, especially MTHFD2, are overexpressed across human cancers (Nilsson, R. et al. (2014) "Metabolic Enzyme Expression Highlights A Key Role For MTHFD2 And The Mitochondrial Folate Pathway In Cancer," Nature Commun. 5:3128).

Figure 3E:
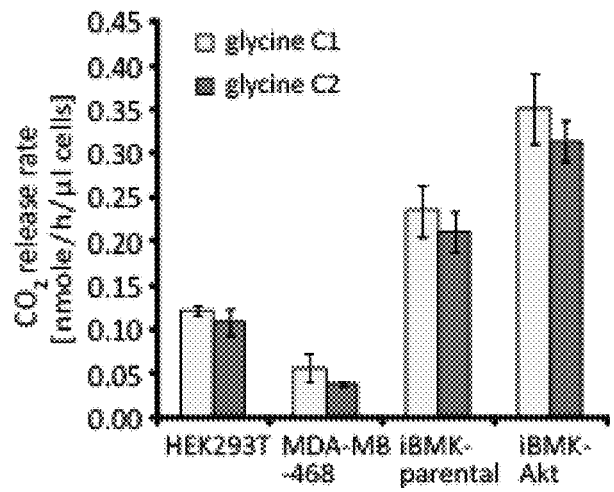

To probe specifically mitochondrial folate metabolism, cells were fed $^{14}C$-labeled glycine and the release of radioactive $CO_2$ was monitored. The glycine cleavage system releases the 1-C carbon of glycine as $CO_2$, while transferring glycine's 2-C carbon to THF (thereby forming methylene-THF). Notably, almost as much radioactive $CO_2$ was released from $2$-$^{14}C$-glycine as from $1$-$^{14}C$-glycine (FIG. 3E), indicating that a majority of mitochondrial methylene-THF was being fully oxidized to $CO_2$. Consistent with such complete oxidation, when cells were fed $^{13}C$-labeled glycine, the transfer of one-carbon units to the cytosol was not observed, based on the thymidine triphosphate (dTTP) or methionine labeling, with dTTP's one-carbon unit coming from serine (90-100%) and methionine coming from the medium (FIGS. 10A-10F). As expected based on the mitochondrial methylene-THF oxidation pathway, release of the 2-C carbon of glycine as $CO_2$ was decreased by knockdown of either MTHFD2 or ALDH1L2 (FIG. 11G). Such complete one-carbon unit oxidation may be beneficial for reducing the cellular glycine concentration. In addition, it produces mitochondrial NADPH. Thus, two functions of mitochondrial folate metabolism are glycine detoxification and NADPH production.

Example 4

NADPH and Antioxidant Defense

Figure 3F:
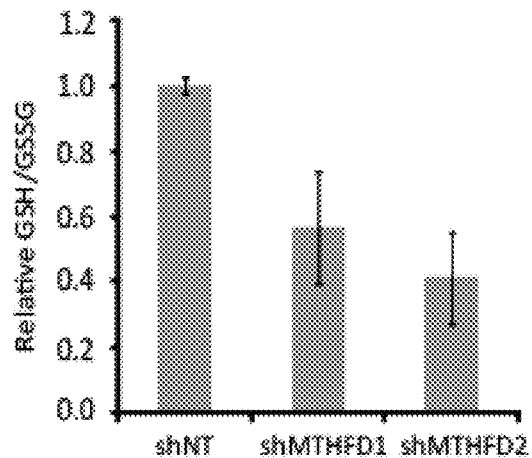
Figure 3G:
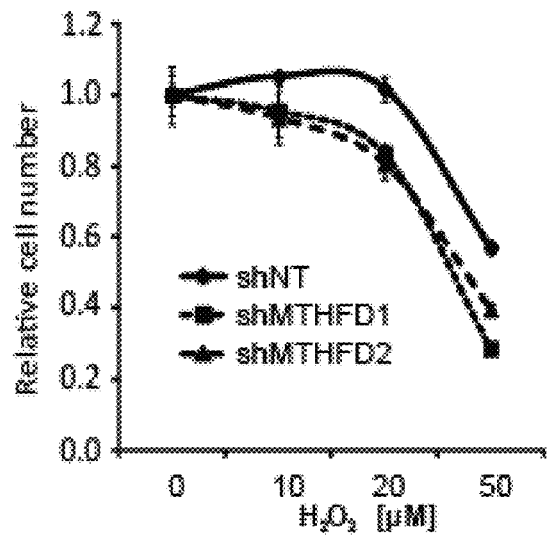
Figure 3H:
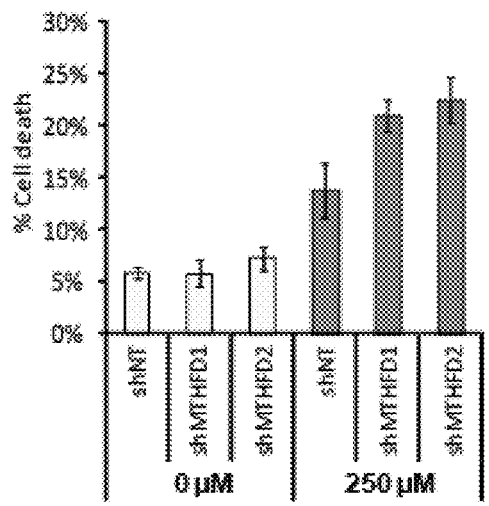
Figure 3I:
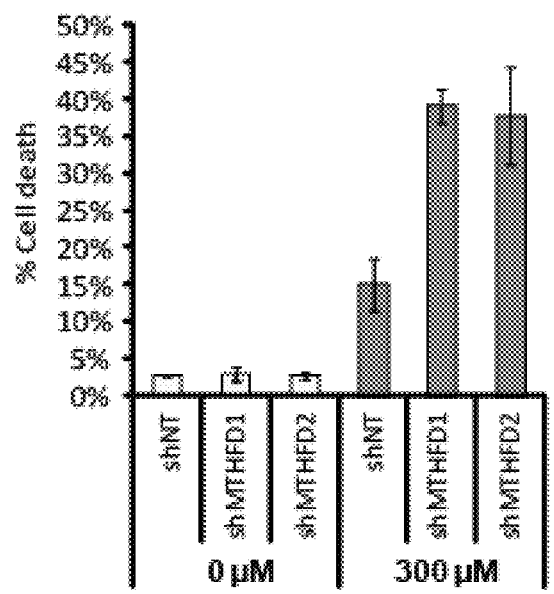
Figure 3J:
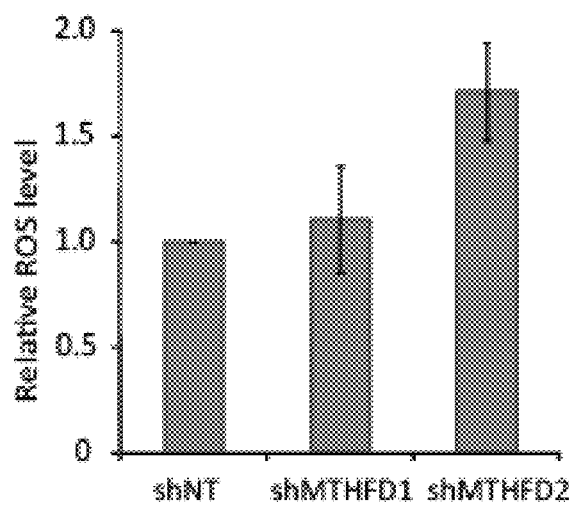

One important role of NADPH is antioxidant defense. Consistent with folate metabolism being a significant NADPH producer, antifolates have been found to induce oxidative stress (Ayromlou, H. et al. (2011) "*Oxidative Effect Of Methotrexate Administration In Spinal Cord Of Rabbits*" J. Pakistan Med. Assoc. 61:1096-1099). To more directly link folate-mediated NADPH production with cellular redox defenses, glutathione, reactive oxygen species, and hydrogen peroxide sensitivity of MTHFD1 and MTHFD2 knockdown cells were measured. Knockdown of either isozyme decreased the ratio of reduced to oxidized glutathione (FIG. 3F) and impaired resistance to oxidative stress induced by hydrogen peroxide (FIGS. 3G and 3H) or diamide (FIG. 3I). MTHFD2 knockdown specifically increased reactive oxygen species (FIG. 3J), and ALDH1L2 knockdown decreased the ratio of reduced to oxidized glutathione (FIG. 11H), demonstrating that the complete mitochondrial methylene-THF oxidation pathway is required for redox homeostasis.

To address the relative use of NADPH for biosynthesis versus redox defense total cytosolic NADPH production (as measured above) was compared to NADPH consumption for biosynthesis (FIG. 4A) based on the measured cellular content of DNA, amino acids, and lipids; their production routes (measured using a $^{13}C$ tracer); and cellular growth rate (FIGS. 13A-13G). The overall demand for NADPH for biosynthesis is >80% of total cytosolic NADPH production (FIG. 4B), with a majority of this NADPH consumed by fatty acid synthesis. Thus, in cells growing under aerobic conditions (and particularly transformed or cancerous cells) most cytosolic NADPH is devoted to biosynthesis, not redox defense.

To evaluate NADPH consumption for redox defense under overt redox stress, HEK293T cells were treated with hydrogen peroxide at a concentration that blocked growth without causing substantial cell death and the total cytosolic NADPH production rate was measured. The rate was found to be 5.5 nmol $\mu L^{-1}$ $h^{-1}$, about half the rate observed in freely growing cells (FIG. 13H). Thus, consistent with most cytosolic NADPH in growing cells being used for biosynthesis, growth-inhibiting oxidative stress decreased cytosolic NADPH production.

Example 5

Coupling of Nucleotide Synthesis with NADPH Production

The production of NADPH by the oxidative pentose phosphate pathway, which makes the nucleotide building block ribose, and by the 10-formyl-THF pathway, which contributes to purine synthesis, leads to an inherent coupling of nucleotide synthesis with NADPH production. These reactions together produce in growing cells roughly the amount of NADPH required for replication of cellular lipids (FIG. 4B). Interruption of this intrinsic coordination by feeding of purines can impair cell growth (Bradley, K. K. et al. (2001) "*Purine Nucleoside-Dependent Inhibition Of Cellular Proliferation In 1321N1 Human Astrocytoma Cells,*" J. Pharmacol. Exper. Therap. 299:748-752). In non-growing cells, or in other cases in which NADPH needs outstrip production coupled to nucleotide synthesis, it is likely that alternative pathways, e.g., malic enzyme and IDH, will be of greater importance than was observed.

The contribution of the 10-formyl-THF pathway to NADPH production is particularly interesting in light of the importance of metabolism of serine and glycine, the major carbon sources of this pathway, to cancer growth (Tedeschi, P. M. et al. (2013) "*Contribution Of Serine, Folate And Glycine Metabolism To The ATP, NADPH And Purine Requirements Of Cancer Cells,*" Cell Death Dis. 4:e877 (pages 1-12). Serine synthesis is promoted by the cancer-associated M2 isozyme of pyruvate kinase (PKM2) and by amplification of 3-phosphoglycerate dehydrogenase (Locasale, J. W. et al. (2011) "*Phosphoglycerate Dehydrogenase Diverts Glycolytic Flux And Contributes To Oncogenesis,*" Nature Genetics 43:869-874; Possemato, R. et al. (2011) "*Functional Genomics Reveal That The Serine Synthesis Pathway Is Essential In Breast Cancer,*" Nature 476:346-350). The present data indicates that serine serves dual roles in providing both one-carbon units and NADPH. In this respect, it is significant that PKM2, in addition to sensing serine (Ye, J. et al. (2012) "*Pyruvate Kinase M2 Promotes De Novo Serine Synthesis To Sustain mTORC1 Activity And Cell Proliferation,*" Proc. Natl. Acad. Sci. (U.S.A.) 109: 6904-6909; Chaneton, B. et al. (2012) "*Serine Is A Natural Ligand And Allosteric Activator Of Pyruvate Kinase M2,*" Nature 491:458-462), is inactivated by oxidative stress (Anastasiou, D. et al. (2011) "*Inhibition Of Pyruvate Kinase M2 By Reactive Oxygen Species Contributes To Cellular Antioxidant Responses,*" Science 334:1278-1283). Such inactivation should increase 3-phosphoglycerate and thus potentially serine-driven NADPH production.

In addition to synthesizing serine, rapidly growing cells avidly consume glycine (Jain, M. et al. (2012) "*Metabolite Profiling Identifies A Key Role For Glycine In Rapid Cancer Cell Proliferation,*" Science 336:1040-1044). Significantly, while only intact glycine (and not glycine-derived one-carbon units) is incorporated into purines, knockdown of the glycine cleavage system impairs cancer growth (Zhang, W. C. et al. (2012) "*Glycine Decarboxylase Activity Drives Non-Small Cell Lung Cancer Tumor-Initiating Cells And Tumorigenesis,*" Cell 148:259-272). One aspect of the present invention relates to the finding that most glycine-derived one-carbon units are fully oxidized, arguing against the glycine cleavage system's primary role, at least in the tested cell lines, being to release one-carbon units to the cytosol. Instead, its function may be simultaneous elimination of unwanted glycine and production of mitochondrial NADPH.

Understanding NADPH's production and consumption routes is essential to global understanding of metabolism. The approaches provided herein will enable evaluation of these routes in different cell types and environmental conditions. Analogous measurements for ATP, achieved first more than a half century ago (Warburg, O. (1956) "*On The Origin Of Cancer Cells*," Science 123:309-314), have formed the foundation for much of subsequent metabolism research. Given NADPH's comparable role in medically important processes including lipogenesis, oxidative stress, and tumor growth (Vander Heiden, M. G. et al. (2009) "*Understanding the Warburg Effect: The Metabolic Requirements Of Cell Proliferation*," Science 324:1029-1033), quantitative analysis of its metabolism is of similar importance and provides a means for diagnosing and evaluating cancer and other diseases.

Example 6

Use of 4-$^2$H-Glucose and 2,2,3,3-$^2$H-Dimethyl-Succinate as Tracers for Malic Enzyme Quantitative Analysis of NADPH Consumption in 3T3-L1 Cells The most NADPH-demanding biosynthetic activity in mammals is fat synthesis, which consumes a majority of cytosolic NADPH in typical transformed cells in culture (Fan, J. et al. (2014) "*Quantitative Flux Analysis Reveals Folate-Dependent NADPH Production*," Nature 510:298-302). In intact mammals, fat synthesis is thought to be localized primarily to liver and adipose (Nguyen, P. et al. (2008) "*Liver Lipid Metabolism*," J. Anim. Physiol. Anim. Nutr. (Berl) 92:272-283). Significant malic enzyme activity was described in adipose tissue more than 50 years ago (Young, J. W. et al. (1964) "*Metabolic Control Of Enzymes Involved In Lipogenesis And Gluconeogenesis*," Biochem. 3(11):1687-1692; Wise, E. M. et al. (1964) "*Malic Enzyme And Lipogenesis*," Proc. Natl. Acad. Sci. (U.S.A.) 52:1255-1263). During adipocyte differentiation, there is coordinate up-regulation of ATP citrate lyase and cytosolic malic enzyme (ME1), which together with cytosolic malate dehydrogenase, and at the expense of 1 ATP, can convert citrate and NADH into acetyl-CoA, NADPH, and pyruvate (Bagchi, S. et al. (1987) "*Structure and Expression of Murine Malic Enzyme mRNA*," J. Biol. Chem. 262(4):1558-1565). Acetyl CoA and NADPH are the two key substrates for fat synthesis, while the resulting pyruvate can be used to make more citrate. Thus, it is efficient to use malic enzyme to make NADPH in adipose tissue. The quantitative contribution of different NADPH-producing enzymes in adipose, however, has been previously ill-defined. In one of the only quantitative analyses, it was estimated that the contribution of oxPPP to NADPH synthesis in adipose tissue was approximately 60%, with the remainder coming from other pathways (contribution for the PPP and the remainder from other pathways (Flatt, J. P. et al. (1964) "*Studies on the Metabolism of Adipose Tissue: XV An Evaluation Of The Major Pathways Of Glucose Catabolism As Influenced By Insulin And Epinephrine On The Metabolism of Adipose*," J. Biol. Chem. 239:675-685).

In order to identify the enzymes responsible for NADPH production in adipose tissue, NADPH biosynthetic consumption fluxes were investigated in proliferating and differentiating 3T3-L1 preadipocytes cells. Such cells can be grown in standard tissue culture media and can be induced to differentiate into adipocytes by the addition of a hormone cocktail (Green, H. et al. (1974) "*An Established Pre-Adipose Cell Line and Its Differentiation In Culture*," Cell 3:127-133; Rosen, E. D. et al. (2006) "*Adipocyte Differentiation From The Inside Out*," Nat. Rev. Mol. Cell Biol. 7:885-896). Since the fastest lipid accumulation was found to occur between days 4 and 7, the investigation focused on proliferating and differentiating 3T3-L1 preadipocytes cells at day 5.

NADPH is used to drive the synthesis of deoxyribonucleotides, proline, and fatty acids. To determine the amount of NADPH consumed by deoxyribonucleotide synthesis, the rate of change in cell number was measured and cells were presumed to contain a constant amount of DNA, with 1.25 NADPH per employed DNA base (2 for thymidine and 1 for the other bases). To determine the amount of NADPH consumed by proline synthesis, the rate of protein accumulation was measured and was corrected for the average frequency of proline, with 1.5 NADPH being consumed per proline residue (Fan, J. et al. (2014) "*Quantitative Flux Analysis Reveals Folate-Dependent NADPH Production*," Nature 510:298-302). The NADPH consumption by DNA and proline synthesis was, as expected, significantly greater in proliferating cells relative to differentiating cells. To determine the amount of NADPH consumed by lipid synthesis, the rate of total cellular fatty acid accumulation for the fraction of fatty acid synthesized de novo was measured, as determined by feeding U-$^{13}$C-Glucose and U-$^{13}$C-Glutamine and measuring the extent of fatty acid labeling by mass spectrometry.

In the proliferating 3T3-L1 cells, fatty acids were assimilated to support growth, but $^{13}$C-labeling from glucose and glutamine was minimal, indicating fatty acid acquisition primarily by uptake from media. In contrast, upon differentiation, fatty acid content per cell increased, and was driven by de novo synthesis. In the proliferating and differentiating cells, the incorporation rate of two-carbon units into fatty acids was 4 and 30 nmol per day per µl of cell volume, respectively, with 2 NADPH required per two-carbon unit. Notably, the fat synthesis rate of the differentiating adipocytes was similar to that observed previously in transformed and cancer cells (Fan, J. et al. (2014) "*Quantitative Flux Analysis Reveals Folate Dependent NADPH Production*," Nature 510:298-302). Thus, total biosynthetic NADPH consumption in proliferating cells is relatively low and is devoted substantially to deoxyribonucleotide synthesis, whereas in differentiating adipocytes it is similar to in transformed proliferating cells, but devoted almost solely to fat synthesis (FIG. 17).

OxPPP Activity and Total NADPH Generation

Two complimentary methods were used to measure oxPPP activity in the proliferating and differentiating 3T3-L1 cells. First, cells were cultured in the presence of 1-$^{14}$C-Glucose versus 6-$^{14}$C-Glucose and the release of $^{14}CO_2$ was detected. The oxPPP releases C1 of glucose as $CO_2$. The 6-$^{14}$C-Glucose corrects for release of C1 by other pathways, because C1 and C6 are rendered identical by the triose phosphate isomerase step in glycolysis. An oxPPP flux of 6 and 5 nmol per day per µl of cell volume was observed in the proliferating and differentiating cells respectively; these rates are substantially lower than those previously reported in transformed growing cells (Fan, J. et al. (2014) "*Quantitative Flux Analysis Reveals Folate-Dependent NADPH Production*," Nature 510:298-3025). Next, cells were fed 1-$^2$H-Glucose, which selectively labels NADPH in the first step (G6PDH) of the oxPPP, and can therefore be used to determine the fraction of NADPH made by the oxPPP. In the proliferating cells, M+1 NADPH exceeded M+1 NADP+ by ~16% (FIG. 18). Similar NADPH labeling has also been observed in several transformed growing cell lines (Fan, J. et al. (2014) "*Quantitative Flux Analysis Reveals Folate-Dependent NADPH Production,*" Nature 510:298-302; Lewis, C. et al. (2014) "*Tracing Compartmentalized NADPH Metabolism in the Cytosol and Mitochondria of Mammalian Cells,*" Mol. Cell 55:253-263). In contrast, in the differentiating adipocytes, there was much less NADPH labeling from 1-$^2$H-Glucose. Thus, in contrast to growing cells, differentiating 3T3-L1 cells obtain a substantially lower fraction of their NADPH from the oxPPP.

The $^2$H-glucose labelling results can be used to quantitate the fractional contribution of the oxPPP to total cytosolic NADPH production. The inferred fractional contribution of the oxPPP to NADPH production can be used to deduce the total cytosolic NADPH production rate, which is equal to the absolute oxidative oxPPP flux divided by the fractional contribution of the PPP to NADPH production (Equation 10, Equation 15) (Fan, J. et al. (2014) "*Quantitative Flux Analysis Reveals Folate-Dependent NADPH Production,*" Nature 510:298-302; Lewis, C. et al. (2014) "*Tracing Compartmentalized NADPH Metabolism in the Cytosol and Mitochondria of Mammalian Cells,*" Mol. Cell 55:253-263).

The fraction $CO_2$ from glucose C1 is based on the measured release rates of $^{14}C$—$CO_2$ corrected for the fractional radioactive labeling of glucose (and similarly for C6) and multiplied by two to account for the stoichiometry of the oxPPP (2 NADPH per glucose). The measured fractional $^2$H-labeling of NADPH is corrected for the $^2$H-labeling of glucose-6-phosphate and for the deuterium kinetic isotope effect ($C_{KIE}$) and multiplied by two to account for the 1-$^2$H-glucose tracer being labeled at only one of the two hydrogens that are transferred to NADPH via the oxPPP. Combining Equation 10 with Equation 15, the measured absolute oxPPP NADPH production (12 and 10 nmol per day per µl cell volume) by the fractional contribution of the oxPPP (46% and 16%) gave a total cytosolic NADPH production flux of approximately 26 and 62 nmol per day per µl cell volume, in the proliferating and differentiating cells respectively. This total NADPH production flux was nearly identical to the independently measured biosynthetic NADPH consumption flux (FIG. 19). Thus, most NADPH both in proliferating and in differentiating cultured cells is consumed for biosynthesis, with fat synthesis dominant in the differentiating cells.

NADPH Contribution to Folate Metabolism

The folate metabolic enzymes MTHFD and ALDH have NADPH-producing dehydrogenase activity. MTHFD is required for oxidizing methylene-THF into the key one-carbon donor formyl-tetrahydrofolate (formyl-THF). In contrast, ALDH does not produce a useful one-carbon donor, but instead oxidizes formyl-THF into THF, $CO_2$, and NADPH (FIG. 20).

Cytosolic formyl-THF, which is required by proliferating cells for purine synthesis, can be produced from methylene-THF by the cytosolic methylene-THF dehydrogenase MTHFD1 with concomitant cytosolic NADPH production. Alternatively, it can be made from formate exported by mitochondria, in which case methylene-THF oxidation occurs in the mitochondria with associated production by MTHFD2 of mitochondrial NADH and (to a lesser extent) NADPH (Yang, X. M., et al. (1993) "*NAD-Dependent Methylenetetrahydrofolate Dehydrogenase-Methenyltetrahydrofolate Cyclohydrolase Is The Mammalian Homolog Of The Mitochondrial Enzyme Encoded By The Yeast MIS1 Gene*" Biochemistry 32(41):1118-1123; Tibbetts, A. S. et al. (2010) "*Compartmentalization Of Mammalian Folate-Mediated One-Carbon Metabolism,*" Annu. Rev. Nutr. 30:57-81).

To determine the location of 1-carbon unit synthesis in proliferating 3T3-L1 cells, such cells were fed 2,3,3-$^2$H-serine and production of $^2$H-labeled thymidine triphosphate (TTP) was measured. The cytosolic pathway produces doubly labeled TTP, whereas one deuterium is lost in the mitochondrial pathway resulting in single TTP labeling. Only M+1 TTP was observed, indicating minimal cytosolic MTHFD1 flux in the direction of NADPH production. Attention was therefore focused on the complete oxidation of one-carbon units by the combined action of MTHFD and ALDH, which can be traced based on release of $CO_2$ from 3-$^{14}$C-serine and 2-$^{14}$C-Glycine. A substantial release of serine C3 as $CO_2$ was observed, indicating that the complete one carbon oxidation pathway is actively producing NADPH (FIG. 21). The absolute magnitude, however, was smaller than the oxPPP flux. Consistent with the methylene-THF oxidation pathway resulting in a modest contribution to total NADPH production, feeding of 2,3,3-$^2$H-serine, the main pathway substrate, resulted in approximately 3% labeling of NADPH at its redox active hydride. Thus, in differentiating 3T3-L1 adipocytes, folate metabolism contributes modestly to NADPH production.

Tracing Carbon Flux Through Malic Enzyme with U-$^{13}$C-Glutamine

The above analysis implies that a majority of NADPH in differentiating adipocytes comes from source(s) other than the oxPPP and folate metabolism. Accordingly, the possibility contribution of malic enzyme was considered. In order to evaluate total malic enzyme flux, 3T3-L1 adipocytes were fed U-$^{13}$C-Glutamine, whose metabolism through the citric acid cycle and malic enzyme results in labeling of pyruvate (FIG. 20). Assuming that pyruvate and malate are labeled similarly in both mitochondria and cytosol, Equation 17 describes the relative contributions of malic enzyme to glycolysis to the gross flux from malate to pyruvate.

This assay measures gross flux from malate to pyruvate, which will exceed the net malic enzyme flux when alternative pathways between malate and pyruvate are active (e.g., gluconeogenesis, reverse pyruvate carboxylase, or reverse malic enzyme) (Wise, E. M. et al. (1964) "*Malic Enzyme And Lipogenesis,*" Proc. Natl. Acad. Sci. (U.S.A.) 52:1255-1263; Ochoa, S. et al. (1948) "*Biosynthesis Of Dicarboxylic Acids By Carbon Dioxide Fixation: I. Isolation And Properties Of An Enzyme From Pigeon Liver Catalyzing The Reversible Oxidative Decarboxylation Of L-Malic Acid,*" J. Biol. Chem. 174:979-1000; Jitrapakdee, S. et al. (2008) "*Structure, Mechanism and Regulation of Pyruvate Carboxylase,*" Biochem J. 413:369-387; Rutter, W. J. et al. (1958) "*Purification and Properties of Pigeon Liver Malic Enzyme,*" J. Biol. Chem. 233:374-382). It also does not account for pyruvate and malate compartmentation or identify whether malic enzyme is making NADH or NADPH.

Similar to most transformed cell lines, proliferating 3T3-L1 cells showed only trace pyruvate labeling from glutamine (DeBerardinis, R. J. et al. (2007) "*Beyond Aerobic Glycolysis: Transformed Cells Can Engage In Glutamine Metabolism That Exceeds The Requirement For Protein And Nucleotide Synthesis,*" Proc. Natl. Acad. Sci. (U.S.A.) 104: 19345-19350). Upon differentiation, however, extensive labeling was observed, with flux from malate to pyruvate flux accounting for ~15% of the differentiating adipocyte pyruvate pool. Due to the large magnitude of glycolytic flux (glucose uptake rate of 1600 nmol per day per µl cell volume), total gross flux from malate to pyruvate on day 5 is 600 nmol per day per µl cell volume, approximately 10-times the measured total NADPH consumption and production rates. Glucose uptake (and lactate excretion) were measured using commercial enzyme assay kits (e.g., Abcam ab65333 and Abcam ab65331), and are 1.62 and 2.58 µmol per day per µL cell volume, respectively; glutamine and dimethyl succinate uptake and glutamate, alanine, proline and asparagine secretion were measured by LC-MS to be 0.32, 0.08, 0.15, 0.13, 0.022 and 0.02 µmol per day per µL cell volume, respectively; and oxygen consumption was measured by a Seahorse XF Extracellular Flux Analyzer to be 1.19 µmol per day per µL cell volume.

To evaluate whether the gluconeogenic flux involving the combined action of malate dehydrogenase, phosphoenolpyruvate carboxykinase (PEPCK), and pyruvate kinase contributes to the observed pyruvate labeling, the labeling of phosphoenolpyruvate (PEP), the direct product of PEPCK, by [U-$^{13}$C]glutamine was monitored. Only trace labeling of PEP was observed (and similarly for 3-phosphoglycerate, which is linked to PEP by the reversible enzyme enolase and is more easily measured due to its higher abundance), thereby ruling out a major contribution of the gluconeogenic pathway.

The possibility that quantitative metabolic flux analysis (MFA) of $^{13}$C-labeling data for the full set of measurable central carbon metabolites would be sufficient to determine net malic enzyme flux and its compartmentation was investigated. Specifically, a carbon- and redox-balanced flux model of central metabolism was developed and was searched computationally for fluxes that fit experimental data for nutrient uptake, waste excretion, and metabolite $^{13}$C-labeling in cells fed U-$^{13}$C-glucose or U-$^{13}$C-glutamine. For simplicity, only forward flux through pyruvate carboxylase and malic enzyme was allowed.

Fluxes were computed based on the network shown in FIG. 22 with, in addition, both cytosolic and mitochondrial aspartate and alanine transamination reactions and a protein degradation reaction that produces unlabeled amino acids in balanced amounts based on their naturally occurring frequency in whole cell protein. Measurements that were used to constrain the model were glucose, glutamine, and oxygen uptake, with the latter used to constrain total NADH production and thus TCA turning; lactate and non-essential amino acid secretion; total NADPH consumption; lipid and protein synthesis rate; oxPPP flux as measured by $^{14}$C—CO$_2$ release; $^{13}$C-labeling of cellular metabolites (glucose-6-phosphate, 3-phosphoglycerate, phosphoenolpyruvate, pyruvate, lactate, citrate, α-ketoglutarate, malate and aspartate) from experiments feeding U-$^{13}$C-glucose or feeding U-$^{13}$C-glutamine; saponified fatty acid measurements from U-$^{13}$C-glucose and U-$^{13}$C-glutamine labeling experiments which were used to compute the cytosolic labeling fractions of acetyl-CoA. When indicated, the model was also constrained with the ME1 flux as measured using 2H tracers.

A cumulated isotopomer (cumomer) (Wiechert, W. et al. (1999) *"Bidirectional Reaction Steps In Metabolic Networks: III. Explicit Solution And Analysis Of Isotopomer Labeling Systems,"* Biotechnol. Bioeng. 66:69-85) balance model was generated using the carbon mapping network of central carbon metabolism and 13CFLUX2 software (Weitzel, M. et al. (2013) *"13CFLUX2—High-Performance Software Suite For $^{13}$C-Metabolic Flux Analysis,"* Bioinformatics 29:143-145). Using this model, each flux distribution simulated for both the U-$^{13}$C-glucose and U-$^{13}$C-glutamine conditions, and fluxes were optimized by minimizing the variance-weighted sum of squared residuals (Var-SSR) between the simulated and measured labeling fractions and uptake/secretion rates using the interior-point algorithm (Waltz, R. et al. (2006) *"An Interior Algorithm For Nonlinear Optimization That Combines Line Search And Trust Region Steps,"* Math. Program. 107:391-408) in MATLAB. As malate measurement represented the mixture of cytosolic and mitochondrial pools, a linear combination of two malate pools was fitted to the measured fractions. The non-convex optimization was solved starting from different initial flux distributions to account for the presence of local minima. Confidence intervals were estimated for a single reaction at a time by (i) starting from the best-scoring flux distribution, (ii) iteratively increasing or decreasing the flux through that reaction, (iii) optimizing all of the other fluxes, (iv) determining the increase in the objective function Var-SSR, (v) defining the upper and lower bounds of the confidence interval as the flux where Var-SSR increased by 3.84 ($\chi^2$ cutoff for p<0.05 with 1 degree of freedom) (Waltz, R. et al. (2006) *"An Interior Algorithm For Nonlinear Optimization That Combines Line Search And Trust Region Steps,"* Math. Program. 107:391-408).

A minimal reaction network with only cytosolic malic enzyme (ME1) fit the data less well than the network including also mitochondrial malic enzyme or pyruvate carboxylase reversibility. In the case measuring ME1 only (FIG. 22, topmost values), the malic enzyme flux was around 600 nmol per day per µl cell volume. Inclusion of mitochondrial malic enzyme (FIG. 22, middle values) did not significantly change the total malic enzyme flux, but rendered the ME1 flux indeterminant (confidence interval 0-390 nmol per day per µl cell volume). Thus, $^{13}$C-tracers were insufficient to determine cytosolic malic enzyme activity and associated NADPH production.

Use of 2,2,3,3-$^2$H-Dimethyl Succinate to Monitor Malic Enzyme Hydride Flux 2,2,3,3-$^2$H-dimethyl succinate was used to track hydride transfer mediated by malic enzyme. Tracer addition increased the cellular concentration of succinate without markedly perturbing other metabolite concentrations or fluxes. Labeling from 2,2,3,3-$^2$H-dimethyl succinate was followed through the C2 hydride of malate to NADPH and finally to newly synthesized fatty acids. NADPH labeling at its redox active hydride was analyzed by comparing the M+1 fraction of NADPH to NADP$^+$. In the absence of 2,2,3,3-$^2$H-dimethyl succinate, the NADP$^+$ and NADPH labeling patterns were identical; addition of tracer resulted in increased labeling of NADPH but not NADP$^+$ selectively in differentiating but not proliferating 3T3-L1 cells, with 3.4%±0.3% of the total adipocyte NADPH labeled. Analysis of fatty acids, which reflects specifically cytosolic NADPH, and thus ME1, similarly revealed selective $^2$H-labeling in the differentiating adipocytes, with proliferating cells exhibiting 100% M+0, and differentiating cells exhibiting approximately 60% M+0, 30% M+1, and 10% M+2. Quantitative analysis of the mass isotope distribution of a set of abundant fatty acids (omitting pre-existing fatty acids and those acquired by uptake from media, as determined by $^{13}$C-labeling data) revealed an average hydride $^2$H-labeling fraction of 2.87%±0.31%. Adjustment for the kinetic isotope effect in hydride transfer from NADPH to fat (~1.1) (Yuan, Z. et al. (1984) *"Elementary Steps in the Reaction Mechanism of Chicken Liver Fatty Acid Synthase,"* 259:6748-6751) yields an associated cytosolic NADPH labeling fraction of 3.2%±0.5%, in excellent agreement with the directly measured whole cell NADPH labeling.

The NADPH labeling fraction from [2,2,3,3-$^2$H] dimethyl succinate was converted into the fractional NADPH contribution of malic enzyme is accordance with Equation 15. Forward flux from 2,2,3,3-$^2$H-succinate results in 2,3-$^2$H-malate, i.e., M+2 malate. The observed fraction of M+2 malate was, however, only 1.5%. The larger peak was M+1 malate (10.9%). Reverse flux through malate dehydrogenase can produce M+1 malate labeled at the C3 hydride (3-$^2$H-malate). As fumarate is symmetric, fumarase will interconvert 3-$^2$H-malate and 2-$^2$H-malate. Because malic enzyme will produce NADPH selectively from malate labeled at the C2 hydride, the relative abundance of 2-$^2$H-malate versus 3-$^2$H-malate was determined. 3-$^2$H-malate (and also 2,3-$^2$H-malate) yields M+1 oxaloacetate and aspartate, whereas 2-$^2$H-malate yields unlabeled oxaloacetate and aspartate. Hence, subtracting the fraction of M+1 aspartate (6.0%) from that of M+1 plus M+2 malate gives the fraction of 2-$^2$H-malate, which was approximately 6.4%. Summing 2-$^2$H-malate and 2,3-$^2$H-malate, the fraction of malate that is capable of making NADPH was 7.9%. Thus, while 2,2,3,3-$^2$H-dimethyl succinate labeled only approximately 3.2% of NADPH, after adjusting for the extent of malate labeling and the malic enzyme kinetic isotope effect, the fraction of NADPH generated via malic enzyme was calculated to be is approximately 60%.

[4-$^2$H]Glucose as a Complementary Malic Enzyme Hydride Tracer

Dimethyl succinate is not a typical circulating nutrient. In addition, the conversion of 2,2,3,3-$^2$H-dimethyl succinate to 2-$^2$H-malate requires oxidation of succinate to fumarate by succinate dehydrogenase (Complex II) in the inner mitochondrial membrane and the resulting labeled malate must traffic to the cytosol to feed ME1. Incomplete mixing between the mitochondria and cytosol could accordingly result in overestimation of cytosolic malate labeling and thereby underestimation of ME1's contribution to NADPH. Accordingly, alternative tracer strategies involving only standard nutrients, in which labeled malate would be made directly in the cytosol were investigated.

One way to generate cytosolic 2-$^2$H-malate is via malate dehydrogenase-catalyzed reduction of oxaloacetate by NADH. 4-$^2$H-glucose can label cytosolic NADH via glyceraldehyde-3-phosphate dehydrogenase (Lewis, C. et al. (2014) "*Tracing Compartmentalized NADPH Metabolism in the Cytosol and Mitochondria of Mammalian Cells*," Mol. Cell 55:253-263. FIG. 23A shows a schematic of 4-$^2$H-glucose metabolism. Catabolism of 4-$^2$H-glucose via glycolysis labels cytosolic NADH at the glyceraldehyde-3-phosphate dehydrogenase step. The labeled hydride can then be transferred to malate position 2 via malate dehydrogenase. Hydride at malate position 2 is transferred to NADPH via malic enzyme.

4-$^2$H-glucose was therefore employed as a metabolic tracer. Cells were grown in 6 cm tissue culture dishes, and the labeled medium was replaced every day, and additionally 2 hours before extracting metabolites. Because labeling of glycolytic and oxPPP intermediates and the redox active hydride of NADPH reaches steady state over approximately 5 min, where for TCA intermediates this can take several hours, to ensure steady-state labeling, oxPPP tracing with 1-$^2$H-glucose and 1,2-$^{13}$C-glucose is performed for a minimum of 30 min and other labeling experiments for a minimum of 12 h. Metabolism is then quenched and metabolites extracted by aspirating media and immediately adding 2 mL −80° C. 80:20 methanol:water. After 20 min. of incubation on dry ice, the resulting mixture was scraped, collected into a centrifuge tube, and centrifuged at 10000 g for 5 min. Insoluble pellets were re-extracted with 1 mL −80° C. 80:20 methanol: water on dry ice. The supernatants from two rounds of extraction were combined, dried under $N_2$, resuspended in 1 mL water, and analyzed within 6 h by reversed-phase ion-pairing chromatography coupled with negative-mode electrospray-ionization high-resolution MS on a stand-alone orbitrap (Thermo) (Lu, W. et al. (2010) "*Metabolomic Analysis Via Reversed-Phase Ion-Pairing Liquid Chromatography Coupled To A Stand-Alone Orbitrap Mass Spectrometer*," Anal. Chem. 82:3212-3221). For lipid extraction, cells were quenched with 2 mL −20° C. 0.1M HCl in 50:50 methanol:water solution, incubated on ice for 20 min. The resulting supernatant was extracted with 1 mL chloroform. The chloroform extract was dried under N2, saponified with 1 mL 0.3 M KOH in 9:1 methanol:water solution at 80° C. for 1 h, and acidified by formic acid. Fatty acids were then extracted using 1 mL hexane twice. The hexane from two rounds of extraction was combined, dried under nitrogen, resuspended in 1 mL 1:1:0.3 chloroform:methanol:water, and analyzed by reversed-phase ion-pairing chromatography coupled with negative-mode electrospray ionization high-resolution MS on a quadrupole time-of-flight mass spectrometer (Agilent Technologies model 6550) (Sutterlin, H. et al. (2014) "*Accumulation Of Phosphatidic Acid Increases Vancomycin Resistance In Escherichia coli*," J. Bacteriol. 196(18):3214-3220). All isotope labeling patterns were corrected for natural $^{13}$C-abundance. FIG. 23B shows the NADP(H) $^2$H-labeling in cells fed 4-$^2$H-glucose for 24 h. FIG. 23C shows palmitate $^2$H-labeling in cells fed 4-$^2$H-glucose for 5 days. FIG. 23D shows the extent of $^2$H-labeling of malate, aspartate, whole cell NADPH, and cytosolic NADPH (inferred from fatty acid labeling) in differentiating 3T3-L1 adipocytes fed 4-$^2$H-glucose (labeling duration 24 h except for the fatty acids). Table 2 shows the fraction percentage of [M+1] malate, [M+2] malate, and [M+1] aspartate obtained using 4-$^2$H-glucose as a tracer.

TABLE 2

| Isotope | Fraction (%) |
|---|---|
| [M + 1] Malate | 12.3 ± 0.1 |
| [M + 2] Malate | 0.3 ± 0.0 |
| [M + 1] Aspartate | 4.3 ± 0.1 |

Compared to the dimethyl succinate tracer, 4-$^2$H-glucose resulted in a similar extent of 2-$^2$H-malate labeling (M+1 malate: 12.3%; M+2 malate: 0.3%; M+1 aspartate: 4.3%) and similarly resulted in fatty acid $^2$H-labeling in the differentiating but not proliferating cells (proliferating cells: 100% M+0; differentiating cells: approximately 60% M+0, 35% M+1, 5% M+2). While a small amount of labeling of NAD(P)H itself by 4-$^2$H-glucose was observed in the proliferating cells, labeling in NADP$^+$ and NADPH was equivalent, indicating incorporation of $^2$H-labeled ribose into newly synthesized NADP$^+$ without redox active hydride labeling. In contrast, preferential labeling of NADPH was observed in the differentiating adipocytes. Quantitatively, the extent of redox active hydride labeling was identical within error for both the 4-$^2$H-glucose and the dimethyl succinate tracer.

Integration of the ME1 flux constraint from the $^2$H-tracers with the nutrient uptake, waste excretion, and $^{13}$C-tracer data via quantitative metabolic flux analysis of the network including cytosolic and mitochondrial malic enzyme resulted in a coherent set of whole cell fluxes (ME1(constrained)/⅔ in FIG. 22). In the absence of pyruvate carboxylase or malic enzyme reversibility, all fluxes were well-defined. Inclusion of such reversibility rendered mitochondrial fluxes indeterminant without affecting the fit or impacting ME1 flux. The confidence interval for NADPH production rate ranged from 0.4% to 0.8% of the glucose uptake rate for the oxPPP and 2.7% to 3.5% for ME1.

Genetic Confirmation of ME1's NADPH Contribution

Both ME1 and ME2 (NADH-producing mitochondrial malic enzyme) have been previously shown based on shRNA knockdown to be required for adipocyte differentiation (Jiang, P. et al. (2013) "*Reciprocal Regulation Of P53 And Malic Enzymes Modulates Metabolism And Senescence,*" Nature 493:689-693). It was observed that ME1 protein, but not ME2 or ME3 protein, increased dramatically during adipocyte differentiation. To evaluate the functional significance of ME1 relative to other cytosolic NADPH-producing enzymes, G6PD (the committed enzyme of the oxPPP), MTHFD1 (required for cytosolic one-carbon unit oxidation), IDH1 (the cytosolic NADPH-generating isocitrate dehydrogenase), and ME1 were knocked down on differentiation day 2. Silencing ME1, but not the other enzymes, decreased fatty acid accumulation in the differentiating adipocytes. Moreover, ME1 knockdown decreased carbon flux from malic acid to pyruvate and fatty acid labeling from 2,2,3,3-$^2$H-dimethyl succinate. Thus, ME1 is the main source of NADPH to drive fatty acid synthesis in adipocytes and is required for effective lipogenesis.

Impact of Hypoxia on Adipocyte Metabolism

The quantitative flux analysis in the differentiating adipocytes revealed a metabolic cycle in which pyruvate is generated by malic enzyme and consumed by pyruvate dehydrogenase. This cycle is efficient in terms of minimizing the transport of substrates between the cytosol and mitochondrion (FIG. 24). In order to determine whether malic enzyme would continue to be the predominant NADPH source under conditions where the cycle is disrupted, such as by inhibition of pyruvate dehydrogenase activity in hypoxia (Kim, J. W. et al. (2006) "*HIF-1-Mediated Expression Of Pyruvate Dehydrogenase Kinase: A Metabolic Switch Required For Cellular Adaptation To Hypoxia,*" Cell. Metab. 3:177-185; Lu, C. W. et al. (2008) "*Induction Of Pyruvate Dehydrogenase Kinase-3 By Hypoxia-Inducible Factor-1 Promotes Metabolic Switch And Drug Resistance,*" J. Biol. Chem. 283:28106-28114).

Understanding the impact of hypoxia on differentiating adipocyte metabolism is of medical relevance, as obesity has been proposed to result in hypoxia in adipose tissue (Hosogai, N. et al. (2007) "*Adipose Tissue Hypoxia In Obesity And Its Impact On Adipocytokine Dysregulation,*" Diabetes 56:901-911; Trayhurn, P. (2013) "*Hypoxia And Adipose Tissue Function And Dysfunction In Obesity,*" Physiol. Rev. 93"1-21). Thus, the metabolic tracer methods disclosed above have utility in the diagnosis and prognosis of metabolic diseases, and in particular obesity and diabetes.

Expression of adipocyte differentiation markers and accumulation of cellular fatty acids proceeded in hypoxia (1% oxygen). The source of the fatty acid carbon, however, changed, from being mainly glucose to becoming mainly glutamine, as occurs also in hypoxic cancer cells (Mullen, A. R. et al. (2011) "*Reductive Carboxylation Supports Growth In Tumour Cells With Defective Mitochondria,*" Nature 481:385-388; Kamphorst, J. J. et al. (2014) "*Quantitative Analysis Of Acetyl-CoA Production In Hypoxic Cancer Cells Reveals Substantial Contribution From Acetate,*" Cancer Metab. 2:1-8). In contrast to cancer cells, however, the contribution of acetate was substantial in normoxia and did not increase in hypoxia (FIG. 25). Thus, the metabolic tracer methods disclosed above have utility in the diagnosis and prognosis of cancer.

To evaluate NADPH production routes in hypoxic differentiating adipocytes, hydride labeling was traced into fat from 1-$^2$H-glucose in order to probe the oxPPP. Additionally, both 2,2,3,3-$^2$H-dimethyl succinate and 4-$^2$H-glucose were used to probe malic enzyme. Hypoxia resulted in markedly increased labeling from the oxPPP tracer and nearly completed elimination of labeling from both malic enzyme tracers (FIG. 26, Panels A-D). Associated quantitation, correcting for substrate labeling and the deuterium kinetic isotope effect, revealed that the contribution of the oxPPP increased from 21%±4% in normoxia to 55%±5% in hypoxia, whereas the contribution of malic enzyme decreased from 60%±5% to 3%±2% (mean±s.d., n=3). Thus, in response to hypoxia, the main lipogenic NADPH source switches from malic enzyme to the oxPPP. The metabolic tracer methods disclosed above thus have utility in the assessment of normoxia/hypoxia.

Thus, although the utility of 1-$^2$H-Glucose, 3-$^2$H-Glucose and 2,3,3-$^2$H-serine for tracing NADPH production via the PPP and folate metabolism was recently established (Fan, J. et al. (2014) "*Quantitative Flux Analysis Reveals Folate-Dependent NADPH Production,*" Nature 510:298-302; Lewis, C. et al. (2014) "*Tracing Compartmentalized NADPH Metabolism in the Cytosol and Mitochondria of Mammalian Cells,*" Mol. Cell 55:253-263), a suitable tracer for malic enzyme was previously lacking. The above Example establishes that 4-$^2$H-Glucose is a suitable tracer for malic enzyme.

The results presented above demonstrate the ability of both 2,2,3,3-$^2$H-dimethyl-succinate and 4-$^2$H-glucose to trace hydride flux from malate to NADPH and subsequently into fat. Combining this approach with $^{13}$C-labeling studies shows that malic enzyme is the main NADPH source in normoxic 3T3-L1 adipocytes with total NADPH production more than double the PPP. While adipocyte differentiation and associated fat synthesis continues in hypoxia, the mode of NADPH production dramatically changes, with malic enzyme's contribution becoming minimal and the oxPPP contribution becoming predominant.

In summary, NADPH metabolism was thus evaluated in adipocytes (3T3-L1 cells), which upon differentiation stop growing but remain biosynthetically active. The data show that both total biosynthetic NADPH demand and NADPH production increase upon differentiation, to a level comparable to typical transformed cells. The overall metabolic requirements of differentiating adipocytes are, however, quite distinct. Differentiating adipocytes do not engage in significant nucleotide synthesis and thus have minimal need for ribose phosphate and 10-formyl-THF. Consistent with this, the fractional NADPH contribution of these pathways decreases. Instead, in normoxic differentiating adipocytes, most NADPH is made by malic enzyme. This determination was proven using a combination of classical $^{13}$C-glutamine tracing into pyruvate augmented by more global flux analysis and a newly developed method for tracing malic enzyme hydride flux by feeding either 2,2,3,3-$^2$H-dimethyl succinate or 4-$^2$H-glucose. Each of these tracers produces 2-$^2$H-malate which in turn makes NADPH and $^2$H-labeled fatty acids.

Normoxic adipocytes rely on malic enzyme, and this reliance changes when the cells are subjected to hypoxia. The present invention suggests an explanation for this phenomenon. Fatty acid synthesis requires cytosolic acetyl-CoA. Pyruvate is converted to acetyl-CoA selectively in the mitochondrion. This acetyl-CoA is carried into the cytosol as citrate, made by condensation with oxaloacetate (which can be produced in the mitochondrion by pyruvate carboxylation or glutamine oxidation). Citrate is then re-converted into oxaloacetate and acetyl-CoA in the cytosol by ATP-citrate lyase (Wellen, K. E. et al. (2009) "*ATP-Citrate Lyase Links Cellular Metabolism To Histone Acetylation*," Science 324: 1076-1080). Reduction of oxaloacetate by cytosolic malate dehydrogenase yields cytosolic malate. Conversion of this malate into pyruvate and NADPH by malic enzyme regenerates pyruvate. This cycle (Boucher, A. et al. (2004) "*Biochemical Mechanism Of Lipid-Induced Impairment Of Glucose-Stimulated Insulin Secretion And Reversal With A Malate Analogue*," J. Biol. Chem. 279:27263-27271) serves dual purposes in adipocytes: (i) production of cytosolic acetyl-CoA and (ii) generation of NADPH from reducing equivalents originally derived from glycolysis as NADH.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating cancer in a cancer patient, wherein said method comprises administering to said cancer patient:
   (A) an anti-folate anticancer agent; and
   (B) one or more metabolic compound(s) selected from the group consisting of: formate, methyl formate, triethyl orthoformate, trimethyl orthoformate, glycine, 10-formyl-THF, and methylene-THF; with the proviso that said one or more metabolic compound(s) of said group is not ethyl formate; and
   (C) a pharmaceutically acceptable excipient, carrier or diluent; wherein:
   (i) said anti-folate anticancer agent is administered in an amount sufficient to inhibit an enzyme of folate metabolism; and
   (ii) said metabolic compound(s) is administered in amount(s) sufficient to remediate the effect of the inhibition of folate metabolism on thymine synthesis, formate synthesis, glycine synthesis or purine synthesis in non-cancer cells caused by said anti-folate anticancer agent or to increase the therapeutic index of said anti-folate anticancer agent; and
   (iii) said cancer is an adrenal gland tumor, an AIDS-associated cancer, an alveolar soft part sarcoma, an astrocytic tumor, a bladder cancer, a bone cancer, a brain and spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gastric cancer, a gestational trophoblastic disease, a germ cell tumor, a head and neck cancer, a hepatocellular carcinoma, an islet cell tumor, a Kaposi's sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

2. The method of claim 1, wherein said anti-folate anticancer agent is an inhibitor of an enzyme of folate metabolism selected from the group consisting of: an inhibitor of dihydrofolate reductase (DHFR); an inhibitor of β-glycinamide ribonucleotide transformylase (GARFT); an inhibitor of 5'-amino-4'-imidazolecarboxamide ribonucleotide transformylase (AICARFT); an inhibitor of thymidylate synthetase (TYMS); an inhibitor of methylene tetrahydrofolate dehydrogenase 1 (MTHFD1); an inhibitor of methylene tetrahydrofolate dehydrogenase 2 (MTHFD2); an inhibitor of serine hydroxymethyltransferase 1 (SHMT1); an inhibitor of serine hydroxymethyltransferase 2 (SHMT2); an inhibitor of formyltetrahydrofolate dehydrogenase 1 (ALDH1L1) and an inhibitor of formyltetrahydrofolate dehydrogenase 2 (ALDH1L2).

3. The method of claim 2, wherein said anti-folate anticancer agent is an inhibitor of serine hydroxymethyltransferase 1 (SHMT1).

4. The method of claim 3, wherein said anti-folate anticancer agent that is an inhibitor of serine hydroxymethyltransferase 1 (SHMT1) is:
(1) (R)-6-amino-4-(3,5-bis(trifluoromethyl)phenyl)-4-isopropyl-3-methyl-1,4-dihydropyrano[2,3-c]pyrazole-5-carbonitrile; or
(2) (S)-6-amino-4-(3,5-bi s(trifluoromethyl)phenyl)-4-isopropyl-3-methyl-1,4-dihydropyrano[2,3-c]pyrazole-5-carbonitrile.

5. The method of claim 2, wherein said anti-folate anticancer agent is a formate ester of said inhibitor.

6. The method of claim 1, wherein said anti-folate anticancer agent is selected from the group consisting of: aminopterin; methotrexate; raltitrexed; pemetrexed; pralatrexate; 10'-deazaaminopterin; lometrexol; edatrexate; talotrexin; piritrexim and nolatrexed, and a formate ester thereof.

7. The method of claim 1, wherein said one or more administered metabolic compounds includes methyl formate, triethyl orthoformate, or trimethyl orthoformate.

8. The method of claim 1, wherein prior to said administering, said method comprises:
(1) administering deuterated serine to cancer cells of said cancer patient; and
(2) measuring the production of:
 (a) deuterated NADPH from said deuterated compound; or
 (b) a deuterated product of NADPH-driven reductive biosynthesis; by said cancer cells.

9. The method of claim 8, wherein prior to said administering, said method comprises:
(1) administering said anti-folate anticancer agent and deuterated serine to cancer cells of said cancer patient; and
(2) measuring the production of:
 (a) deuterated NADPH from said deuterated compound; or
 (b) a deuterated product of NADPH-driven reductive biosynthesis; by said cancer cells.

10. The method of claim 8, wherein said method comprises measuring said production of a deuterated product of NADPH-driven reductive biosynthesis, and said deuterated product is a fatty acid, pyrroline-5-carboxylate (P5C) or proline.

11. The method of claim 9, wherein said method comprises measuring said production of a deuterated product of NADPH-driven reductive biosynthesis, and said deuterated product is a fatty acid, pyrroline-5-carboxylate (P5C) or proline.

12. The method of claim 1, wherein said one or more metabolic compound(s) includes formate.

13. The method of claim 1, wherein said one or more metabolic compound(s) includes said methyl formate, triethyl orthoformate, or trimethyl orthoformate.

14. The method of claim 1, wherein said one or more metabolic compound(s) includes 10-formyl-THF or methylene-THF.

15. The method of claim 1, wherein said one or more metabolic compound(s) includes glycine.

* * * * *

SEQUENCE LISTING

```
<160> NUMBER OF SEQ ID NOS: 9

<210> SEQ ID NO 1
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of MTHFD1 Gene

<400> SEQUENCE: 1
ccgggctgaa gagattggga tcaaactcga gtttgatccc aatctcttca gcttttg        58

<210> SEQ ID NO 2
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of MTHFD1 Gene

<400> SEQUENCE: 2
ccgggccatt gatgctcgga tatttctcga gaaatatccg agcatcaatg gcttttg        58

<210> SEQ ID NO 3
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of MTHFD2 Gene

<400> SEQUENCE: 3
ccgggcagtt gaagaaacat acaatctcga gattgtatgt tcttcaact gcttttg         58

<210> SEQ ID NO 4
<211> LENGTH: 58
<212> TYPE: DNA
<213> ORGANISM: Artificial Sequence
<220> FEATURE:
<223> OTHER INFORMATION: Polynucelotide for Expressing shRNA for
      Knockdown of MTHFD2 Gene

<400> SEQUENCE: 4
ccgggctggg tatatcactc cagttctcga gaactggagt gatataccca gcttttg        58

<210> SEQ ID NO 5
<211> LENGTH: 58
<212> TYPE: DNA
<213> ORGANISM: Artificial Sequence
<220> FEATURE:
```

```
<223> OTHER INFORMATION: Polynucleotide for Expressing shRNA for
      Knockdown of G6PD Gene

<400> SEQUENCE: 5
ccggcaacag atacaagaac gtgaactcga gttcacgttc ttgtatctgt tgttttg         58

<210> SEQ ID NO 6
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of G6PD Gene

<400> SEQUENCE: 6
ccgggctgat gaagagagtg ggtttctcga gaaacccact ctcttcatca gctttttg        58

<210> SEQ ID NO 7
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of NNT Gene

<400> SEQUENCE: 7
ccggccctat ggttaatcca acattctcga gaatgttgga ttaaccatag ggttttg         58

<210> SEQ ID NO 8
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of ME1 Gene

<400> SEQUENCE: 8
ccgggccttc aatgaacggc ctattctcga gaataggccg ttcattgaag gctttttg        58

<210> SEQ ID NO 9
<211> LENGTH: 58
<212> TYPE: DNA
<213> ORGANISM: Artificial Sequence
<220> FEATURE:
<223> OTHER INFORMATION: Polynucleotide for Expressing shRNA for
      Knockdown of ME1 Gene

<400> SEQUENCE: 9
ccggccaaca atatagtttg gtgttctcga gaacaccaaa ctatattgtt ggttttg         58
```